(12) United States Patent
Disis et al.

(10) Patent No.: US 9,060,961 B2
(45) Date of Patent: Jun. 23, 2015

(54) MOLECULES AND METHODS FOR TREATMENT AND DETECTION OF CANCER

(75) Inventors: Mary L. Disis, Renton, WA (US); Vivian Goodell, San Diego, CA (US); Hailing Lu, Seattle, WA (US); Douglas G. McNeel, Madison, WI (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 970 days.

(21) Appl. No.: 12/446,953

(22) PCT Filed: Nov. 9, 2007

(86) PCT No.: PCT/US2007/084312
§ 371 (c)(1),
(2), (4) Date: Apr. 23, 2009

(87) PCT Pub. No.: WO2008/073660
PCT Pub. Date: Jun. 19, 2008

(65) Prior Publication Data
US 2010/0092523 A1 Apr. 15, 2010

Related U.S. Application Data

(60) Provisional application No. 60/865,145, filed on Nov. 9, 2006, provisional application No. 60/945,298, filed on Jun. 20, 2007.

(51) Int. Cl.
*A61K 38/00* (2006.01)
*A61K 39/00* (2006.01)
*A61K 38/17* (2006.01)
*G01N 33/574* (2006.01)

(52) U.S. Cl.
CPC ......... *A61K 39/0011* (2013.01); *A61K 39/0005* (2013.01); *A61K 38/1754* (2013.01); *A61K 38/1796* (2013.01); *G01N 33/57488* (2013.01); *G01N 2333/475* (2013.01); *G01N 2333/65* (2013.01); *G01N 2333/72* (2013.01); *G01N 2800/52* (2013.01)

(58) Field of Classification Search
USPC ........ 530/300, 326, 350; 536/23.5; 424/185.1
See application file for complete search history.

(56) References Cited

U.S. PATENT DOCUMENTS

| | | | | |
|---|---|---|---|---|
| 7,109,030 | B2 * | 9/2006 | Dedera et al. | 435/325 |
| 2004/0181830 | A1 * | 9/2004 | Kovalic et al. | 800/289 |
| 2005/0221305 | A1 | 10/2005 | Nelson | |
| 2005/0240014 | A1 * | 10/2005 | Sheppard et al. | 536/23.5 |
| 2006/0153853 | A1 * | 7/2006 | Forbes | 424/155.1 |
| 2007/0061916 | A1 * | 3/2007 | Kovalic et al. | 800/278 |
| 2008/0242603 | A1 * | 10/2008 | Wang et al. | 514/12 |

FOREIGN PATENT DOCUMENTS

| | | | |
|---|---|---|---|
| WO | WO02098914 A2 * | 12/2002 | |
| WO | WO/03/064593 | 8/2003 | |
| WO | WO/2004/063325 | 7/2004 | |
| WO | WO2005082934 A2 * | 9/2005 | |
| WO | WO2006012451 A2 * | 2/2006 | |
| WO | WO2006081430 A2 * | 8/2006 | |

OTHER PUBLICATIONS

Binkert et al. (EMBO J. Sep. 1989; 8 (9): 2497-2502).*
Baron-Hay, S., et al. "Elevated serum insulin-like growth factor binding protein-2 as a prognostic marker in patients with ovarian cancer" 2004, *Clin Cancer Res* 10:1796-1806.
Busund, L.T. et al. "Significant expression of IGFBP2 in breast cancer compared with benign lesions", 2005, *J Clin Pathol* 58:361-366.
Clark, R., "The Somatogenic hormones and insulin-like growth factor-1: stimulators of lymphocytes and immune function", *Endocrine Reviews*, 1997, 18(2):157-179.
Di Modugno, F. et al., "Human Mena Protein, A serex-defined antigen overexpressed in breast cancer eliciting . . . response", 2004, *Int J Cancer* 109: 909-918.
Disis, M.L., et al., "Global role of the immune system in identifying cancer initiation and limiting disease progression", 2005, *J Clinical Oncology* 23:(35) 8923-8925.
Disis, M.L., et al., "Molecular targeting with cancer vaccines", 2005, *J Clinical Oncology* 23:(22) 4840-4841.
Disis, M.L., et al., Soluble cytokines can act as effective adjuvants in plasmid DNA vaccines targeting . . . antigens, 2003, *Immunobiology* 207: 1-8.
Flyvbjerg, A., et al., "Elevated Serum insulin-like growth factor-binding protein 2 (IGFBP2) and decreased IGFBP-3 . . . inhibitor", 1997 *J Clin Endocrinol Metab.* 82(7): 2308-13.
Foll, J.L. et al., "Activation-dependent expression of the insulin-like growth factor binding protein-2 in human lymphocytes", *Immunology*, 1998, 94:173-180.
Fottner, Ch. et al., "Role of the insulin-like growth factor system in adrenocortical growth control and carcinogenesis", 2004, *Horm Metab Res* 36: 397-405.
Gnjatic, S., et al., "Survey of naturally occurring CD4+ T cell responses against NY-ESO-1 in cancer patients: correlation . . . responses", 2003, *Proc Nati Aced Sci* 100(15):8862-8867.
Hoeflich, A. et al., "Insulin-like growth factor-binding protein 2 in tumorigenesis: protector or promoter?", 2001, *Cancer Res.* 61: 8601-10.
Jager, D., et al. "Identification of tumor antigens as potential target antigens for immunotherapy by serological . . . cloning", 2004, *Cancer Immunol Immunother* 53:144-147.

(Continued)

*Primary Examiner* — Stephen Rawlings
(74) *Attorney, Agent, or Firm* — Karen S. Canady; canady + lortz LLP

(57) ABSTRACT

The invention provides a method for inhibiting proliferation of cancer cells, as well as methods for detecting and treating various cancers, including cancer of the ovary, breast, prostate and colon. The method comprises contacting a cancer cell with an IGF-related molecule of the invention or administering an IGF-related vaccine to the cancer patient. In one embodiment, the molecule is an immunogenic peptide derived from IGFBP-2 or from IGF1 R. The invention additionally provides methods for detecting and treating cancer using IGF-related molecules.

36 Claims, 28 Drawing Sheets
(2 of 28 Drawing Sheet(s) Filed in Color)

(56) References Cited

OTHER PUBLICATIONS

Kanety, H. et al., "Increased insulin-like growth factor binding protein-2 (IFGBP-2) gene expression and protein production . . . fluid", 1996, *Br J Cancer* 73: 1069-73.

Karasik, A. et al., "Insulin-like growth factor-I (IGF-I) and IGF-binding protein-2 are increased in cyst fluids of epithelial . . . cancer", 1994,*J Clin Endocrinol Metab.* 78: 271-6.

Kawamoto, K. et al., "Expression of Insulin-like growth factor-2 can predict the prognosis of human colorectal cancer patients . . . survival", 1998, *Oncology.* 55: 242-8.

Lee, E.-J., et al., "Insulin-like growth factor binding protein 2 promotes ovarian cancer cell invasion", 2005, *Molecular Cancer* 4:7.

Martin, J.L. et al., "Expression of insulin-like growth factor binding protein-2 by MCF-7 breast cancer cells is regulated through . . . Pathway", 2007, *Endocrinology* 148:2532-2541.

Mehrian-Shai, R. et al. "Insulin growth factor-binding protein 2 is a candidate biomarker for PTEN status and PI3K/Akt . . . cancer", 2007, *Proc Natl Aced Sci USA* 104(13):5563-5568.

Miraki-Moud, F., et al., "Increased levels of insulin-like growth factor binding protein-2 in sera and tumors from patients . . . acromegaly", 2001, *Clin Endocrinol (Oxf).* 54: 499-508.

Mita, K., et al., "Expression of the insulin-like growth factor system and cancer progression in hormone-treated prostate cancer patients", 2000, *Int J Urol.* 7: 321-9.

Nakatsura, T., et al., "Cellular and humoral immune responses to a human pancreatic cancer antigen, coactosin-like protein . . . method", 2002. *Eur J Immunol* 32:826-836.

Perks, C.M., et al., "IGF-II and IGFBP-2 differentially regulate PTEN in human breast cancer cells", 2007, *Oncogenel* 26(40):5966-572.

Pollak, M.N. et al., "Insulin-like growth factors and neoplasia", 2004, *Nat Rev Cancer* 4:505-518.

Renehan, A.G. et al. "Elevated serum insulin-like growth factor (IGF)-II and IGF binding protein-2 in patients with colorectal cancer", 2000, *Br J Cancer* 83(10):1344-1350.

Salazar, L. et al., "Cancer Vaccines: the role of tumor burden in tipping the scale toward vaccine efficacy", 2005, *J Clinical Oncology* 23(30):7397-7398.

Schutt, B.S., et al., "Integrin-mediated action of insulin-like growth factor binding protein-2 in tumor cells", 2004, *J Mol Endocrinol* 32:859-868.

Shariat, S. F. et al. "Association of preoperative plasma levels of insulin-like growth factor I and insulin-like growth factor binding . . . metastasis", 2002, *J Clin Oncol.* 20:833-41.

Stattin, P., et al., "Plasma Insulin-like growth factor-I, insulin-like growth factor-binding proteins, and prostate cancer . . . study", 2000, *J Natl Cancer Inst.* 92: 1910-7.

Thompson, J. et al., "Tumor cells transduced with the MHC class II transactivator and CD80 activate . . . chain", 2006, *Cancer Res* 66:(2) 1147-1154.

Wang, H., et al., "Insulin-like growth factor-binding protein 2 and 5 are differentially regulated in ovarian cancer of different histologic types", 2006, *Modem Pathology* 1-8.

Yu, H., et al. "Levels of insulin-like growth factor I (IGF-I) and IGF binding proteins 2 and 3 in serial postoperative serum samples . . . recurrence", 2001, *Urology* 57:471-475.

\* cited by examiner

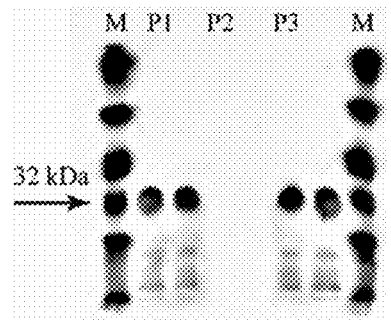

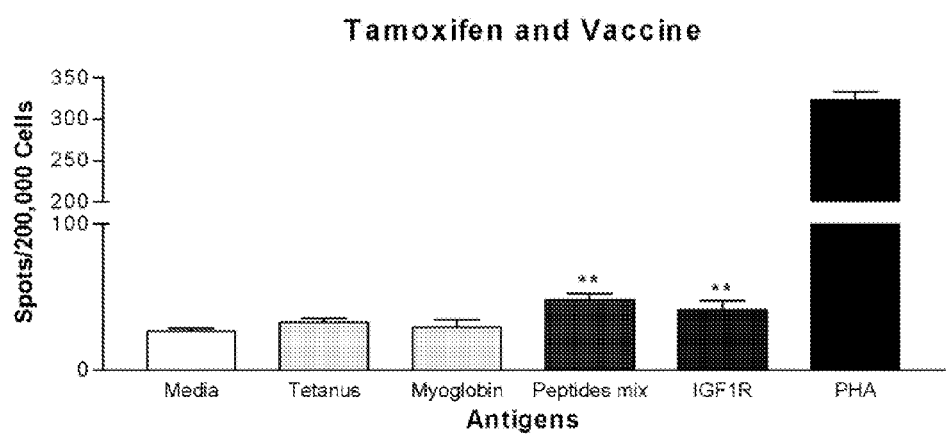
Figure 26D
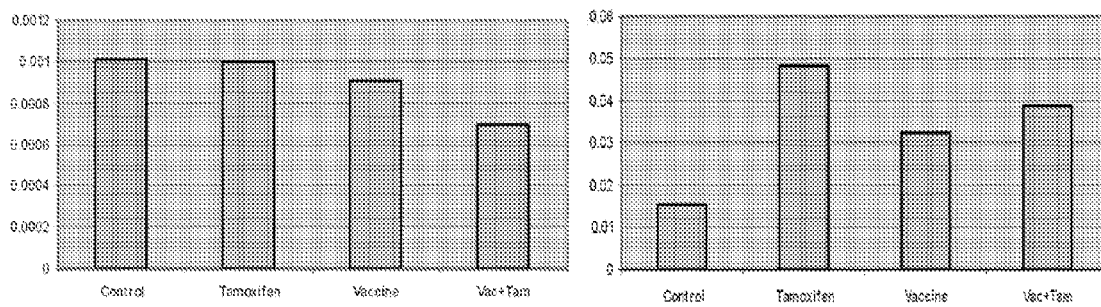
Figure 27A
Figure 27B
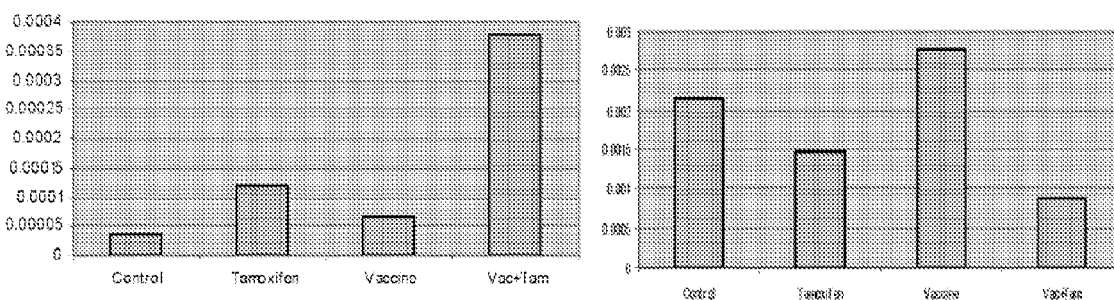
Figure 27C
Figure 27D

MOLECULES AND METHODS FOR TREATMENT AND DETECTION OF CANCER

This application claims benefit of U.S. provisional patent applications No. 60/865,145, filed Nov. 9, 2006, and No. 60/945,298, filed Jun. 20, 2007, the entire contents of each of which are incorporated by reference into this application.

STATEMENT REGARDING FEDERALLY SPONSORED RESEARCH

The Invention disclosed herein was made with Government support under Grant No. RO1CA101190, awarded by the National Cancer Institute and Grant No. CA85218 (K24) awarded by the National Institutes of Health. The Government has certain rights in this invention.

TECHNICAL FIELD OF THE INVENTION

The present invention relates generally to detection, diagnosis, monitoring and therapy of cancer. The invention more specifically pertains to insulin-like growth factor-related molecules, including insulin-like growth factor binding protein-2 (IGFBP2) and insulin-like growth factor-1 receptor (IGF1R) molecules, as therapeutic and diagnostic targets. The molecules of the invention can be used in vaccines and pharmaceutical compositions for the treatment of various cancers associated with IGFBP/IGFR-related molecules, as well as in methods of detecting and assessing and/or monitoring the malignancy of such cancers.

BACKGROUND OF THE INVENTION

Cancer and infectious disease are significant health problems throughout the world. Although advances have been made in detection and therapy of these diseases, no vaccine or other universally successful method for prevention or treatment is currently available. Current therapies, which are generally based on a combination of chemotherapy or surgery and radiation, continue to prove inadequate in many patients.

Identification of human tumor antigens is critical to the development of immune-based treatments targeting tumors, such as cancer vaccines. Tumor antigens are proteins that are immunogenic in patients with cancer but not in subjects who are non-tumor bearing. Thus, the pre-existent immune response to tumor associated proteins has been exploited as a tool for antigen discovery. Melanoma antigens have been identified by screening tumor-associated proteins encoded in reporter cells with autologous T cells specific for the patient's tumor. T cell-based methods of antigen discovery are laborious and require autologous tumor both for the generation of the reporter cells as well as the tumor specific T cells used to detect responses.

Cancer patients also have antibody immunity directed against tumor associated proteins and more recent methods of antigen discovery have focused on the use of tumor specific antibodies as probes for screening potential tumor antigens. Genomic and proteomic techniques, applied to the discovery of tumor antigens, have allowed immunogenic proteins to be identified without the use of autologous tumor cells. Both approaches utilize a humoral immune response to screen for tumor specific antigens. Many of the tumor specific IgG antibody responses identified in this fashion are high titer implying recognition by T helper cells. Antigens discovered using IgG antibody immunity as a screening tool can be considered to be recognized by the T helper cell repertoire and, potentially, cytotoxic T cells (CTL). High-throughput serologic antigen discovery methods have resulted in dozens of tumor antigens being identified, however, the function or relevance of many of these immunogenic proteins is not known.

Self-proteins have been identified as tumor antigens. These proteins are not mutated in any way, but are clearly immunogenic in patients with cancer. Many of these proteins are present at much higher concentrations in malignant cells than in the normal cells with which they are associated. Overexpression of self-proteins may allow subdominant epitopes to be presented in the MHC in high enough density to elicit a T cell response. Indeed, the peptide repertoire display in the MHC when a protein is overexpressed may be distinctly different from the peptides present in resting MHC where that same protein is present at basal levels. Protein overexpression in a cancer cell, therefore, may result in making that protein a tumor antigen. The demonstration of detectable immunity directed against a self-tumor antigen suggests that some level of immunologic tolerance has been circumvented, that the ability to recognize the antigen is within the realm of the human T cell repertoire, and that the immune response may be boosted by active immunization.

The success of any targeted cancer therapy depends on eradicating cells that express essential targets, i.e. proteins that maintain or impact the malignant phenotype, and cancer vaccines are no exception. HER-2/neu is a biologically relevant tumor antigen and aberrant signaling via the receptor is an important growth regulator for breast cancers expressing the protein. However, multiple oncogenic pathways are implicated in breast cancer progression; thus, additional essential immunologic targets need to be defined to enhance the therapeutic efficacy of immunization and impact tumor growth.

The insulin like growth factor (IGF) pathway is emerging as an important growth regulator in breast cancer. IGF signaling stimulates proliferation and inhibits apoptosis in cancer cells (Pollak, M. N., et a. 2004. *Nat Rev Cancer* 4:505-518). In particular, insulin like growth factor receptor binding protein 2 (IGFBP-2) has been shown to be increasingly overexpressed during breast cancer progression (Busund, L. T., et al. 2005. *J Clin Pathol* 58:361-366). Recent studies have suggested that not only does IGFBP-2 have a direct proliferative effect on tumor growth, the protein is a regulator of PI3K/Akt activation and may facilitate the malignant transformation (Mehrian-Shai, R., et al. 2007. *Proc Natl Acad Sci USA* 104:5563-556811-13; Martin, J. L., and Baxter, R. C. 2007. *Endocrinology* 148:2532-2541; Perks, C. M., et al. 2007. *Oncogenel* 26(40):5966-572). Stimulating immune eradication of IGFBP-2 overexpressing breast cancer cells may potentially impact cancer progression.

Due to the limitations and challenges posed by currently available approaches to cancer diagnosis and therapy, there is a need in the art for the development of alternative methods and compositions. The present invention fulfills this need, and further provides other related advantages.

SUMMARY OF THE INVENTION

The invention meets these needs and others by providing compositions and methods for the treatment and detection of multiple cancers. More specifically, the present invention relates to compositions and methods for detecting, monitoring, and treating malignancies associated with IGFBP-2 and/or IGF1R and related proteins (referred to herein as "IGF-related proteins"), in a warm-blooded animal. These methods may be used on a one time basis when a malignancy is suspected or on a periodic basis (e.g., to monitor an individual with an elevated risk of acquiring or reacquiring a malignancy). In one embodiment, the method comprises the following steps: (a) contacting a bodily fluid suspected of containing antibodies specific for an IGF-related protein with the IGF-related protein; (b) incubating the combination of bodily fluid and IGF-related protein for a duration and under conditions that are sufficient for the formation of immunocomplexes; and (c) detecting the presence or absence of immunocomplex formation between the IGF-related protein and antibodies specific for the IGF-related protein in the bodily fluid, thereby determining the presence or absence of the malignancy associated with the over-expression of IGF-related protein.

The invention also provides methods for monitoring the effectiveness of cancer therapy involving malignancies associated with the over-expression of an IGF-related protein, in a warm-blooded animal. Such methods may be used for early detection of relapse from cancer therapy, for example. In one embodiment, the method comprises: (a) contacting a first bodily fluid sample, taken from the warm-blooded animal prior to initiation of therapy, with an IGF-related protein; (b) incubating the bodily fluid for a duration and under conditions that are sufficient for immunocomplex formation; (c) detecting immunocomplex formation between the IGF-related protein and antibodies specific for the IGF-related protein in the bodily fluid; (d) repeating steps (a), (b), and (c) on a second bodily fluid sample taken from the animal subsequent to the initiation of therapy; and (e) comparing the immunocomplex formations detected in the first and second bodily fluid samples, thereby monitoring the effectiveness of the therapy in the animal.

In another embodiment, the method for the detection of malignancy comprises: (a) isolating CD4$^+$T cells from a warm-blooded animal; (b) incubating the T cells with an IGF-related protein; and (c) detecting the presence or absence of specific activation of the T cells, thereby detecting the presence or absence of the malignancy. In another related embodiment, the method involves isolating CD8$^+$ T cells from a warm-blooded animal, and subjecting them to procedures described above in (b) and (c) applied to the CD4$^+$T cells. The invention is also directed toward methods for treating malignancies associated with the over-expression of an IGF-related protein. In one embodiment, the method comprises: (a) isolating CD4$^+$ T cells from a warm-blooded animal; (b) incubating the T cells in the presence of the IGF-related protein resulting in T cell proliferation; and (c) administering to the warm-blooded animal an effective amount of the proliferated T cells. In another related embodiment, the method for treatment involves isolating CD8$^+$ T cells from a warm-blooded animal, and subjecting them to procedures described above in (b) and (c) applied to the CD4$^+$T cells. In a further embodiment, the method for treatment comprises: (a) isolating CD4$^+$T cells from a warm-blooded animal; (b) incubating the T cells in the presence of the IGF-related protein resulting in T cell proliferation; (c) cloning one or more cells that proliferated in the presence of the IGF-related protein; and (d) administering to the warm-blooded animal an effective amount of the cloned T cells. In a related embodiment, the method for treatment involves isolating CD8$^+$ T cells from a warm-blooded animal, and subjecting them to procedures described above in (b) and (c) applied to the CD4$^+$T cells.

The invention provides anticancer therapeutic compositions comprising T cells proliferated in the presence of an IGF-related protein, in combination with a pharmaceutically acceptable carrier or diluent. In another embodiment, the invention relates to methods for treating malignancies by the administration of anti-cancer therapeutic compositions to a warm-blooded animal (i.e., immunization). The anti-cancer therapeutic compositions are comprised of one or several types of IGF-related peptides that are immunogenic, including full-length proteins, and including polynucleotides encoding the IGF-related peptides and/or proteins. The IGF-related peptides could be administered with a pharmaceutically acceptable carrier or diluent, as well as in combination with peptides derived from a different tumor antigen. The IGF-related peptide vaccine could be administered concurrently with lymphokine molecules.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 11A-B. Breast cancer patients can have antibody immunity to IGFBP-2. FIG. 11A: IGFBP-2 ELISA results for 220 breast cancer patients and 100 normal donors. Lines: mean level of IGFBP-2-specific IgG immunity for each sample group. FIG. 11B: Western blot analysis of representative samples positive and negative by indirect ELISA. M: molecular weight marker; P1, P3: replicates of ELISA-positive patient samples; P2: replicates of ELISA-negative sample; Arrow: 32 kDa level of molecular weight marker (IGFBP-2 36 kD).

FIG. 12A-B. The majority of IGFBP-2 peptides identified by a scoring system combining multiple MHC Class II peptide binding algorithms can be recognized by human T cells. FIG. 12A: IGFBP-2 amino acid sequence (SEQ ID NO: 1) and 14 peptides associated with highest binding affinity across multiple MHC class II alleles, are shown. Colors represent final scores from five algorithms for each amino acid from dark red to light blue in the order of rank scores. Color strata are as follows: dark red≥9,000; red=8000-9000; orange=7,000-8,000; light orange=6,000-7,000; gold=5,000-6,000; tan=4,000-5,000; yellow=3,000-4,000; light yellow=2,000-3,000; light green=1,000-2,000; light blue=500-1,000. FIG. 12B: Percent of volunteer donors (white bars) and cancer patients (black bars) showing T cell responses to specific IGFBP-2 peptides.

(FIG. 13A) no response, (FIG. 13B) dominant response to one epitope, and (FIG. 13C) response to multiple epitopes. Antigens tested include IGFBP-2 peptides (grey bars), CMV positive control (black bars), and media only (white bars). Data are expressed as the mean and standard deviation of IFN-γ-secreting spots for six replicates; *, ** denote p<0.05 and p<0.005 versus spots obtained from media only wells.

FIG. 15A: IGFBP-2 ELISA of sera from pre- and post-vaccinated mice (6-8 mice/group). Lines indicate the mean level of IGFBP-2-specific IgG pre- and post-vaccine. FIG. 15B: T cell responses specific for the vaccinated IGFBP-2 peptides and IGFBP-2 protein were identified in IFNγ ELISPOT using splenocytes from vaccinated mice. Columns represent the mean spots for six replicates. Bars indicate SD; ** denote P<0.005 versus spots obtained from media-only wells. FIG. 15C: Shown are tumor measurements from mice injected with IGFBP-2 peptide vaccines (●), tetanus toxoid peptide (▼), adjuvant alone (▲), or PBS (■). Each data point represents the mean tumor measurement±SD from 8-10 mice. FIG. 15D: Shown is tumor growth for mice treated with IGFBP-2 peptide-specific T cells (▲) or naïve splenocytes (■) 10 days following tumor challenge. Each data point represents the mean tumor measurement±SD from 5 mice.

FIG. 26A-D. Antigen-specific T cell responses (spots per 200,000 cells) to media, tetanus, myoglobin, IGF1R peptide mix, IGF1R and PHA are plotted for control, tamoxifen control, vaccine and tamoxifen+vaccine conditions.

FIG. 27A-F. Bar graphs indicating immunologic signals for control, tamoxifen control, vaccine and tamoxifen+vaccine conditions. CD4, FIG. 27A; FoxP3 (relative expression to CD4), FIG. 27B; CD8, FIG. 27C; granzymeB, FIG. 27D; IFN-γ, FIG. 27E; and perforin, FIG. 27F.

DETAILED DESCRIPTION OF THE INVENTION

Figure 1:
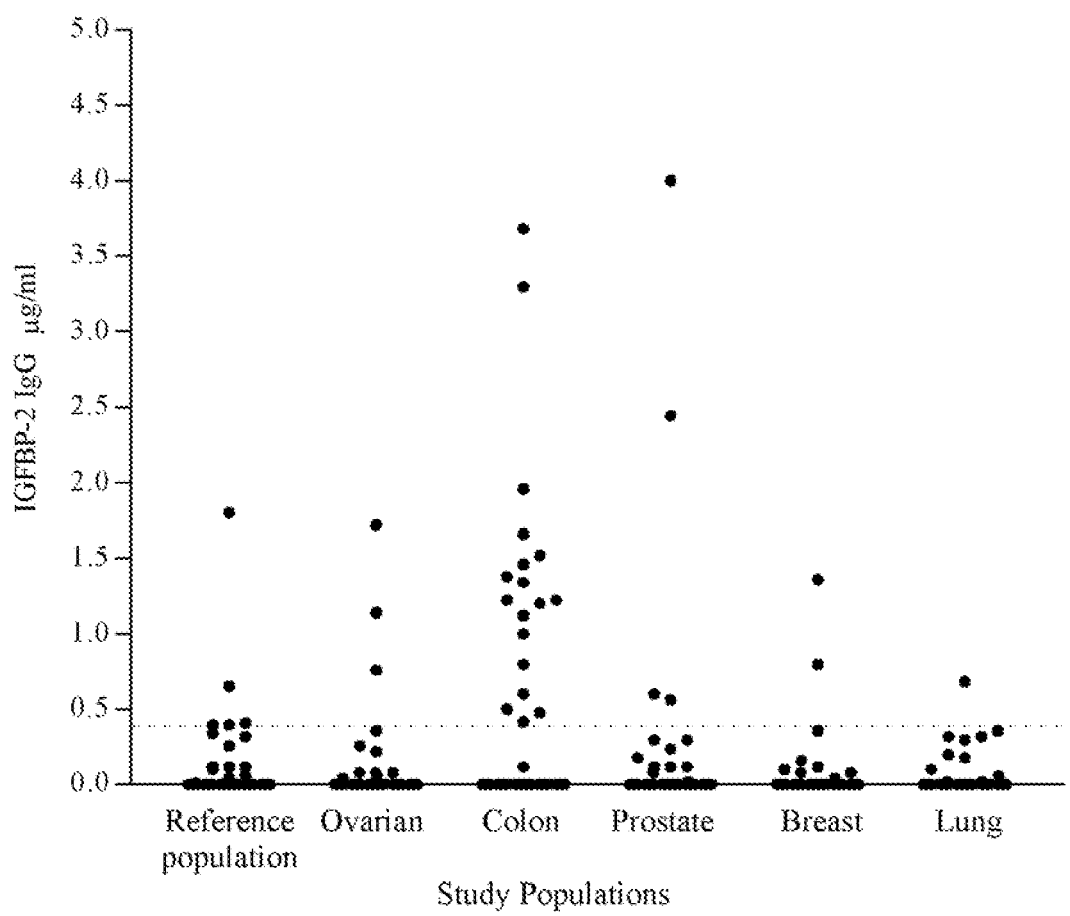
FIG. 1. Antibody immunity to IGFBP-2 can be detected in patients with several common malignancies. Shown are the IGFBP-2-specific IgG concentrations in μg/ml determined for the reference population (n=200) as well as patients with ovarian cancer (n=39), colon cancer (n=42), prostate cancer (n=38), colon cancer (n=42), and non-small cell lung cancer (n=36). Each closed circle represents the concentration determined from serum of an individual subject. The dotted line shows the mean plus three standard deviations of the IgG concentrations determined for the reference control population (0.47 μg/ml) and used to define positive responses in the individual populations.

The present invention is based on the discovery that IGF-related molecules, namely IGFBP-2 and IGF1R, are immunogenic in various human cancers. More specifically, human cancer patients exhibit antibody immunity directed against these molecules. The invention provides select immunogenic peptides derived from these IGF-related molecules that can be used as cancer vaccines. The IGF-related molecules of the invention provide a novel target for treatment and detection of cancer. This invention thus provides IGF-related molecules as diagnostic and therapeutic agents for the detection, monitoring and treatment of various cancers.

The present invention goes beyond merely correlating overexpression of IGF-related molecules to the incidence of various cancers to establish its significance as tumor marker and mediator of malignancy. Rather, the present invention uses antigen-specific IgG immunity to identify proteins that can serve as biologically relevant tumor antigens. The present invention contemplates using antibody immunity against tumor-associated proteins (i.e., production of auto-antibodies against self-antigens) for diagnostic and therapeutic applications, as well as T cell responses for therapy.

Malignancies associated with IGFBP-2 over-expression include, but are not limited to, colon cancers, prostate cancers, and ovarian cancers. Malignancies associated with IGF1R over-expression include, but are not limited to, breast cancers and ovarian cancers. Over-expression of IGFBP-2/IGF1R and related proteins could result from gene amplifications and/or unregulated gene expression. The association of amplified IGFBP-2 or IGF1R gene with a malignancy does not require that the protein expression product of the gene be continuously maintained at elevated levels. For example, over-expression of the protein expression product could be involved in the pathogenesis of a tumor, but the protein over-expression may subsequently subside.

DEFINITIONS

All scientific and technical terms used in this application have meanings commonly used in the art unless otherwise specified. As used in this application, the following words or phrases have the meanings specified.

As used herein, "polypeptide" includes proteins, fragments of proteins, and peptides, whether isolated from natural sources, produced by recombinant techniques or chemically synthesized. Peptides of the invention typically comprise at least about 6 amino acids.

As used herein, "IGF related molecule" includes IGFBP-2 and IGF1R polypeptides, polynucleotides encoding IGFBP-2 and IGF1R polypeptides, polynucleotides complementary to those encoding IGF polypeptides, antibodies that specifically recognize and bind IGFBP-2 and IGF1R polypeptides, as described herein.

As used herein, "biological activity of an IGF-related molecule" refers to the specific binding of an IGF-related molecule to a corresponding binding partner, such as a receptor or antibody, to the expression of an IGF-related polynucleotide, and to the growth regulatory effects of IGF related molecules.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, a polynucleotide "operably encodes" a protein, polypeptide or peptide if it contains an expression control sequence operably linked to the coding sequence.

The term "nucleic acid" or "polynucleotide" refers to a deoxyribonucleotide or ribonucleotide polymer in either single- or double-stranded form, and unless otherwise limited, encompasses known analogs of natural nucleotides that hybridize to nucleic acids in a manner similar to naturally-occurring nucleotides.

As used herein, "antigen-presenting cell" or "APC" means a cell capable of handling and presenting antigen to a lymphocyte. Examples of APCs include, but are not limited to, macrophages, Langerhans-dendritic cells, follicular dendritic cells, B cells, monocytes, fibroblasts and fibrocytes. Dendritic cells are a preferred type of antigen presenting cell. Dendritic cells are found in many non-lymphoid tissues but can migrate via the afferent lymph or the blood stream to the T-dependent areas of lymphoid organs. In non-lymphoid organs, dendritic cells include Langerhans cells and interstitial dendritic cells. In the lymph and blood, they include afferent lymph veiled cells and blood dendritic cells, respectively. In lymphoid organs, they include lymphoid dendritic cells and interdigitating cells.

As used herein, "modified" to present an epitope refers to antigen-presenting cells (APCs) that have been manipulated to present an epitope by natural or recombinant methods. For example, the APCs can be modified by exposure to the isolated antigen, alone or as part of a mixture, peptide loading, or by genetically modifying the APC to express a peptide that includes one or more epitopes.

As used herein, "tumor protein" is a protein that is expressed by tumor cells. Proteins that are tumor proteins also react detectably within an immunoassay (such as an ELISA) with antisera from a patient with cancer.

An "immunogenic peptide," as used herein is a portion of a protein that is recognized (i.e., specifically bound) by a B-cell and/or T-cell surface antigen receptor. Such immunogenic peptides generally comprise at least 5 amino acid residues, more preferably at least 10 amino acid residues of a protein associated with cancer. Typically, an immunogenic peptide comprises 15 to 18 amino acid residues. In some embodiments, immunogenic peptides include peptides in which an N-terminal leader sequence and/or transmembrane domain have been deleted. Other immunogenic peptides may contain a small N- and/or C-terminal deletion (e.g., 1-30 amino acids, preferably 5-15 amino acids), relative to the mature protein.

As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline.

Compositions comprising such carriers are formulated by well known conventional methods (see, for example, *Remington's Pharmaceutical Sciences,* 18th edition, A. Gennaro, ed., Mack Publishing Co., Easton, Pa., 1990).

As used herein, "adjuvant" includes those adjuvants commonly used in the art to facilitate an immune response. Examples of adjuvants include, but are not limited to, helper peptide; aluminum salts such as aluminum hydroxide gel (alum) or aluminum phosphate; Freund's Incomplete Adjuvant and Complete Adjuvant (Difco Laboratories, Detroit, Mich.); Merck Adjuvant 65 (Merck and Company, Inc., Rahway, N.J.); AS-2 (Smith-Kline Beecham); QS-21 (Aquila Biopharmaceuticals); MPL or 3d-MPL (Corixa Corporation, Hamilton, Mont.); LEIF; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A; muramyl tripeptide phosphatidyl ethanolamine or an immunostimulating complex, including cytokines (e.g., GM-CSF or interleukin-2, -7 or -12) and immunostimulatory DNA sequences. In some embodiments, such as with the use of a polynucleotide vaccine, an adjuvant such as a helper peptide or cytokine can be provided via a polynucleotide encoding the adjuvant.

As used herein, "a" or "an" means at least one, unless clearly indicated otherwise.

Polynucleotides of the Invention

The invention provides polynucleotides that encode one or more an IGF-related peptides, such as peptides comprising the amino acid sequences listed herein, or a portion or other variant thereof. Preferred polynucleotides comprise at least 15 consecutive nucleotides, preferably at least 30 consecutive nucleotides and more preferably at least 45 consecutive nucleotides, that encode an IGF-related peptide. Polynucleotides that are fully complementary to any such sequences are also encompassed by the present invention. Polynucleotides may be single-stranded (coding or antisense) or double-stranded, and may be DNA (genomic, cDNA or synthetic) or RNA molecules. RNA molecules include siRNA (discussed below), HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials. Portions of such IGF-related polynucleotides can be useful as primers and probes for the amplification and detection of IGF related molecules in tissue specimens.

Polynucleotides may comprise a native sequence (i.e., an endogenous sequence that encodes an IGF-related polypeptide or a portion thereof) or may comprise a variant of such a sequence. Polynucleotide variants contain one or more substitutions, additions, deletions and/or insertions such that the immunogenicity of the encoded polypeptide is not diminished, relative to a native IGF-related protein. Variants preferably exhibit at least about 80% identity, more preferably at least about 90% identity and most preferably at least about 95% identity to a polynucleotide sequence that encodes a native IGF-related protein or a portion thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 Methods in Enzymology vol. 183, Academic Press, Inc., San Diego, Calif.; Higgins, D. G. and Sharp, P. M. (1989) CABIOS 5:151-153; Myers, E. W. and Muller W. (1988) CABIOS 4:11-17; Robinson, E. D. (1971) Comb. Theor. 11:105; Santou, N., Nes, M. (1987) Mol. Biol. Evol. 4:406-425; Sneath, P. H. A. and Sokal, R. R. (1973) Numerical Taxonomy the Principles and Practice of Numerical Taxonomy, Freeman Press, San Francisco, Calif.; Wilbur, W. J. and Lipman, D. J. (1983) Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native IGF-related protein (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Polynucleotides may be prepared using any of a variety of techniques known in the art. DNA encoding an IGF-related protein may be obtained from a cDNA library prepared from tissue expressing a corresponding protein mRNA. Accordingly, human an IGF-related DNA can be conveniently obtained from a cDNA library prepared from human tissue. The IGF-related protein-encoding gene may also be obtained from a genomic library or by oligonucleotide synthesis. Libraries can be screened with probes (such as antibodies to an IGF-related protein or oligonucleotides of at least about 20-80 bases) designed to identify the gene of interest or the protein encoded by it. Screening the cDNA or genomic library with the selected probe may be conducted using standard procedures, such as those described in Sambrook et al., *Molecular Cloning: A Laboratory Manual* (New York: Cold Spring Harbor Laboratory Press, 1989). An alternative means to isolate the gene encoding an IGF-related protein is to use PCR methodology (Sambrook et al., supra; Dieffenbach et al., *PCR Primer: A Laboratory Manual* (Cold Spring Harbor Laboratory Press, 1995)).

The oligonucleotide sequences selected as probes should be sufficiently long and sufficiently unambiguous that false positives are minimized. The oligonucleotide is preferably labeled such that it can be detected upon hybridization to DNA in the library being screened. Methods of labeling are well known in the art, and include the use of radiolabels, such as $^{32}$P-labeled ATP, biotinylation or enzyme labeling. Hybridization conditions, including moderate stringency and high stringency, are provided in Sambrook et al., supra.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., DNA 2:183, 1983). Alternatively, RNA molecules may be generated by in vitro or in vivo transcription of DNA sequences encoding an IGF-related protein, or portion thereof, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo (e.g., by transfecting antigen-presenting cells, such as dendritic cells, with a cDNA construct encoding an IGF-related polypeptide, and administering the transfected cells to the patient).

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Nucleotide sequences can be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and to permit expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

For oligonucleotide vaccines described herein, a typical embodiment includes a plasmid DNA vaccine. An example of plasmid DNA vaccines targeting self tumor antigens, including the effective use of soluble cytokines as adjuvants for such vaccines, is described in Disis et al., 2003, Immunology 207: 1-8. The teaching therein, involving use of the intracellular domain (ICD) of HER-2/neu as the antigen, can be adapted for use with IGF-related vaccines of the invention.

Antisense and Inhibitory Nucleic Acid Molecules

The antisense molecules of the present invention comprise a sequence substantially complementary, or preferably fully complementary, to all or a fragment of an IGF-related gene. Included are fragments of oligonucleotides within the coding sequence of an IGF-related gene, and inhibitory nucleotides that inhibit the expression of an IGF-related protein. Antisense oligonucleotides of DNA or RNA complementary to sequences at the boundary between introns and exons can be employed to prevent the maturation of newly-generated nuclear RNA transcripts of specific genes into mRNA for transcription. Antisense RNA, including siRNA, complementary to specific genes can hybridize with the mRNA for that gene and prevent its translation. The antisense molecule can be DNA, RNA, or a derivative or hybrid thereof. Examples of such derivative molecules include, but are not limited to, peptide nucleic acid (PNA) and phosphorothioate-based molecules such as deoxyribonucleic guanidine (DNG) or ribonucleic guanidine (RNG).

Antisense RNA can be provided to the cell as "ready-to-use" RNA synthesized in vitro or as an antisense gene stably transfected into cells which will yield antisense RNA upon transcription. Hybridization with mRNA results in degradation of the hybridized molecule by RNAse H and/or inhibition of the formation of translation complexes. Both result in a failure to produce the product of the original gene.

Both antisense RNA and DNA molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro or in vivo transcription of DNA sequences encoding the antisense RNA molecule. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

DNA molecules may be modified to increase intracellular stability and half-life. Possible modifications include, but are not limited to, the addition of flanking sequences of the 5' and/or 3' ends of the molecule or the use of phosphorothioate or 2' O-methyl rather than phosphodiesterase linkages within the backbone of the molecule. Other modifications include the use of chimeric antisense compounds. Chimeric antisense compounds of the invention may be formed as composite structures of two or more oligonucleotides, modified oligonucleotides, oligonucleosides and/or oligonucleotide mimetics. Such compounds have also been referred to in the art as hybrids or gapmers. Representative U.S. patents that teach the preparation of such hybrid structures include, but are not limited to, U.S. Pat. Nos. 5,700,922 and 6,277,603.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Antisense compositions of the invention include oligonucleotides formed of homopyrimidines that can recognize local stretches of homopurines in the DNA double helix and bind to them in the major groove to form a triple helix. See: Helen, C and Toulme, J J. Specific regulation of gene expression by antisense, sense, and antigene nucleic acids. Biochem. Biophys Acta, 1049:99-125, 1990. Formation of the triple helix would interrupt the ability of the specific gene to undergo transcription by RNA polymerase. Triple helix formation using myc-specific oligonucleotides has been observed. See: Cooney, M, et al. Science 241:456-459.

Antisense sequences of DNA or RNA can be delivered to cells. Several chemical modifications have been developed to prolong the stability and improve the function of these molecules without interfering with their ability to recognize specific sequences. These include increasing their resistance to degradation by DNases, including phosphotriesters, methylphosphonates, phosphorothioates, alpha-anomers, increasing their affinity for binding partners by covalent linkage to various intercalating agents such as psoralens, and increasing uptake by cells by conjugation to various groups including polylysine. These molecules recognize specific sequences encoded in mRNA and their hybridization prevents translation of and increases the degradation of these messages.

Antisense compositions including oligonucleotides, derivatives and analogs thereof, conjugation protocols, and antisense strategies for inhibition of transcription and translation are generally described in: Antisense Research and Applications, Crooke, S. and B. Lebleu, eds. CRC Press, Inc. Boca Raton Fla. 1993; Nucleic Acids in Chemistry and Biology Blackburn, G. and M. J. Gait, eds. IRL Press at Oxford University Press, Inc. New York 1990; and Oligonucleotides and Analogues: A Practical Approach Eckstein, F. ed., IRL Press at Oxford University Press, Inc. New York 1991; which are each hereby incorporated herein by reference including all references cited therein which are hereby incorporated herein by reference.

IGF-Related Polypeptides

IGFBP-2/IGF1R polypeptides as described herein may be of any length suitable for the intended use. In some embodiments, immunization with one or more IGF-related peptides is preferred, while in other embodiments, immunization with full-length protein is preferred. The peptides may be of any length, although peptides are typically at least 6 amino acids in length. Lengths of 10, 15, 20, 25, 30, 50 and 100 amino acids are contemplated in addition to full-length protein.

Additional sequences derived from the native protein and/or heterologous sequences may be present, and such sequences may, but need not, possess further ligand binding, immunogenic or antigenic properties. One example of heterologous sequence that may be particularly suitable for use in a cancer vaccine is one or more cancer-associated immunogenic peptides capable of eliciting anti-cancer immunity. In addition to including multiple peptides derived from IGFBP-2 and/or IGF1R as described herein, one could include other known cancer-related immunogenic peptides, such as HER-2/neu. For example, for the treatment of ovarian cancer, a vaccine comprising a combination of IGFBP-2 peptides and CA-125 peptides could be administered to the patient. For the treatment of prostate cancer, a vaccine comprising a combination of IGFBP-2 and HER-2/neu peptides could be administered to the patient.

Preferred peptides comprise the sequences of amino acid residues set forth in the tables and figures herein. Adjacent native sequence is not necessary, but small portions (less than 15 additional amino acid residues, preferably less than 10 additional amino acid residues) of adjacent sequence can be used without interfering with the immunogenicity of the peptide or its ease of delivery. Those skilled in the art will appreciate that other portions or variants thereof will be useful in the treatment and detection of cancer.

Immunogenic peptides may generally be identified using well known techniques, such as those summarized in Paul, Fundamental Immunology, 4th ed., 663-665 (Lippincott-Raven Publishers, 1999) and references cited therein. Such techniques include screening peptides for the ability to react with antigen-specific antibodies, antisera and/or T-cell lines or clones. As used herein, antisera and antibodies are antigen-specific if they specifically bind to an antigen (i.e., they react with the protein in an ELISA or other immunoassay, and do not react detectably with unrelated proteins). Such antisera and antibodies may be prepared using well known techniques. An immunogenic peptide can be a portion of a native protein that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length polypeptide. Such screens may generally be performed using methods well known to those of ordinary skill in the art, such as those described in Harlow and Lane, Antibodies: A Laboratory Manual, Cold Spring Harbor Laboratory, 1988. For example, a peptide may be immobilized on a solid support and contacted with patient sera to allow binding of antibodies within the sera to the immobilized peptide. Unbound sera may then be removed and bound antibodies detected using, for example, $^{125}$I-labeled Protein A.

A polypeptide "variant" of IGFBP-2/IGF1R, as used herein, is a polypeptide that differs from a native IGFBP-2/IGF1R protein in one or more substitutions, deletions, additions and/or insertions, such that the immunogenicity of the polypeptide is not substantially diminished. In other words, the ability of a variant to react with antigen-specific antisera may be enhanced or unchanged, relative to the native protein, or may be diminished by less than 50%, and preferably less than 20%, relative to the native protein. Such variants may generally be identified by modifying one of the above polypeptide sequences and evaluating the reactivity of the modified polypeptide with antigen-specific antibodies or antisera as described herein. Preferred variants include those in which one or more portions, such as an N-terminal leader sequence, have been removed. Other preferred variants include variants in which a small portion (e.g., 1-30 amino acids, preferably 5-15 amino acids) has been removed from the N- and/or C-terminal of the mature protein. Polypeptide variants preferably exhibit at least about 70%, more preferably at least about 90% and most preferably at least about 95% identity (determined as described above) to the identified polypeptides. In the context of IGFBP-2 and IGF1R peptides of the invention, such variations in the sequence are typically outside of the 15 amino acid residues identified herein as responsible for the immunogenic effect.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

Polypeptides may comprise a signal (or leader) sequence at the N-terminal end of the protein that co-translationally or post-translationally directs transfer of the protein. The polypeptide may also be conjugated to a linker or other sequence for ease of synthesis, purification or identification of the polypeptide (e.g., poly-FEs), or to enhance binding of the polypeptide to a solid support. For example, a polypeptide may be conjugated to an immunoglobulin Fc region.

In some embodiments, the peptides are purified from the same subject to whom the composition will be administered. In these embodiments, it may be desirable to increase the number of tumor cells. Such a scale up of cells could be performed in vitro or in vivo, using, for example, a SCID mouse system. Where the cells are scaled up in the presence of non-human cells, such as by growing a human subject's tumor in a SCID mouse host, care should be taken to purify the human cells from any non-human (e.g., mouse) cells that may have infiltrated the tumor. In these embodiments in which the composition will be administered to the same subject from whom the peptides are purified, it may also be desirable purify several IGFBP-2/IGF1R peptides to optimize the efficacy of a limited quantity of starting material.

Recombinant peptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, yeast, insect cells or a mammalian cell line such as COS or CHO. Supernatants from suitable host/vector systems that secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having fewer than about 100 amino acids, and generally fewer than about 50 amino acids, may also be generated by synthetic means, using techniques well known to those of ordinary skill in the art. For example, such peptides may be synthesized using any of the commercially available solid-phase techniques, such as the Merrifield solid-phase synthesis method, where amino acids are sequentially added to a growing amino acid chain. See Merrifield, J. Am. Chem. Soc. 85:2149-2146, 1963. Equipment for automated synthesis of peptides is commercially available from suppliers such as Perkin Elmer/Applied BioSystems Division (Foster City, Calif.), and may be operated according to the manufacturers instructions.

Peptides can be synthesized on a Perkin Elmer/Applied Biosystems Division 430A peptide synthesizer using FMOC chemistry with HPTU (O-BenzotriazoleN,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid: ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%-60% acetonitrile (containing 0.1% TFA) in water may be used to elute the peptides. Following lyophilization of the pure fractions, the peptides may be characterized using electrospray or other types of mass spectrometry and by amino acid analysis.

Fusion Proteins

In some embodiments, the polypeptide is a fusion protein that comprises multiple peptides as described herein, or that comprises at least one peptide as described herein and an unrelated sequence. In some embodiments, the fusion protein comprises a IGFBP-2/IGF1R peptide and an immunogenic peptide. The immunogenic peptide can comprise, for example, all or a portion of an additional tumor protein.

Additional fusion partners can be added. A fusion partner may, for example, serve as an immunological fusion partner by assisting in the provision of T helper epitopes, preferably T helper epitopes recognized by humans. As another example, a fusion partner may serve as an expression enhancer, assisting in expressing the protein at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the peptide components may be assembled separately, and ligated into an appropriate expression vector. The 3' end of the DNA sequence encoding one peptide component is ligated, with or without a peptide linker, to the 5' end of a DNA sequence encoding the second peptide component so that the reading frames of the sequences are in phase. This permits translation into a single fusion protein that retains the biological activity of both component peptides.

A peptide linker sequence may be employed to separate the first and the second peptide components by a distance sufficient to ensure that each peptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second peptides; and (3) the lack of hydrophobic or charged residues that might react with the peptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39-46, 1985; Murphy et al., Proc. Natl. Acad. Sci. USA 83:8258-8262, 1986; U.S. Pat. No. 4,935,233 and U.S. Pat. No. 4,751,180. The linker sequence may generally be from 1 to about 50 amino acids in length. Linker sequences are not required when the first and second peptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located 5' to the DNA sequence encoding the first peptides. Similarly, stop codons required to end translation and transcription termination signals are present 3' to the DNA sequence encoding the second peptide.

Fusion proteins are also provided that comprise a peptide of the present invention together with an unrelated immunogenic protein. Preferably the immunogenic protein is capable of eliciting a memory response. Examples of such proteins include tetanus, tuberculosis and hepatitis proteins (see, for example, Stoute et al., New Engl. J. Med. 336:86-91, 1997).

Within preferred embodiments, an immunological fusion partner is derived from protein D, a surface protein of the gram-negative bacterium *Haemophilus influenza* B (WO 91/18926). Preferably, a protein D derivative comprises approximately the first third of the protein (e.g., the first N-terminal 100-110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS I (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; Gene 43:265-292, 1986). LYTA is an autolysin that specifically degrades certain bonds in the peptidoglycan backbone. The C-terminal domain of the LYTA protein is responsible for the affinity to the choline or to some choline analogues such as DEAR This property has been exploited for the development of *E. coli* C-LYTA expressing plasmids useful for expression of fusion proteins. Purification of hybrid proteins containing the C-LYTA fragment at the amino terminus has been described (see Biotechnology 10:795-798, 1992). Within a preferred embodiment, a repeat portion of LYTA may be incorporated into a fusion protein. A repeat portion is found in the C-terminal region starting at residue 178. A particularly preferred repeat portion incorporates residues 188-305.

In general, polypeptides (including fusion proteins) and polynucleotides as described herein are isolated. An "isolated" polypeptide or polynucleotide is one that is removed from its original environment. For example, a naturally occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Antibodies

The term "antibody" includes single anti-IGFBP-2/IGF1R monoclonal antibodies (including agonist, antagonist and neutralizing antibodies) and anti-IGFBP-2/IGF1R antibody compositions with polyepitopic specificity. The term "monoclonal antibody" (mAb) as used herein refers to an antibody obtained from a population of substantially homogeneous antibodies, i.e. the antibodies comprising the individual population are identical except for possible naturally-occurring mutations that may be present in minor amounts.

The invention provides antibodies that bind to IGFBP-2/IGF1R proteins and polypeptides. The most preferred antibodies will specifically bind to a IGFBP-2/IGF1R protein and will not bind (or will bind weakly) to non-IGFBP-2/IGF1R proteins and polypeptides. Anti-IGFBP-2/IGF1R antibodies that are particularly contemplated include monoclonal and polyclonal antibodies as well as fragments containing the antigen binding domain and/or one or more complementarity determining regions of these antibodies. As used herein, an antibody fragment is defined as at least a portion of the variable region of the immunoglobulin molecule that binds to its target, i.e., the antigen binding region.

IGFBP-2/IGF1R antibodies of the invention may be particularly useful in cancer diagnostic and prognostic assays, and imaging methodologies. Intracellularly expressed antibodies (e.g., single chain antibodies) may be therapeutically useful in treating cancers in which the expression of IGFBP-2/IGF1R is involved. Also useful in therapeutic methods for treatment of cancer are systemically administered IGFBP-2/IGF1R antibodies that interfere with IGFBP-2/IGF1R function or that target cells expressing IGFBP-2/IGF1R for delivery of a toxin or therapeutic molecule. Such delivery of a toxin or therapeutic molecule can be achieved using known methods of conjugating a second molecule to the IGFBP-2/IGF1R antibody or fragment thereof.

The invention also provides various immunological assays useful for the detection and quantification of IGFBP-2/IGF1R peptides. Such assays generally comprise one or more IGFBP-2/IGF1R antibodies capable of recognizing and binding a IGFBP-2/IGF1R, and may be performed within various immunological assay formats well known in the art, including but not limited to various types of radioimmunoassays, enzyme-linked immunosorbent assays (ELISA), enzyme-linked immunofluorescent assays (ELIFA), and the like. In addition, immunological imaging methods capable of detecting cancers expressing IGFBP-2/IGF1R are also provided by the invention, including but not limited to radioscintigraphic imaging methods using labeled IGFBP-2/IGF1R antibodies. Such assays may be clinically useful in the detection, monitoring, and prognosis of IGFBP-2/IGF1R expressing cancers.

Various methods for the preparation of antibodies are well known in the art. For example, antibodies may be prepared by immunizing a suitable mammalian host using a IGFBP-2/IGF1R protein, peptide, or fragment, in isolated or immunoconjugated form (Antibodies: A Laboratory Manual, CSH Press, Eds., Harlow, and Lane (1988); Harlow, Antibodies, Cold Spring Harbor Press, NY (1989)). In addition, fusion proteins of IGFBP-2/IGF1R may also be used, such as a IGFBP-2/IGF1R GST-fusion protein. In another embodiment, a IGFBP-2/IGF1R peptide may be synthesized and used as an immunogen.

The antibodies or fragments may also be produced, using current technology, by recombinant means. Regions that bind specifically to the desired regions of the IGFBP-2/IGF1R protein can also be produced in the context of chimeric or CDR grafted antibodies of multiple species origin. Humanized or human IGFBP-2/IGF1R antibodies may also be produced and are preferred for use in therapeutic contexts. Methods for humanizing murine and other non-human antibodies by substituting one or more of the non-human antibody CDRs for corresponding human antibody sequences are well known (see for example, Jones et al., 1986, Nature 321: 522-525; Riechmann et al., 1988, Nature 332: 323-327; Verhoeyen et al., 1988, Science 239: 1534-1536). See also, Carter et al., 1993, Proc. Natl. Acad. Sci. USA 89: 4285 and Sims et al., 1993, J. Immunol. 151: 2296. Methods for producing fully human monoclonal antibodies include phage display and transgenic methods (for review, see Vaughan et al., 1998, Nature Biotechnology 16: 535-539).

Fully human IGFBP-2/IGF1R monoclonal antibodies may be generated using cloning technologies employing large human Ig gene combinatorial libraries (i.e., phage display) (Griffiths and Hoogenboom, Building an in vitro immune system: human antibodies from phage display libraries. In: Protein Engineering of Antibody Molecules for Prophylactic and Therapeutic Applications in Man. Clark, M. (Ed.), Nottingham Academic, pp 45-64 (1993); Burton and Barbas, Human Antibodies from combinatorial libraries. Id., pp 65-82). Fully human IGFBP-2/IGF1R monoclonal antibodies may also be produced using transgenic mice engineered to contain human immunoglobulin gene loci as described in PCT Patent Application WO98/24893, Kucherlapati and Jakobovits et al., published Dec. 3, 1997 (see also, Jakobovits, 1998, Exp. Opin. Invest. Drugs 7(4): 607-614). This method avoids the in vitro manipulation required with phage display technology and efficiently produces high affinity authentic human antibodies.

Reactivity of IGFBP-2/IGF1R antibodies with a IGFBP-2/IGF1R protein may be established by a number of well known means, including western blot, immunoprecipitation, ELISA, and FACS analyses using, as appropriate, IGFBP-2/IGF1R proteins, peptides, IGFBP-2/IGF1R-expressing cells or extracts thereof.

A IGFBP-2/IGF1R antibody or fragment thereof of the invention may be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. A second molecule for conjugation to the IGFBP-2/IGF1R antibody can be selected in accordance with the intended use. For example, for therapeutic use, the second molecule can be a toxin or therapeutic agent. Further, bi-specific antibodies specific for two or more IGFBP-2/IGF1R epitopes may be generated using methods generally known in the art. Homodimeric antibodies may also be generated by cross-linking techniques known in the art (e.g., Wolff et al., Cancer Res. 53: 2560-2565).

T Cells

Immunotherapeutic compositions may also, or alternatively, comprise T cells specific for a IGFBP-2/IGF1R peptide. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the ISOLEX™ magnetic cell selection system, available from Nexell Therapeutics, Irvine, Calif. (see also U.S. Pat. No. 5,536,475); or MACS cell separation technology from Miltenyi Biotec, including Pan T Cell Isolation Kit, CD4+ T Cell Isolation Kit, and CD8+ T Cell Isolation Kit (see also U.S. Pat. No. 5,240,856; U.S. Pat. No. 5,215,926; WO 89/06280; WO 91/16116 and WO 92/07243). Alternatively, T cells may be derived from related or unrelated humans, non-human mammals, cell lines or cultures.

T cells may be stimulated with a IGFBP-2/IGF1R peptide, polynucleotide encoding a IGFBP-2/IGF1R peptide and/or an antigen presenting cell (APC) that expresses such a IGFBP-2/IGF1R peptide. The stimulation is performed under conditions and for a time sufficient to permit the generation of T cells that are specific for the peptide. Preferably, a IGFBP-2/IGF1R peptide or polynucleotide is present within a delivery vehicle, such as a microsphere, to facilitate the generation of specific T cells.

T cells are considered to be specific for a IGFBP-2/IGF1R peptide if the T cells kill target cells coated with the peptide or expressing a gene encoding the peptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., Cancer Res. 54:1065-1070, 1994.

Detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a IGFBP-2/IGF1R protein (100 ng/ml-100 µg/ml, preferably 200 ng/ml-25 µg/ml) for 3-7 days should result in at least a two fold increase in proliferation of the T cells. Contact as described above for 2-3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998)). T cells that have been activated in response to a IGFBP-2/IGF1R peptide, polynucleotide or peptide-expressing APC may be CD4+ and/or CD8+. T cells can be expanded using standard techniques.

Within preferred embodiments, the T cells are derived from either a patient or a related, or unrelated, donor and are administered to the patient following stimulation and expansion. For therapeutic purposes, CD4+ or CD8+ T cells that proliferate in response to a IGFBP-2/IGF1R peptide, polynucleotide or APC can be expanded in number either in vitro or in vivo. Proliferation of such T cells in vitro may be accomplithed in a variety of ways. For example, the T cells can be re-exposed to a IGFBP-2/IGF1R peptide, with or without the addition of T cell growth factors, such as interleukin-2, and/or stimulator cells. Alternatively, one or more T cells that proliferate in the presence of a IGFBP-2/IGF1R peptide can be expanded in number by cloning. Methods for cloning cells are well known in the art, and include limiting dilution.

Pharmaceutical Compositions and Vaccines

The invention provides IGFBP-2/IGF1R polypeptides, polynucleotides, T cells and/or antigen presenting cells that are incorporated into pharmaceutical compositions, including immunogenic compositions (i.e., vaccines). Pharmaceutical compositions comprise one or more such compounds and, optionally, a physiologically acceptable carrier. In a typical embodiment, the composition includes multiple IGF-related peptides of the invention, delivered either in polypeptide form, or as a polynucleotide encoding multiple IGF-related peptides. Vaccines may comprise one or more such compounds and an adjuvant that serves as a non-specific immune response enhancer.

The adjuvant may be any substance that enhances an immune response to an exogenous antigen. Examples of adjuvants include conventional adjuvants, biodegradable microspheres (e.g., polylactic galactide), immunostimulatory oligonucleotides and liposomes (into which the compound is incorporated; see e.g., Fullerton, U.S. Pat. No. 4,235,877). Vaccine preparation is generally described in, for example, M. F. Powell and M. J. Newman, eds., "Vaccine Design (the subunit and adjuvant approach)," Plenum Press (NY, 1995). Pharmaceutical compositions and vaccines within the scope of the present invention may also contain other compounds that may be biologically active or inactive. For example, one or more immunogenic portions of other tumor antigens may be present, either incorporated into a fusion polypeptide or as a separate compound, within the composition or vaccine.

A pharmaceutical composition or vaccine can contain DNA encoding one or more of the peptides as described herein, such that the polypeptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, Crit. Rev. Therap. Drug Carrier Systems 15:143-198, 1998, and references cited therein. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerin) that expresses an immunogenic portion of the polypeptide on its cell surface or secretes such an epitope.

In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., Proc. Natl. Acad. Sci. USA 86:317-321, 1989; Flexner et al., Ann. N. Y. Acad Sci. 569:86-103, 1989; Flexner et al., Vaccine 8:17-21, 1990; U.S. Pat. Nos. 4,603,112, 4,769,330, and 5,017,487; WO 89/01973; U.S. Pat. No. 4,777,127; GB 2,200,651; EP 0345242; WO 91/02805; Berkner-Biotechniques 6:616-627, 1988; Rosenfeld et al., Science 252:431-434, 1991; Kolls et al., Proc. Natl. Acad. Sci. USA 91:215-219, 1994; Kass-Eisler et al., Proc. Natl. Acad. Sci. USA 90:11498-11502, 1993; Guzman et al., Circulation 88:2838-2848, 1993; and Guzman et al., Cir. Res. 73:1202-1207, 1993. Techniques for incorporating DNA into such expression systems are well known to those of ordinary skill in the art. The DNA may also be "naked," as described, for example, in Ulmer et al., Science 259:1745-1749, 1993 and reviewed by Cohen, Science 259:1691-1692, 1993. The uptake of naked DNA may be increased by coating the DNA onto biodegradable beads, which are efficiently transported into the cells, and other means known to those skilled in the art.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous, intradermal or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release, or absorption or penetration across the blood-brain barrier of the IGFBP-2/IGF1R related molecule. Such excipients are those substances usually and customarily employed to formulate dosages for parenteral administration in either unit dose or multi-dose form or for direct infusion into the CSF by continuous or periodic infusion from an implanted pump.

Such compositions may also comprise buffers (e.g., neutral buffered saline or phosphate buffered saline), carbohydrates (e.g., glucose, mannose, sucrose or dextrans), mannitol, proteins, peptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

Any of a variety of adjuvants may be employed in the vaccines of this invention. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); aluminum salts such as aluminum hydroxide gel (alum) or aluminum phosphate; salts of calcium, iron or zinc; an insoluble suspension of acylated tyrosine acylated sugars; cationically or anionically derivatized polysaccharides; polyphosphazenes biodegradable microspheres; monophosphoryl lipid A and quit A. Cytokines, such as GM CSF or interleukin-2, -7, or -12, may also be used as adjuvants.

Within the vaccines provided herein, the adjuvant composition is preferably designed to induce an immune response predominantly of the Th1 type. High levels of Th1-type cytokines (e.g., IFN-α, IL-2 and IL-12) tend to favor the induction of cell mediated immune responses to an administered antigen. In contrast, high levels of Th2-type cytokines (e.g., IL-4, IL-5, IL-6, IL-10 and TNF-β) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, Ann. Rev. Immunol. 7:145-173, 1989.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site, such as a site of surgical excision of a tumor. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Antigen Presenting Cells

Any of a variety of delivery vehicles may be employed within pharmaceutical compositions and vaccines to facilitate production of an antigen-specific immune response that targets tumor cells. Delivery vehicles include antigen presenting cells (APCs), such as dendritic cells, macrophages, B cells, monocytes and other cells that may be engineered to be efficient APCs.

Such cells may, but need not, be genetically modified to increase the capacity for presenting the antigen, to improve activation and/or maintenance of the T cell response, to have anti-tumor or anti-infective effects per se and/or to be immunologically compatible with the receiver (i.e., matched BLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Bancherau and Steinman, Nature 392:245-251, 1998) and have been shown to be effective as a physiological adjuvant for eliciting prophylactic or therapeutic antitumor immunity (see Timmerman and Levy, Ann. Rev. Med. 50:507-529, 1999). In general, dendritic cells may be identified based on their typical shape (stellate in situ, with marked cytoplasmic processes (dendrites) visible in vitro) and based on the lack of differentiation markers of B cells (CD19 and CD20), T cells (CD3), monocytes (CD14) and natural killer cells (CD56), as determined using standard assays. Dendritic cells may, of course, be engineered to express specific cell surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., Nature Med. 4:594-600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor, mannose receptor and DEC-205 marker. The mature phenotype is typically characterized by a lower expression of these markers, but a high expression of cell surface molecules responsible for T cell activation such as class I and class II NMC, adhesion molecules (e.g., CD54 and CD11) and costimulatory molecules (e.g., CD40, CD80 and CD86).

APCs may generally be transfected with a polynucleotide encoding one or more IGFBP-2/IGF1R peptides such that the IGFBP-2/IGF1R peptide, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., Immunology and Cell Biology 75:456-460, 1997. Antigen loading of dendritic cells may be achieved by incubating dendritic cells or progenitor cells with the IGFBP-2/IGF1R peptide, DNA (naked or within a plasmid vector) or RNA; or with antigen-expressing recombinant bacterium or viruses (e.g., vaccinia, fowlpox, adenovirus or lentivirus vectors). Prior to loading, the peptide may be covalently conjugated to an immunological partner that provides T cell help (e.g., a carrier molecule). Alternatively, a dendritic cell may be pulsed with a non-conjugated immunological partner, separately or in the presence of the peptide.

Therapeutic and Prophylactic Methods

Treatment includes prophylaxis and therapy. Prophylaxis or therapy can be accomplished by a single direct injection at a single time point or multiple time points to a single or multiple sites. Administration can also be nearly simultaneous to multiple sites. Patients or subjects include mammals, such as human, bovine, equine, canine, feline, porcine, and ovine animals. The subject is preferably a human.

A cancer may be diagnosed using criteria generally accepted in the art, including the presence of a malignant tumor. Pharmaceutical compositions and vaccines may be administered either prior to or following surgical removal of primary tumors and/or treatment such as administration of radiotherapy or conventional chemotherapeutic drugs.

Within certain embodiments, immunotherapy may be active immunotherapy, in which treatment relies on the in vivo stimulation of the endogenous host immune system to react against tumors or infected cells with the administration of immune response-modifying agents (such as peptides and polynucleotides disclosed herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as CD8+cytotoxic T lymphocytes and CD4+ T-helper tumor-infiltrating lymphocytes), killer cells (such as Natural Killer cells and lymphokine-activated killer cells), B cells and antigen-presenting cells (such as dendritic cells and macrophages) expressing a peptide provided herein. In a preferred embodiment, dendritic cells are modified in vitro to present the peptide, and these modified APCs are administered to the subject. T cell receptors and antibody receptors specific for the peptides recited herein may be cloned, expressed and transferred into other-vectors or effector cells for adoptive immunotherapy. The peptides provided herein may also be used to generate antibodies or anti-idiotypic antibodies (as described above and in U.S. Pat. No. 4,918,164) for passive immunotherapy.

Administration and Dosage

The compositions are administered in any suitable manner, often with pharmaceutically acceptable carriers. Suitable methods of administering cells in the context of the present invention to a subject are available, and, although more than one route can be used to administer a particular cell composition, a particular route can often provide a more immediate and more effective reaction than another route.

The dose administered to a patient, in the context of the present invention, should be sufficient to effect a beneficial therapeutic response in the patient over time, or to inhibit disease progression. Thus, the composition is administered to a subject in an amount sufficient to elicit an effective immune response to the specific antigens and/or to alleviate, reduce, cure or at least partially arrest symptoms and/or complications from the disease. An amount adequate to accomplish this is defined as a "therapeutically effective dose."

Routes and frequency of administration of the therapeutic compositions disclosed herein, as well as dosage, will vary from individual to individual, and may be readily established using standard techniques. In general, the pharmaceutical compositions and vaccines may be administered, by injection (e.g., intracutaneous, intratumoral, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. In one embodiment, 2 intradermal injections of the composition are administered 10 days apart.

A suitable dose is an amount of a compound that, when administered as described above, is capable of promoting an anti-tumor immune response, and is at least 10-50% above the basal (i.e., untreated) level. Such response can be monitored, for example, by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to nonvaccinated patients. In general, for pharmaceutical compositions and vaccines comprising one or more peptides, the amount of each peptide present in a dose ranges from about 0.01 µg/kg to about 100 mg/kg body weight will be administered by intradermal, subcutaneous, or intravenous route. A preferred dosage is about 1 µg/kg to about 1 mg/kg, with about 5 µg/kg to about 200 µg/kg particularly preferred.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a tumor protein generally correlate with an improved clinical outcome. Such immune responses may generally be evaluated using standard proliferation, cytotoxicity or cytokine assays, which may be performed using samples obtained from a patient before and after treatment.

Diagnostic Methods

The invention provides methods for detecting IGFBP-2 and/or IGF1R specific IgG immunity (i.e., production of anti-IGFBP-2 or IGF1R antibodies by activated B cells having specificity for IGFBP-2 or IGF1R), to be used as a clinical marker for malignancies associated with IGFBP-2/IGF1R over-expression. The detection of such autologous antibodies (i.e., auto-antibodies) raised endogenously against clinically relevant, tumor-associated proteins such as IGFBP-2 and/or IGF1R are useful in the development of sensitive diagnostic assays or tests. Serologic methods of analysis, by specifically focusing on IgG antibody immunity, could offer tremendous advantages by: (1) permitting rapid and high through-put screening of large numbers of sera to determine incidence of immunity; and (2) biasing antigen identification such that proteins most likely to elicit cell-mediated immunity are selected. A serologic screening method could be utilized to determine whether IGFBP-2/IGF1R immunity is detectable in patients suspected with any type of cancer involving IGFBP-2/IGF1R over-expression, which includes ovarian, colon, breast and prostate cancers. The assessment of antibody immunity is quite different from taking direct measurement of the protein level itself, in that antibody immunity could be used: (1) to indicate exposure to a tumor-associated protein (i.e., the existence of immunogenic protein); and (2) to achieve higher sensitivity levels for the detection of small amounts of the immunogenic protein.

Those skilled in the art will appreciate additional variations suitable for the method of detecting cancer in tissue through detection of a IGFBP-2/IGF1R molecule in a specimen. This method can also be used to monitor IGFBP-2/IGF1R levels in tissue of a patient undergoing treatment for cancer. The suitability of a IGFBP-2/IGF1R-targeted therapeutic regimen for initial or continued treatment can be determined by monitoring IGFBP-2/IGF1R levels using this method.

One embodiment of the present invention relates to methods for the detection of malignancies associated with the over-expression of IGFBP-2/IGF1R and related proteins, in a warm-blooded animal. These methods may be used on a one time basis when a malignancy is suspected or on a periodic basis (e.g., to monitor an individual with an elevated risk of acquiring or reacquiring a malignancy). Antibodies specific (i.e., exhibiting a binding affinity of about IO.sup.7 liters/mole or better) for IGFBP-2/IGF1R protein could be found in a variety of bodily fluids including sera and ascites fluid. Bodily fluids that are suspected of containing antibodies specific for IGFBP-2/IGF1R protein are combined with the IGFBP-2/IGF1R protein, and incubated for a duration and under conditions that are sufficient for the formation of immunocomplexes (e.g., 4° C. for 24-48 hrs). Following the incubation, the reaction mixture is tested for the presence of immunocomplexes. Detection of one or more immunocomplexes formed between IGFBP-2/IGF1R and antibodies specific for IGFBP-2/IGF1R protein may be accomplished by a variety of known techniques, such as radioimmunoassays (RIA) and enzyme linked immunosorbent assays (ELISA).

Suitable immunoassays include the double monoclonal antibody sandwich immunoassay technique of David et al. (U.S. Pat. No. 4,376,110); monoclonal-polyclonal antibody sandwich assays (Wide et al., in Kirkham and Hunter, eds., Radioimmunoassay Methods, E. and S. Livingstone, Edinburgh, 1970); the "western blot" method of Gordon et al. (U.S. Pat. No. 4,452,901); immunoprecipitation of labeled ligand (Brown et al., J. Biol. Chem. 255:4980-4983, 1980); enzyme-linked immunosorbent assays as described by, for example, Raines and Ross (J. Biol. Chem. 2575 154-5160, 1982); immunocytochemical techniques, including the use of fluorochromes (Brooks et al., Clin. Exp. Immunol. 39:477, 1980); and neutralization of activity [Bowen-Pope et al., Proc. Natl. Acad. Sci. USA 81:2396-2400 (1984)], all of which are hereby incorporated by reference. In addition to the immunoassays described above, a number of other immunoassays are available, including those described in U.S. Pat. Nos. 3,817,827; 3,850,752; 3,901,654; 3,935,074; 3,984,533; 3,996,345; 4,034,074; and 4,098,876, all of which are herein incorporated by reference.

For detection purposes, IGFBP-2/IGF1R protein ("antigen") may either be labeled or unlabeled. When unlabeled, the antigen could be used in agglutination assays. In addition, unlabeled antigen could be used in combination with labeled molecules that are reactive with immunocomplexes, or in combination with labeled antibodies (second antibodies) that are reactive with the antibody directed against the IGFBP-2/IGF1R protein. Alternatively, the antigen could be directly labeled with reporter groups such as radioisotopes, fluorophores, enzymes, luminescers, or dye particles. These and other labels are well known in the art and are described, for example, in the following U.S. Pat. Nos. 3,766,162; 3,791,932; 3,817,837; 3,996,345; and 4,233,402. Typically in an ELISA assay, the reporter group could be chosen from a variety of enzymes, including horseradish peroxidase, beta-galactosidase, alkaline phosphatase, and glucose oxidase.

In one embodiment, a reporter group is bound to IGFBP-2/IGF1R protein. The step of detecting immunocomplexes involves removing substantially any unbound IGFBP-2/IGF1R protein and then detecting the presence or absence of the reporter group. In another embodiment, a reporter group is bound to a second antibody capable of binding to the antibodies specific for the IGFBP-2/IGF1R protein. The detection of immunocomplex formation involves the steps: (a) removing substantially any unbound antibody; (b) adding the second antibody; (c) removing substantially any unbound second antibody; and then (d) detecting the presence or absence of the reporter group. Where the antibody specific for IGFBP-2/IGF1R protein is derived from a human, the second antibody is an anti-human antibody.

In another embodiment for detecting immunocomplexes, a reporter group is bound to a molecule capable of binding to the immunocomplexes. The detection involves the steps: (a) adding the molecule, (b) removing substantially any unbound molecule, and then (c) detecting the presence or absence of the reporter group. An example of a molecule capable of binding to the immunocomplexes is protein A. It will be evident to one skilled in the art that a variety of methods for detecting the immunocomplexes could be employed within the present invention. Reporter groups suitable for use in these methods include radioisotopes, fluorophores, enzymes, luminescers, and dye particles.

In one embodiment, prior exposure of a warm-blooded animal such as humans to the IGFBP-2/IGF1R protein could be detected by testing for the presence or absence of specific activation of CD4+ or CD8+ T cells. More specifically, T cells isolated from an individual by routine techniques (e.g., Ficoll/Hypaque density gradient centrifugation of peripheral blood lymphocytes) could be incubated with the IGFBP-2/IGF1R protein. For example, T cells may be incubated in vitro for 2-9 days (typically 4 days) at 37° C. with IGFBP-2/IGF1R protein (typically, 5 μg/ml of whole protein or 25 μg/ml of an appropriate peptide or graded numbers of cells synthesizing IGFBP-2/IGF1R protein). It may be desirable to incubate another aliquot of a T cell sample in the absence of IGFBP-2/IGF1R protein to serve as a control.

Specific activation of CD4+ or CD8+ T cells could be detected in a variety of ways. Methods for detecting specific T cell activation include detecting the proliferation of T cells, the production of cytokines (e.g., lymphokines), or the generation of cytolytic activity (i.e., generation of cytotoxic T cells specific for IGFBP-2/IGF1R protein). For CD4+ T cells, a preferred method for detecting specific T cell activation is the detection of the proliferation of T cells. For CD8+ T cells, a preferred method for detecting specific T cell activation is the detection of the generation of cytolytic activity.

Detection of the proliferation of T cells may be accomplished by a variety of known techniques. For example, T cell proliferations could be detected by measuring the rate of DNA synthesis. T cells that have been stimulated to proliferate exhibit an increased rate of DNA synthesis. A typical way to measure the rate of DNA synthesis is, for example, by pulse-labeling cultures of T cells with tritiated thymidine, a nucleoside precursor which is incorporated into newly synthesized DNA. The amount of tritiated thymidine incorporated could be determined using a liquid scintillation spectrophotometer. Other ways to detect T cell proliferation include measuring increases in interleukin-2 (IL-2) production, $Ca^{2+}$ flux, or dye uptake, such as 3-(4,5-dimethylthiazol-2-yl)-2,5-diphenyl-tetrazolium. Alternatively, synthesis of lymphokines (such as interferon-gamma) could be measured or the relative number of T cells that are able to respond to native IGFBP-2/IGF1R protein or peptides thereof, could be sufficient.

Kits

For use in the diagnostic and therapeutic applications described herein, kits are also within the scope of the invention. Such kits can comprise a carrier, package or container that is compartmentalized to receive one or more containers such as vials, tubes, and the like, each of the container(s) comprising one of the separate elements to be used in the method. For example, the container(s) can comprise a probe that is or can be detectably labeled. The probe can be an antibody or polynucleotide specific for a IGFBP-2/IGF1R protein or a IGFBP-2/IGF1R gene or message, respectively. The kit can also include containers containing nucleotide(s) for amplification of a target nucleic acid sequence and/or a container comprising a reporter-means, such as a biotin-binding protein, e.g., avidin or streptavidin, bound to a detectable label, e.g., an enzymatic, florescent, or radioisotope label. The kit can include all or part of the amino acid sequence of FIG. 2, or a nucleic acid molecule that encodes such amino acid sequences.

The kit of the invention will typically comprise the container described above and one or more other containers comprising materials desirable from a. commercial and user standpoint, including buffers, diluents, filters, needles, syringes, and package inserts with instructions for use. In addition, a label can be provided on the container to indicate that the composition is used for a specific therapeutic or non-therapeutic application, and can also indicate directions for either in vivo or in vitro use, such as those described above. Directions and or other information can also be included on an insert which is included with the kit.

EXAMPLES

The following examples are presented to illustrate the present invention and to assist one of ordinary skill in making and using the same. The examples are not intended in any way to otherwise limit the scope of the invention.

Example 1

Insulin-Like Growth Factor Binding Protein 2 is a Human Solid Tumor Antigen

This example demonstrates serologic methods that were used to prospectively determine that IGFBP-2 is a human tumor antigen. IGFBP-2 is overexpressed in many human malignancies and the overexpression of the protein is related to the malignant potential of the cancer cell. We hypothesize that proteins useful for evaluation as cancer vaccine candidates would be those that were immunogenic in cancer patients and important to the maintenance or evolution of the malignant phenotype.

Serum Samples.

Between 1994 and 2001, sera was collected from both cancer patients and a reference population and stored in aliquots at −70° C. The experimental patient population was heterogeneous in terms of type and stage of malignancy (breast=40, ovarian=39, prostate=38, colorectal=42 and non-small cell lung cancers=36). All subjects gave informed consent authorizing blood sample collection for assessment of anti-tumor immune responses. The reference population sera was derived from volunteer donors, n=200, who had donated blood products at the Puget Sound Blood Center (Seattle, Wash.). The age-range of this reference group was 18-72 years (106 males, 94 females).

IGFBP-2 Reagents.

The cDNA encoding human IGFBP-2 was cloned into the eukaryotic expression plasmid, pcDNA4/HisMax B (Invitrogen, Carlsbad, Calif.) in frame with and downstream of a polyhistidine ((His)$_6$) tag to create the fusion construct, pCDHis-IGFBP-2. Chinese hamster cells (CHO) were then transfected with the parental vector or the pCDHis-IGFBP-2 construct (Effective reagent, Qiagen), and stable transfectants were selected. CHO cells transfected with the pCDHis-IGFBP-2 (CHO/His-IGFBP-2) or the vector control (CHO/His) were maintained in culture in RMPI medium supplemented with 10% FCS and 150 μg/ml zeocin (Invitrogen). Cell lysates were prepared from cells harvested during log-phase growth. Specifically, cells were washed, centrifuged, and incubated in a lysate buffer consisting of Tris base (0.6%), NaCl (0.88%), and Triton-X (10%), supplemented with aprotinin (1 μg/ml), benzamidine (1 mM/L), and phenylmethylsulfonyl fluoride (1 mM/mL). After incubation on ice for 60 minutes, insoluble material was pelleted and the supernatant was aliquoted and stored at −70° C. prior to use. Protein concentration was determined and standardized by Coomassie G-250 staining (BioRad Protein Assay, Bio-Rad Laboratories, Hercules, Calif.), and the IGFBP-2 protein identity confirmed for each lot by Western blot analysis.

Immunoprecipitation and Western Blot Analysis.

The IGFBP-2 protein was immunoprecipitated from CHO/His-IGFBP-2 cells using either a murine IGFBP-2-specific monoclonal antibody (Diagnostic Systems Laboratories, Webster, Tex.) or human sera by standard methods. Immunoprecipitates were then resolved on 12.5% SDS-PAGE gels and electrophoretically transferred to nitrocellulose membranes. After blocking, nitrocellulose membranes were then incubated for 1 hour with either a goat IGFBP-2-specific polyclonal antibody (Santa Cruz Biotechnology, Santa Cruz, Calif.) or a murine IGFBP-2-specific monoclonal antibody (Diagnostic Systems Laboratories), washed, and then probed with an appropriate peroxidase-conjugated detection antibody (Zymed, San Francisco, Calif.). After washing, the membranes were developed with chemiluminescent reagent (ECL, Amersham Pharmacia) and exposed to x-ray film. Recombinant human IGFBP-2 (Research Diagnostics, Inc, Flanders, N.J.) served as a positive control.

Enzyme-Linked Immunosorbant Assay (ELISA) for the Detection of Human 1GFBP-2 IgG Antibodies.

IgG antibodies recognizing IGFBP-2 were detected by a capture ELISA method. Experimental and control wells of 96-well lmmulon 4HBX microtiter plates (Dynex Technologies, Inc., Chantilly, Va.) were coated with a murine monoclonal antibody against the polyhistidine epitope (#34460 Penta-Li Ab, Qiagen Inc, Valencia, Calif.) in 50 mM sodium carbonate buffer (pH 9.6), and incubated overnight at 4° C. Additional wells on each plate were coated with purified human IgG (range 0.62-0.00025 μg/ml) (Sigma Chemical Co. St. Louis, Mo.) to provide a reference standard curve. All wells were then blocked with PBS containing 5% bovine serum albumin (BSA) (Sigma), and incubated at room temperature for 8 hours. Plates were washed and then 0.4 μg of CHO/His lysate (control wells) or CHO/His-IGFBP-2 lysate (experimental wells) were added to each well. Plates were incubated overnight at 4° C., washed and probed with patient sera added to wells at dilutions of 1:25, 1:50, 1:100, 1:200. Control serum from a colon cancer patient with high levels of IGFBP-2 antibody, documented by Western blot, was used as a positive control on each plate. After a 2-hour incubation at room temperature, plates were washed and IgG antibodies were detected with a peroxidase-conjugated goat anti-human IgG antibody (Zymed Laboratories). Following a 45-minute incubation at room temperature, the plates were washed and developed with tetramethylbenzidine (TMB) peroxidase substrate (Kierkegard and Perry Laboratories, Gaithersburg, Md.) according to the manufacturers instructions. The optical densities (OD) of the reactions were monitored at 640 nm, stopped with addition of HCl, and read at 450 nm. The ΔOD of each serum dilution was calculated as the OD of the CHO/His-IGFBP-2 lysate-coated wells minus the OD of the corresponding CHO/His lysate-coated wells. A reference IgG concentration was determined for each sample based on the standard log-log curve generated on each plate with the known concentrations of human IgG. A positive ELISA result was defined as an IgG concentration greater than the mean plus 3 standard deviations of the reference population at a 1:25 dilution. Positive responses by ELISA assay were confirmed by Western blot analysis. The accuracy of the assay was determined by 20 replicate runs of purified human IgG. The calculated correlation coefficient was 0.99 calculated from a plot of expected vs. assayed values and the assay had a mean coefficient of variation (CV) of 10%. The intra-assay and inter-assay precision was determined by multiple runs (n=20) of sera from a colon cancer patient. The intra-assay CV was 11%, and the inter-assay CV was 14%. Linearity of the assay was defined with a correlation coefficient of 0.975. All data was analyzed and calculations made with SOFTmax version 2.3 for Macintosh (Molecular Devices Corp., Sunnyvale, Calif.).

Statistical Analysis.

A Fisher's exact test was used to test the homogeneity of the IgG prevalence rates in the cancer and normal sera populations. An abnormal level of expression was defined as 3 standard deviations above the mean of normal sample expression (0.47 μg/ml).

Antibody Immunity to IGFBP-2 can be Detected in Patients with Several Common Malignancies.

Two hundred sera specimens were obtained from male and female volunteer blood donors without cancer and screened for evidence of IgG antibody responses specific for IGFBP-2 by ELISA to establish a reference range. The mean antibody response in this reference population was 0.026 μg/ml with a standard deviation of 0.148 μg/ml. A positive antibody response was defined as an IGFBP-2 IgG concentration greater than the mean plus 3 standard deviations of this reference population, or 0.47 μg/ml. Two volunteer blood donors (1%) had antibody immunity to IFGBP-2, a 44-year old male had an IGFBP-2-specific IgG concentration of 1.8 μg/ml and a 42-year old female had an IgG concentration of 0.65 μg/ml. These responses were verified by Western blot analysis. Sera derived from patients with ovarian, colon, prostate, breast and non-small cell lung cancer were then assessed for the presence of IGFBP-2 specific IgG antibodies (FIG. 1). The range of responses in patients with ovarian cancer was 0-1.72 μg/ml, colon cancer patients was 0-3.68 μg/ml, prostate cancer patients was 0-4.0 μg/ml, breast cancer patients was 0-1.36 μg/ml, and in non-small cell lung cancer patients was 0-0.68 μg/ml.

Patients with Colorectal Cancer have the Highest Prevalence of IgG Immunity to IGFBP-2.

Figure 2:
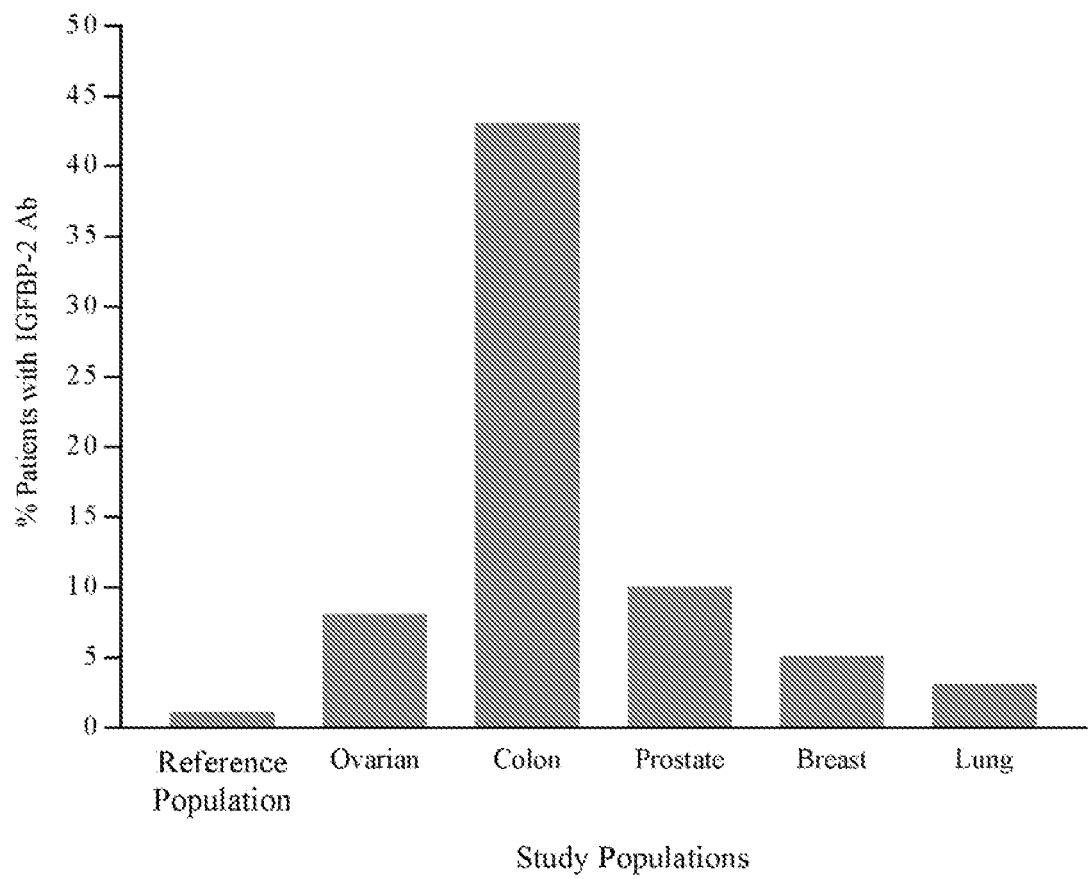
FIG. 2. Patients with colorectal cancer have the highest prevalence of IgG immunity to IGFBP-2. Shown are the prevalence rates of IGFBP-2 IgG antibody immunity in the study populations. Data are shown as the % of each populations with detectable IGFBP-2 specific antibodies.

FIG. 2 depicts the overall prevalence of IGFBP-2-specific IgG antibody immunity in the patient and reference populations tested. The prevalence of IGFBP-2 IgG-specific immunity was low and not statistically different from the reference population in subjects with breast cancer (5%, p=0.13) and non-small cell lung cancer (3%, p=0.39). However, the detection of IGFBP-2 antibody immunity was significantly different from controls in patients with colorectal cancer (41%, p=0.0001), prostate cancer (11%, p=0.007), and ovarian cancer (8%, p=0.032).

Figure 3:
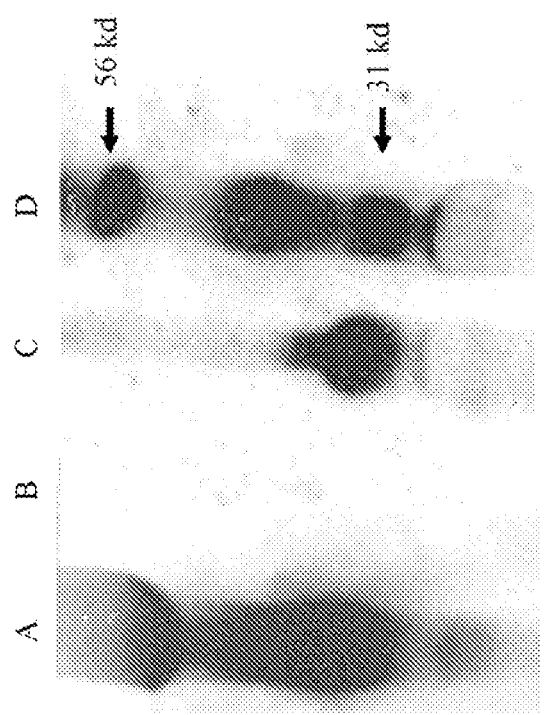
FIG. 3. Antibodies in patients' sera detected by ELISA are able to immunoprecipitate IGFBP-2 protein from cell lysates. IGFBP-2 protein was immunoprecipitated from a CHO/His-IGFBP-2 lysate using a monoclonal antibody specific for IGFBP-2 (A), sera from a patient with breast cancer and no IGFBP-2-specific IgG response by ELISA (B), or sera from a patient with prostate cancer and IGFBP-2 specific IgG immunity detected by ELISA (C). Immunoprecipitates were resolved using SDS-PAGE and IGFBP-2 was detected by western blot using an IGFBP-2-specific polyclonal antibody. The arrows indicate the migration of standard molecular weight markers (D).

FIG. 3 demonstrates that sera obtained from a patient with prostate cancer with an IGFBP-2 antibody IgG concentration of 4.0 μg/ml can bind to and precipitate IGFBP-2 (FIG. 3C). Similar results could be obtained with a monoclonal antibody specific for the protein (FIG. 3A). Sera from a breast cancer patient with no detectable antibodies to IGFBP-2 by ELISA was not able to immunoprecipitate the protein from solution (FIG. 3B). No sera immunoprecipitated protein from CHO/His control cell lysates not expressing IGFBP-2.

IGFBP-2 is overexpressed in several common tumors and is associated with a more aggressive malignant phenotype. Studies correlating IGFBP-2 expression with poor clinical outcome indicate a potential role of the protein in the growth and evolution of certain cancers. For example, increased levels of IGFBP-2 are associated with the change from hormone dependence to independence in breast and prostate cancer. Therefore, eradication of IGFBP-2 overexpressing cells may result in halting the progression of disease or altering the pathogenesis of particular malignancies. An immune response targeting IGFBP-2 may result in tumor stasis or destruction. Cancer vaccines specific for IGFBP-2 might stimulate such an immune response, however, it must first be determined whether IGFBP-2 is immunogenic in patients with cancer, i.e. a tumor antigen. We utilized a serologic screening method to discern whether IGFBP-2 was immunogenic in humans. Serologic methods of analysis, specifically focusing on IgG antibody immunity, permit rapid and high through-put screening of large numbers of sera to determine incidence of immunity and will also bias antigen identification to those proteins most likely eliciting cell mediated immunity. Studies presented here demonstrate that IGFBP-2 immunity is detectable in patients with ovarian, colon, and prostate cancers as compared to volunteer blood donors.

The mechanism by which overexpression of IGFBP-2 contributes to the progression of human cancer is not well understood. However, clinical investigations suggest overexpression of IGFBP-2 is a mediator of the malignant potential of the cell, and support the development of immune-based strategies targeting IGFBP-2. Association has been made between abundance of IGFBP-2 protein, either in tumor or sera, and a poor clinical outcome in several cancer types. (12) In the studies described here, patients with colon cancer had the highest incidence of antibody immunity directed against IGFBP-2. Overexpression and secretion of IGFBP-2 has been well described in colorectal tumors. A recent prospective analysis of patients with and without colon cancer demonstrated that elevated serum levels of IGFBP-2 were directly associated with the presence of colonic neoplasia. (13) Furthermore, immunohistochemical analysis was performed on malignant tissue derived from those patients with colon cancer and demonstrated that IGFBP-2 protein expression was markedly elevated in cancer cells as compared to adjacent benign epithelium. Additional investigations have also shown the overexpression of insulin like growth factor receptor 2 (IGF-2) in colon cancer is associated with tumor progression and decreased overall survival. (14) Circulating levels of IGFBP-2 protein have been extensively evaluated in patients with prostate cancer. A study of over 100 patients with prostate cancer demonstrated that levels of serum IGFBP-2 protein were elevated in patients as compared to volunteer controls (p<0.006). (15) Amplification of both of these genes in prostate cancer tissues from 24 patients was correlated with the presence of lymph node metastasis and more aggressive pathologic stage. (16) Finally the IGF system has been shown to be critical in regulating follicular development in the ovary and unregulated growth in cancer. Levels of circulating IGFBP-2 have been evaluated in patients with ovarian cancer where they have been found to be significantly elevated over controls. (17) Indeed, elevated levels of IGFBP-2 correlated with levels of CA-125, an established tumor marker for ovarian cancer. Moreover, increased levels of IGFBP-2 protein as well as gene amplification have been identified in malignant ovaries and malignant ovarian cysts. (18, 19)

We have used the detection of antigen specific IgG immunity to identify proteins that could serve as biologically relevant tumor antigens. However, antibody immunity may also be useful as a clinical marker of disease status. Circulating IGFBP-2 protein has been evaluated as a tumor marker, as well as a marker to identify patients at risk of developing cancer, although circulating serum tumor associated proteins are most often correlated to tumor burden. In a recent study, circulating levels of IGFBP-2 protein have not been found to be useful as a diagnostic tool in assessing risk of prostate cancer. (20) Antibody immunity to tumor-associated proteins may be a more appropriate serologic measure of cancer exposure. The assessment of an antibody immune response to a protein is quite different from the direct measurement of the protein itself in that antibody immunity can be detected even when small amounts of the immunogenic protein are present and can indicate exposure to tumor related protein. Antibody responses mounted to clinically relevant tumor related proteins, such as IGFBP-2, may be a more sensitive diagnostic tool than direct measurement of shed tumor proteins.

Investigations within the last decade have resulted in the identification of multiple tumor antigens in a variety of different tumor types. Many of these antigens are shared between tumors allowing the potential for the development of multi-antigen vaccines for the treatment of common solid tumors. IGFBP-2 may be an ideal component for such a vaccine since the protein is immunogenic in patients with cancer and may mediate malignant cell growth in common tumors.

REFERENCES CITED

1. Boon, T., et al., Immunol Today. 18: 267-8, 1997.
2. Salazar, L. and Disis, M. L. In: H. Stauss and Y. Kawakami (eds.), Tumor Antigens recognized by T cells and antibodies: Harwood Academic Publishers, (in press) 2002.
3. Tureci, O., et al., Hybridoma. 18: 23-28, 1999.
4. Le Naour, F., et al., Clin Cancer Res. 7: 3328-35, 2001.
5. Jager, E., et al., J Exp Med. 187: 265-70, 1998.
6. Nishikawa, H., et al., Proc Natl Acad Sci USA. 98: 14571-6, 2001.
7. Houghton, A. N., J Exp Med. 180: 1-4, 1994.
8. Disis, M. L. and Cheever, M. A. In: F. Alt and P. Marrack (eds.), Current Opinion in Immunology, Vol. 5, pp. 637-642. London: Current Biology Ltd., 1996.
9. Cibotti, R., et al., Proc Natl Acad Sci USA. 89: 416-20, 1992.
10. Nickerson, T., et al., Cancer Res. 61: 6276-80, 2001.
11. Renehan, A. G., et al., J Clin Endocrinol Metab. 85: 3402-8, 2000.
12. Hoeflich, A., et al., Cancer Res. 61: 8601-10, 2001.
13. Miraki-Moud, F., et al., Clin Endocrinol (Oxf). 54: 499-508, 2001.
14. Kawamoto, K., et al., Oncology. 55: 242-8, 1998.
15. Shariat, S. F., et al., J Clin Oncol. 20: 833-41, 2002.
16. Mita, K., et al., Int J Urol. 7: 321-9, 2000.
17. Flyvbjerg, A., et al., J Clin Endocrinol Metab. 82: 2308-13, 1997.
18. Karasik, A., et al., J Clin Endocrinol Metab. 78: 271-6, 1994.
19. Kanety, H., et al., Br J Cancer. 73: 1069-73, 1996.
20. Stattin, P., et al., J Natl Cancer Inst. 92: 1910-7, 2000.

Example 2

IGFBP2 is a Tumor Antigen in Patients with Breast and Ovarian Cancer

This example demonstrates that patients with breast and ovarian cancer have a detectable humoral immune response specific for IGFBP-2. In addition, the example identifies immunogenic "hot spots" in the IGFBP-2 protein, and shows that IGFBP-2 peptide specific CD4+ T cells can respond to protein presented endogenously on autologous antigen presenting cells.

Human Subjects. Serum from 200 donors between ages 18 and 75 years was used to establish a reference interval for antibody to IGFBP-2. Serum samples were obtained from the Puget Sound Blood Bank in Seattle, Wash., and the volunteers met all criteria for blood donation. Control sera were aliquoted and stored at −80° C. Peripheral blood mononuclear cells (PBMCs) were obtained by leukapheresis after informed consent from volunteer donors and breast cancer patients. Cells were ficolled and cryopreserved as previously described in Disis, M. L., et al., J Immunol Methods, 308:13-18, 2006.

Evaluation of humoral immunity specific for IGFBP-2. Immulon 4HBX microtiter plates (Dynex Technologies, Inc., Chantilly, Va.), were coated overnight with 50 µl of highly purified, human recombinant IGFBP-2 protein (Sigma Chemical Co. St. Louis, Mo.) diluted 1/1000 with carbonate buffer to a concentration of 0.5 µg/ml, or carbonate buffer alone in alternating columns. The last column of wells was incubated with serially diluted, purified human IgG (Sigma) to provide a standard curve. The standard curve was prepared by adding purified human IgG titrated to range from 0.62 µg/ml to 0.005 µg/ml, 50 pl/well, to the last column. Plates were blocked with 100 µl 1% BSA/PBS, at room temperature for 1 hour and washed 4 times with PBS/Tween-20. The patient sera was added after dilution with 10% NGS/10% FCS/PBS/1% BSA/25 1:25 through 1:200 and incubated 2 hours at room temperature. Plates were washed 4 times and incubated for 45 minutes at room temperature after addition of 50 µl IgG-HRP conjugate (Zymed) diluted 1:50,000 in buffer. After additional washing, plates were developed with 75 µl TMB reagent (Kirkegaard and Perry Laboratories, Gaithersburg, Md.) and read at 640 nm. Reaction was stopped with 75 µl 1 N HCl when the 0.16 µg/ml standard reached an OD of 0.3, and plates were read at 450 nm. The OD of each serum dilution was calculated as the OD of the protein-coated wells minus the OD of the buffer-coated wells. Values for µg/ml were calculated from the standard curve on each plate, and positive cut-point for the indirect ELISA was set at 0.5 µg/ml (0.026±0.148) based on the value of mean+2SD of 200 volunteer donors.

Scoring system for prediction of the MHC Class II binding epitopes. To identify MHC class II epitopes that have optimal binding affinity and promiscuity across multiple class II alleles, we developed a combined scoring system using widely available algorithms. Previous studies evaluating class I epitope prediction have shown peptides that score highly across more than one algorithm are more likely to be natural epitopes (Lu, J. and Celis, E., Cancer Res, 60:5223-5227, 2000). Furthermore, we have demonstrated that high binding affinity across multiple class II alleles predicted immunogenic human epitopes (Salazar, L. G., et al., Clin Cancer Res, 9:5559-5565, 2003). The following five algorithms were used for evaluation: SYFPEITHI (Institute for Cell Biology, Heidelberg, Germany), Propred (Institute of Microbial Technology, Chandigarh, India), MHC-Thread (University of Aberdeen, Aberdeen, UK), Average Binding matrix method, and Rankpep (Havard medical school, Boston, Mass.). Binding predictions were generated using each algorithm for the 15 most common MHC class II alleles; DRB1*0101, DRB1*1501, DRB1*0301, DRB1*0401, DRB1*0404, DRB1*0405, DRB1*0701, DRB1*0802, DRB1*0901, DRB1*1101, DRB1*1201, DRB1*1302, DRB3*0101, DRB4*0101, DRB5*0101.

The 20 highest predicted binding peptides for each available MHC II allele from the five algorithms were scored on the basis of the rank order of the predicted binding affinity. Each selected peptide sequence was assigned a score between 20 and 1 with the highest ranking sequences receiving score of 20. Then, the scores from each algorithm were summed up (S) and the numbers of MHC class II alleles for which each peptide sequence has high affinity were counted (N). The final scores were calculated by multiplying S and N, and fourteen of the highest ranking 15-mers of peptides were selected.

Evaluation of T cell responses to IGFBP-2 peptides and protein. PBMCs from 10 normal donors and 10 breast cancer patients were assayed for IFNγ production in the presence of 14 IGFBP-2 peptides chosen as described above, CMV lysate as positive control, and media alone. All assays were done in 6 well replicates. Briefly, 96-well nitrocellulose plates (Millititer, Millipore, Bedford, Mass.) were coated overnight at 4° C. with 50 µl/well of 10 µg/ml anti-human IFN-γ monoclonal antibody (clone: 1-D1K, MabTech, Nacka, Sweden) in Dulbecco's Phosphate Buffered Saline (DPBS) (Gibco Invitrogen). The plates were washed 3 times for 5 minutes each with 200 µl DPBS/well and blocked with 100 µl/well of 2% bovine serum albumin in DPBS for 2 hours at room temperature. PBMCs were plated at 250,000 cells per well with 10 µg/ml of IGFBP-2 peptides, 2.5 µg/ml of CMV lysate or media alone in a total volume of 200 µl/well for 96 hours at 37° C. in 5% CO2. The plates were washed with 200 µl of 0.05% Tween™/DPBS. Wells were incubated for 2.5 hours at room temperature using 50 µl of 1 µg/ml anti-IFN-γ (clone: 7-B6-1, MabTech) antibody diluted in 0.05% Tween™/DPBS. After washing three times with PBS, streptavidin-alkaline phosphatase (BioRad, Munich, Germany) was diluted 1/1000 and added at 50 µl/well for 2 hours at room temperature. After another washing step with PBS, 100 µl/well of BCIP/NBT substrate (BioRad) was added for up to 20 minutes. Color development was stopped by washing under running tap water. After drying overnight at room temperature, colored spots were counted using a AID Elispot High-Resolution reader system and AID EliSpot Software version 3.5 (Autoimmun Diagnostika GmbH, Straβberg, Germany). The mean number of spots from the six replicate wells at each dilution was reported for each antigen.

For the ELISPOT assay of the cultured T cell lines, $1 \times 10^5$ of PBMCs, inactivated by irradiation at 3,000 rads, were added to the same number of T cells per well and incubated for 24 hours at 37° C. in 5% CO2. Peptide-specific T cells were assayed for IFNγ production in the presence of serially diluted concentrations of IGFBP-2 peptides (0.01, 0.1, 1, and 10 µg/ml) and IGFBP-2 protein (0.1, 1, 10 µg/ml), 1 µg/ml of PHA as positive control, and HER-2/neu peptide p328-342 and media alone served as negative controls. All assays were done in 6 well replicates.

Reagents used for the generation of T cell lines. T cell media used for T cell expansions consisted of X-Vivo-15 (Biowhittaker, Walkersville, Md.) supplemented with 10% human AB serum (Valley Biomedical, Winchester, Va.), 10 mM acetylcysteine (Faulding, Paramus, N.J.), 20 mM HEPES, 2 mM L-glutamine, 100 µg/ml penicillin and 100 µg/ml streptomycin (Invitrogen, Grand Island, N.Y.). IGFBP-2 peptides were synthesized by Genemed Synthesis Inc. (South San Francisco, Calif.), purified by high-performance liquid chromatography, and characterized by mass spectrometry. Human recombinant interleukin-2 (IL-2) was manufactured by Hoffmann-La Roche (Nutley, N.J.), and used to expand the T cells in vitro. Lyophilized recombinant IL-2 was reconstituted with sterile water and stored at 4° C. A portion of the stock IL-2 was diluted with T cell media before use. Human recombinant interleukin-12 (IL-12) was purchased from R&D System (Minneapolis, Minn.). Lyophilized recombinant IL-12 was reconstituted and into PBS/1% human serum albumin (Bayer, ZLB Bioplasma AG, Berne, Switzerland), aliquoted and stored at −20° C. before use. Anti-CD3/CD28 beads were kindly provided by Xcyte Therapies Corporation (Seattle, Wash.).

Generation of IGFBP-2 specific T cell lines. PBMCs derived from both volunteer donors and cancer patients by leukaphereses were isolated by ficoll hypaque density gradient centrifugation and cryopreserved in liquid nitrogen until use. Cryopreserved PBMC were thawed, washed and resuspended at a concentration of $3\times10^6$ cells/ml in T cell media. The cells were stimulated with 10 μg/ml of various IGFBP-2 peptides and incubated at 3TC in 5% CO2. On days 4 and 8, 3 U/ml of recombinant human IL-2 and 10 ng/ml of recombinant human IL-12 were added to the stimulated cells. On day 12, the stimulated cells were harvested from the culture flasks, and resuspended at a concentration of $1\times10^6$/ml in fresh media containing $1\times10^6$/ml of Xcyte CD3/CD28 beads. The cells and the beads were mixed gently and co-incubated in at 37° C. in 5% $CO_2$. From days 14 to 23, the number of the cells was evaluated every two to three days and the cells were diluted to a concentration of $0.5-1\times10^6$/ml with fresh media. IL-2 was added at a final concentration of 5 U/ml into the cell culture.

Phenotypic analysis of the T cell lines. To phenotype the cultured peptide-specific T cells, four color flow cytometry analysis was performed using the following antibodies (Ab): fluorescein isothiocyanate (FITC)-conjugated anti-CD8, phycoerythrin (PE)-conjugated anti-CD4, PE-Cy5-conjugated CD3, and PE-Cy7-conjugated CD56 (all Abs from Beckman Coulter, Fullerton, Calif.). For extracellular staining, cells were incubated for 30 minutes at room temperature with optimal dilution of each Ab. FACS analysis was performed using Cytomics FC 500 MPL Flow Cytometry System with MXP software (Beckman Coulter, Fullerton, Calif.). Typically, 50,000-100,000 events were collected per sample.

Figure 4:
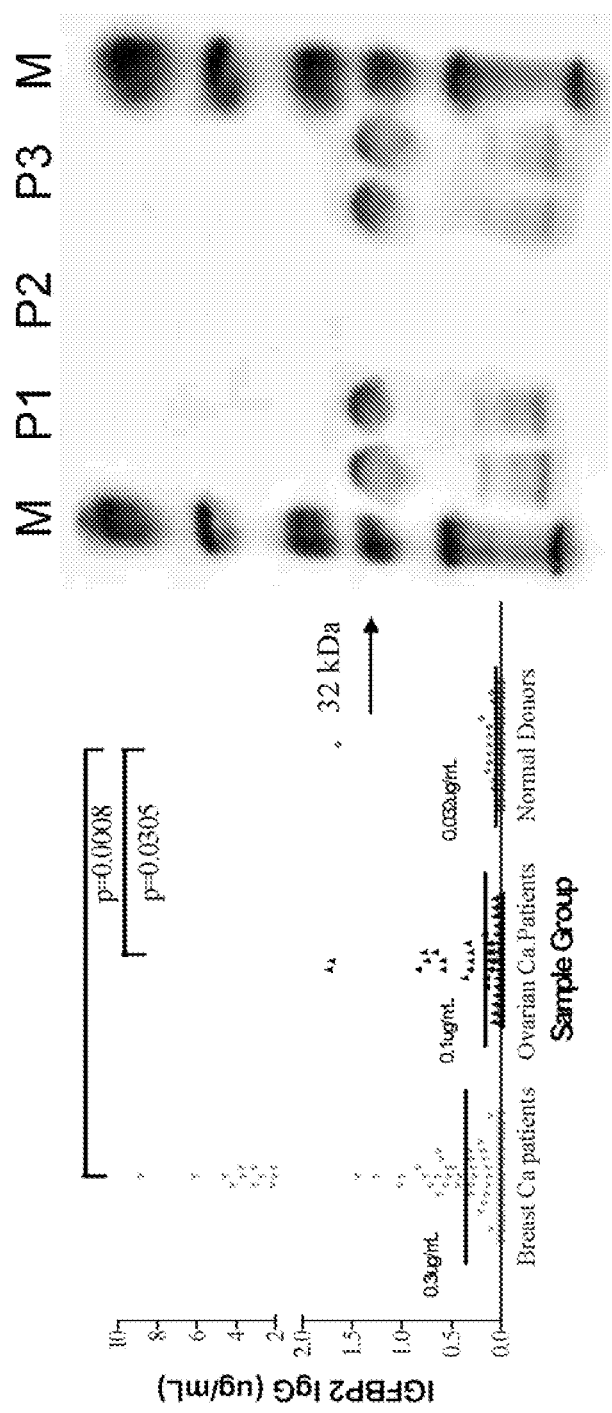
FIG. 4. Patients with breast and ovarian cancer have a detectable humoral immune response specific for IGFBP-2. The amount of antibody detected, measured in μg/ml IGFBP2 IgG, is plotted for breast cancer patients (mean 0.3 μg/ml), ovarian cancer patients (mean 0.1 μg/ml), and normal donors (mean 0.032 μg/ml). Statistical significance: p=0.0008 for breast cancer versus normal and p=0.0305 for ovarian cancer versus normal. Representative blot is displayed at right, with 32 kDa marker indicated with arrow.
Figure 5:
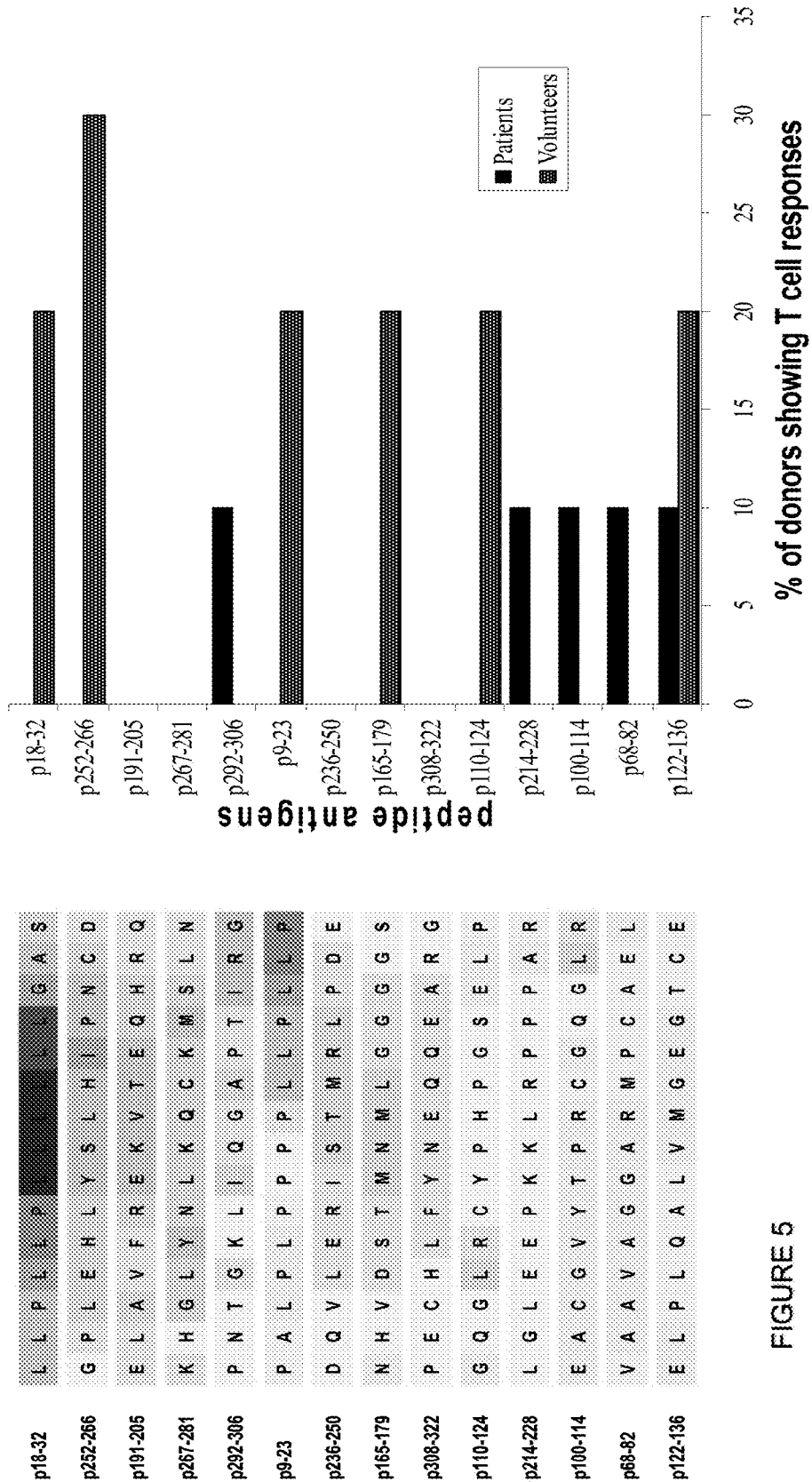
FIG. 5. Evaluating multiple algorithms for class II peptides identified immunogenic "hot spots" in the IGFBP-2 protein (SEQ ID NO: 2-15, respectively). Top 14 peptides associated with highest binding affinity across multiple HLA-DR alleles are shown. Numbers represent final scores from five algorithms for each peptide sequence, which were colored from dark red to light blue (darkest to lightest in this grayscale view; roughly top to bottom rows) in the order of rank scores. The bar graph on the right shows the percent of donors (patients and volunteers, as indicated) showing T cell responses to the identified peptide antigens of IGFBP-2.

As shown in FIG. 4, patients with breast and ovarian cancer have a detectable humoral immune response specific for IGFBP-2. The evaluation of multiple algorithms for class II peptides identified immunogenic "hot spots" in the IGFBP-2 protein. The top 14 peptides associated with highest binding affinity across multiple HLA-DR alleles are shown in FIG. 5. Numbers represent final scores from five algorithms for each peptide sequence, which were colored from dark red to light blue in the order of rank scores.

Figure 6A:
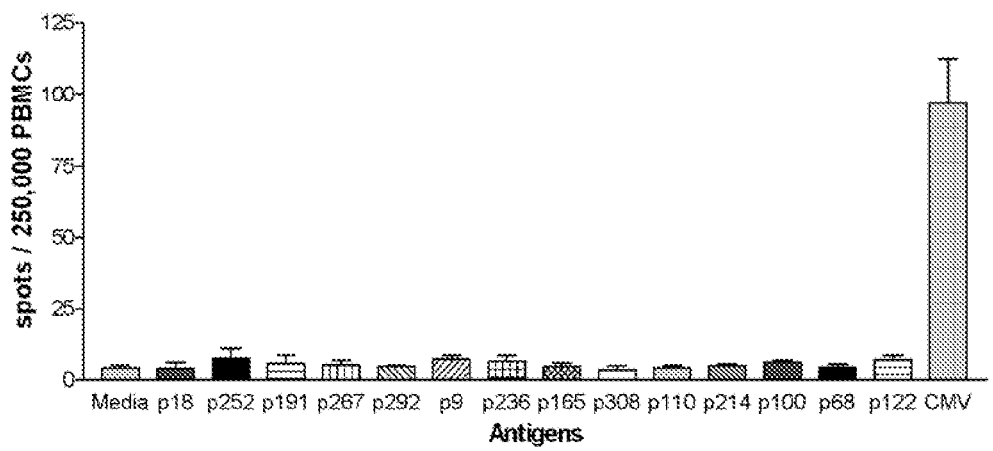
FIG. 6A-C. Immune responses specific for IGFBP-2 can be restricted or polyclonal. Three different patterns of specific response to IGFBP-2 epitopes were identified; no response (FIG. 6A; 60%), dominant response to one epitope (FIG. 6B; 20%), and generalized high response to multiple epitopes (FIG. 6C; 20%). Columns, mean spots for six replicates; Bars, SD; *, ** denote P<0.05 and P<0.005 in t-test. N=20.
Figure 6B:
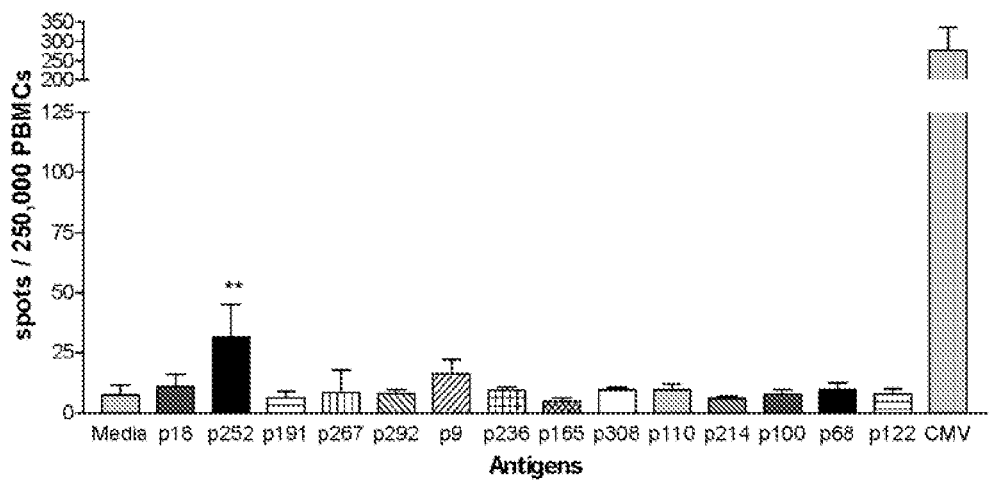
Figure 6C:
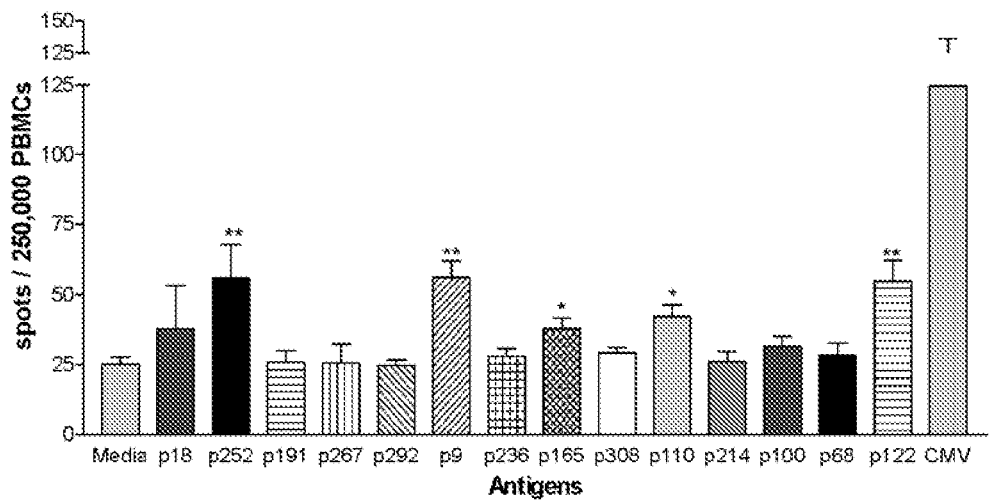
Figure 7A:
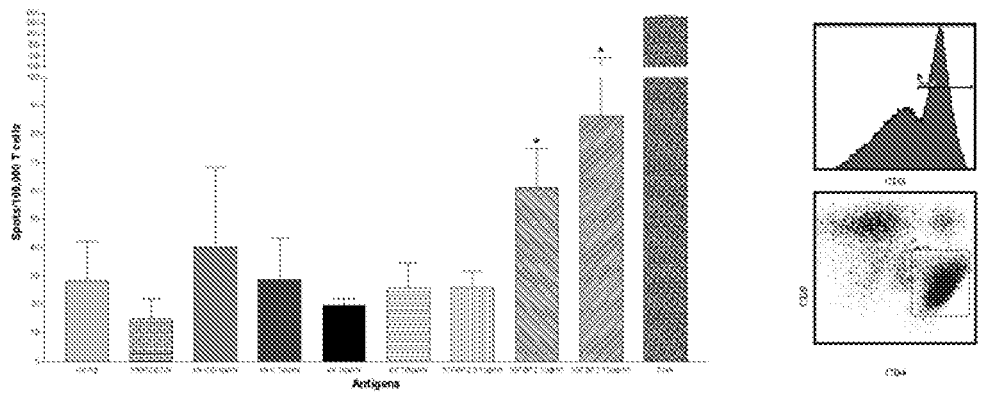
FIG. 7A-C. IGFBP-2 peptide specific CD4+ T cells can respond to protein presented endogenously on autologous antigen presenting cells. IGFBP-2 peptide specific T cell lines for p9-23 (FIG. 7A), p252-266 (FIG. 7B) and p292-306 (FIG. 7C) were analyzed in IFNγ ELISPOT. Antigen specificity and avidity to IGFBP-2 protein were detected in all of the cultured peptide specific T cells from three donors (left panels of 7A, 7B, 7C). Columns, mean spots for six replicates; Bars, SD; *, ** denote P<0.05 and P<0.005 in t-test. FACS analysis of cultured T cells for CD4+ T cell response (right panels of 7A, 7B, 7C).
Figure 7B:
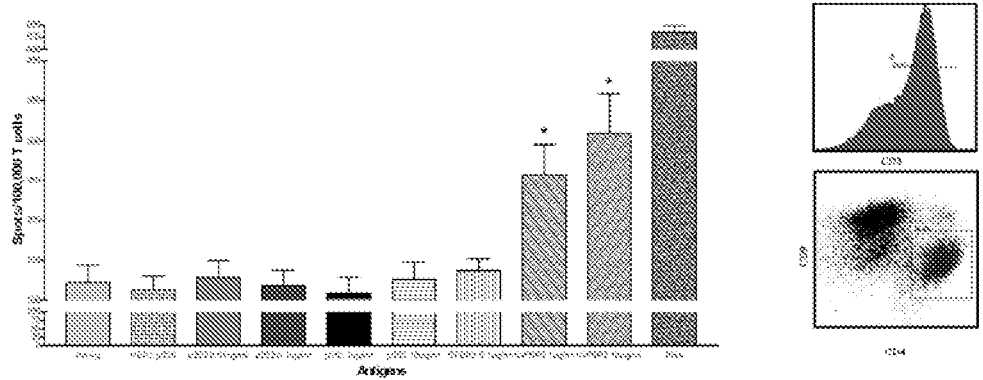
Figure 7C:
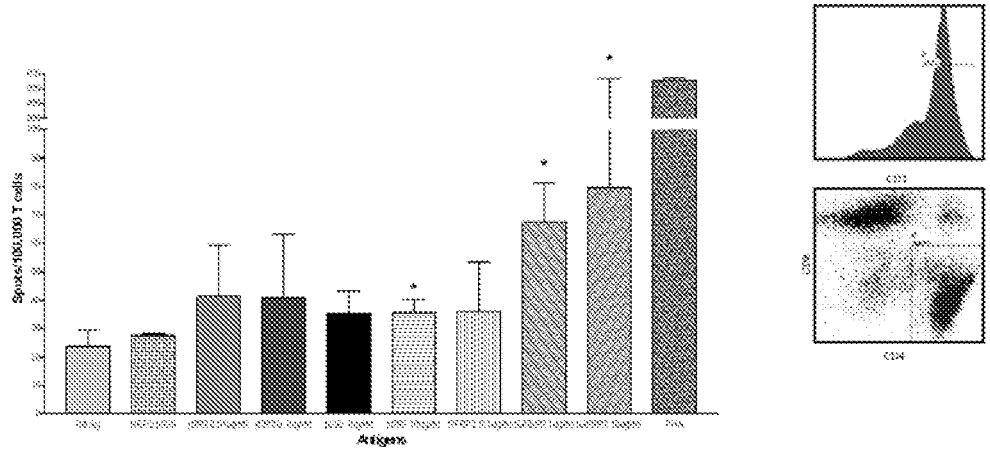

The data in FIG. 6 show that immune responses specific for IGFBP-2 can be restricted or polyclonal. Three different patterns of specific response to IGFBP-2 epitopes were identified; no response (FIG. 6A), dominant response to one epitope (FIG. 6B), and generalized high response to multiple epitopes (FIG. 6C). As shown in FIG. 7, IGFBP-2 peptide specific CD4+ T cells can respond to protein presented endogenously on autologous antigen presenting cells. IGFBP-2 peptide specific T cell lines for p9-23 (FIG. 7A), p252-266 (FIG. 7B) and p292-306 (FIG. 7C) were analyzed in IFNγ ELISPOT. Antigen specificity and avidity to IGFBP-2 protein were detected in all of the cultured peptide specific T cells from three donors (left panels of FIG. 7A, B, C). FACS analysis of cultured T cells for CD4+ T cell response is shown in the right panels of FIG. 7A, B, C.

Example 3

Epitopes of IGFBP-2

This example describes the HLA-A2 and Class II epitopes of IGFBP-2. These epitopes and their corresponding BIMAS and SYFPEITHI scores are provided in the following tables.

| HLA-A2 EPITOPES OF IGFBP-2 (SEQ ID NO: 16-22): | | | |
|---|---|---|---|
| Start Position | Sequence | BIMAS score | SFPEITHI score |
| 20 | LLPLLLLLL | 83.527 | 28 |
| 41 | VLFRCPPCT | 46.873 | 17 |
| 17 | LLPLLPLLL | 36.32 | 24 |
| 295 | KLIQGAPTI | 36.52 | 26 |
| 236 | QVLERISTM | 15.17 | 18 |
| 9 | ALPLPPPPL | 21.36 | 24 |
| 190 | ELAVFREKV | 9.7 | 22 |

| CLASS II EPITOPES OF IGFBP-2 (SEQ ID NO: 23-32): | | |
|---|---|---|
| Start Position | Sequence | SFPEITHI score |
| 167 | DSTMNMLGGGGSAGR | 37 |
| 300 | APTIRGDPECHLFYN | 36 |
| 14 | PPPLLPLLPLLLLLL | 30 |
| 250 | RGPLEHLYSLHIPNC | 30 |
| 101 | CGVYTPRCGQGLRCY | 29 |
| 22 | PLLLLLLGASGGGGG | 28 |
| 235 | DQVLERISTMRLPDE | 28 |
| 218 | PKKLRPPPARTPCQQ | 27 |
| 286 | CWCVNPNTGKLIQGA | 26 |
| 125 | QALVMGEGTCEKRRD | 26 |

AA = 330 (these motifs cover 43% of the entire molecule)

Amino acid sequence of human IGFBP-2
(SEQ ID NO: 1; immunogenic portions underlined):
MLPRVGCPALPLPPPPLLPLLPLLLLLLGASGGGGGARAEVLFRCPPCTP

ERLAACGPPPVAPPAAVAAVAGGARMPCAELVREPGCGCCSVCARLEGEA

CGVYTPRCGQGLRCYPHPGSELPLQALVMGEGTCEKRRDAEYGASPEQVA

DNGDDHSEGGLVENHVDSTMNMLGGGGSAGRKPLKSGMKELAVFREKVTE

QHRQMGKGGKHHLGLEEPKKLRPPPARTPCQQELDQVLERISTMRLPDER

GPLEHLYSLHIPNCDKHGLYNLKQCKMSLNGQRGECWCVNPNTGKLIQGA

PTIRGDPECHLFYNEQQEARGVHTQRMQ

Example 4

IGFBP-2 Vaccine Inhibits Tumor Growth in Vivo

Figure 8:
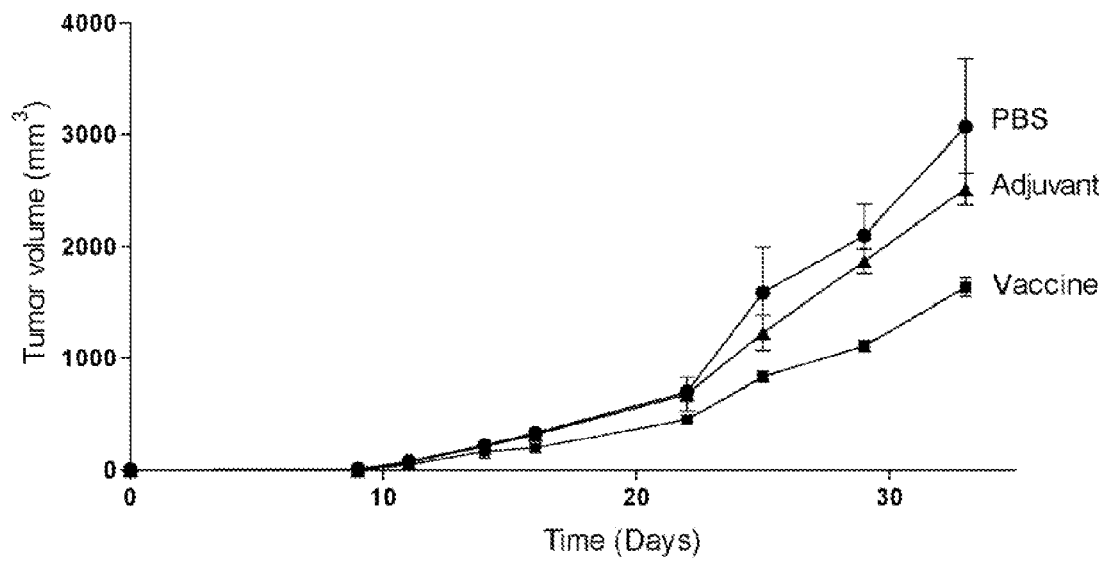
FIG. 8. Multipeptide vaccine from IGFBP-2 protein inhibits in vivo tumor growth in an implanted tumor model. Shown are tumor measurements from tumor-bearing control mice (PBS; ●, adjuvant only; ▲) and vaccinated mice (■) after tumor cell injection. Each data point is the mean tumor measurement±SE from 10 mice.
Figure 9:
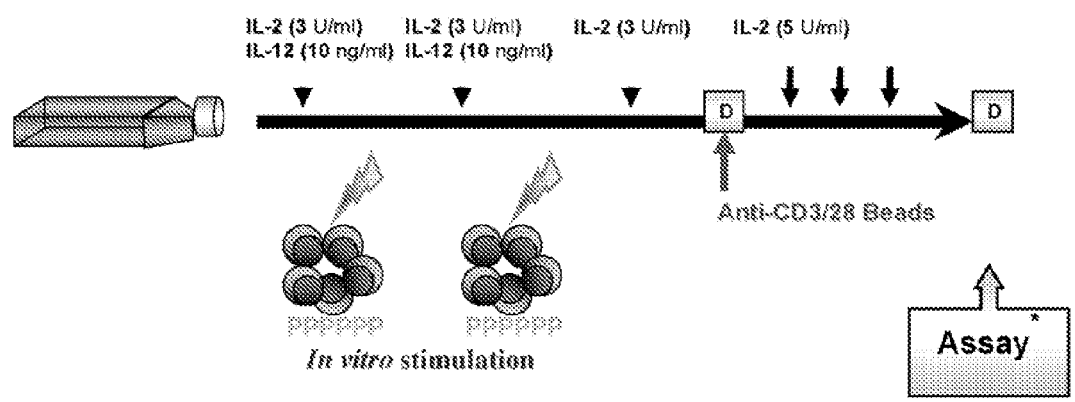
FIG. 9. Schematic illustration of protocol for generating IGFBP-2 specific T cell lines. Phenotype and antigen specificity of peptide-specific T cell line were assessed by IFN-γ ELISPOT and FACS analysis.

FIG. 8 shows that a multipeptide vaccine from IGFBP-2 protein inhibits in vivo tumor growth in an implanted tumor model. The vaccine included the following peptides: p9-23, p252-266, and p292-306. Shown are tumor measurements from tumor-bearing control mice (PBS; ●, adjuvant only; ▲) and vaccinated mice (■) after tumor cell injection. Each data point is the mean tumor measurement±SE from 10 mice.

Example 5

Insulin-Like Growth Factor Binding Protein 2 is an Essential Target for the Immunomodulation of Breast Cancer The following abbreviations are used in this Example: Ab: antibody; CMV: cytomegalovirus; ELISPOT: enzyme-linked immunospot; HER2: HER-2/neu; IFA: Incomplete Freund's Adjuvant; IGFBP: insulin-like growth factor binding protein; IGF: insulin like growth factor; IGFR: insulin-like growth factor receptor; MMC: mouse mammary carcinoma; NCBI: National Center for Biotechnology Information; PHA: phytohemagglutinin. References cited in this Example are indicated by numbers in parentheses; corresponding citations can be found at the end of the Example.

This example demonstrates that IGFBP-2 is an immune target in breast cancer. IGFBP-2 IgG antibody immunity was detected in breast cancer patients compared to controls (p=0.0008). To evaluate for the presence of T cell immunity, we identified potential pan HLA-DR binding epitopes derived from IGFBP-2 and tested the peptides for immunogenicity. The majority of epitopes elicited peptide specific T cells in both patients and controls and had high sequence homology to bacterial pathogens. IGFBP-2 peptide-specific T cells could respond to naturally processed and presented IGFBP-2 protein, indicating these peptides were native epitopes of IGFBP-2. Finally, both immunization with IGFBP-2 peptides as well as adoptive transfer of IGFBP-2 competent T cells mediated an anti-tumor effect in a transgenic mouse model of breast cancer. This is the first report of IGFBP-2 as a human tumorantigen and suggests the protein may serve as a tumor rejection antigen.

Studies described here demonstrate that IGFBP-2 is a human tumor antigen eliciting both antibody and T cell immunity in women with breast cancer. Moreover, in a transgenic mouse model of breast cancer, T cells specific for IGFBP-2 mediate tumor rejection. Thus, IGFBP-2 may represent an essential target in the immunomodulation of breast cancer.

Materials and Methods

Human Subjects.

Serum samples were collected from 220 patients with breast cancer after written consent. Serum samples derived from 100 volunteer donors between the ages 18 and 75 years were obtained from the Puget Sound Blood Bank, Seattle, Wash. The volunteers met all criteria for blood donation. Control sera were aliquoted and stored at −80° C. For T cell studies, PBMCs were obtained by leukapheresis, after informed consent, from 9 breast cancer patients and one ovarian cancer patient, and 10 volunteer donors. Cells were ficolled and cryopreserved as previously described (14).

Evaluation of humoral immunity specific for IGFBP-2. Antibody response to IGFBP-2 was assessed by indirect ELISA using recombinant protein. Briefly, alternate columns on Immulon 4HBX plates (Dynex Technologies, Chantilly, Va.) were coated overnight with purified human recombinant IGFBP-2 protein (Sigma, St. Louis, Mo.) and PBS/1% BSA, blocked for 1 hour with PBS/5% BSA, and washed with PBS/Tween-20. After washing, 50 µl/well of control or experimental sera were added in duplicate titration sets. After overnight incubation at 4° C., plates were washed and anti-human/HRP conjugate (Zymed Laboratories, South San Francisco, Calif.) was added at 50 µl/well. Plates were washed again after a 45-minute incubation at 4° C. and developed as previously described (15). For the murine serum samples the same protocol was used except for the following substitutions: purified mouse recombinant IGFBP-2 protein (Sigma) and anti-mouse IgG/HRP conjugate (Zymed Laboratories).

IGFBP-2 antibody immunity detected by ELISA was verified using Western blot analysis. The serum samples were incubated overnight at 4° C. after the addition of 15 µl Protein A+G (Oncogene Research Products, Cambridge, Mass.) and 10 µl purified recombinant IGFBP-2 protein (Sigma). Pellets were washed twice with NNET buffer containing 15.2 ml 5-M NaCl, 10 ml 0.25-M EDTA, and 25 ml 1M Tris HCl in 500 ml dH2O, then twice in the same buffer after addition of 0.5% NP-40 (Sigma). SDS-PAGE running buffer was added to the pellets after the last wash and pellets were kept at 4° C. overnight prior to analysis.

The immunoprecipitated proteins were electrophoresed on 12.5% polyacrylamide gels in the Pharmacia Phast System (Pharmacia LKB Biotechnology AB, Uppsala, Sweden) for 45 minutes with a current of 250V, then transferred to 0.45 µm pore nitrocellulose paper (Amersham Pharmacia Biotech, Piscataway, N.J.) using a semi-dry transfer cell (Bio-Rad Laboratories, Hercules, Calif.) at 22 volts for 30 minutes. IGFBP-2 protein was identified using an IgG Mab (Santa Cruz Biotechnology, Santa Cruz, Calif.) as primary antibody diluted 1:1000 with Tris-buffered saline/1% BSA/0.1% IGEPAL (Sigma). After washing, a diluted polyclonal goat anti-mouse horseradish peroxidase-conjugated secondary antibody (Amersham), diluted 1:10,000, was incubated with the blot for 45 minutes. After a final wash, the blots were dipped in ECL (Amersham) for one minute before being developed on ECL Hyperfilm (Amersham) with an exposure of 10 seconds.

Scoring System for the Prediction of MHC Class II Binding Epitopes.

High binding affinity across multiple class II alleles predicts immunogenic human epitopes (16). Other investigators have shown that predicted peptides that score highly across more than one algorithm are more likely to be natural epitopes (17). Therefore, to identify IGFBP-2-specific MHC class II epitopes that have optimal binding affinity and promiscuity across multiple alleles, we developed a combined scoring system using widely available algorithms for predicting class II binding. The following five algorithms were used for prediction of Class II peptides derived from the IGFBP-2 protein sequence: SYFPEITHI (Institute for Cell Biology, Heidelberg, Germany), Propred (Institute of Microbial Technology, Chandigarh, India), MHC-Thread (University of Aberdeen, Aberdeen, UK), Average Binding matrix method (18), and Rankpep (Havard, Boston, Mass.). Binding predictions were generated using each algorithm for the 15 most common MHC class II alleles: DRB1*0101, DRB1*1501, DRB1*0301, DRB1*0401, DRB1*0404, DRB1*0405, DRB1*0701, DRB1*0802, DRB1*0901, DRB1*1101, DRB1*1201, DRB1*1302, DRB3*0101, DRB4*0101, DRB5*0101.

The 14 peptides described in this study were selected as follows. For each available MHC Class II allele from the 5 algorithms, 20 peptide sequences were initially selected solely on the basis of the rank order of the predicted binding affinity. The sequences ranged from 9-15 amino acids in length. Individual amino acids for each selected peptide were assigned a score between 1 and 20, with 20 being an amino acid contained in a peptide sequence that ranked highest for predictive binding affinity across multiple algorithms. Scoring individual amino acids accounted for the multiple peptide overlaps occurring within and across algorithms. The scores (S) for each amino acid were summed up across the multiple MHC Class II alleles from all 5 algorithms. Then, the number (N) of MHC class II alleles for which each amino acid was predicted to have high affinity binding were counted. The final score for each amino acid was calculated by multiplying S and N. For ease of identifying the most potentially immunogenic segments of the IGFBP-2 protein, each amino acid was assigned a color (from dark red to light blue) based on its final score, with dark red being highest at ≥9,000 and light blue the lowest at 500-1,000 (FIG. 12A). Thus, the dark red color corresponds to a sequence where multiple peptides scored highly within an algorithm as well as across algorithms. Light blue represents sequences that are the least potentially immunogenic of all predicted high binding peptides. Twenty distinct 15-amino-acid peptides were chosen, representing all potential "immunogenic hot spots". Scores (S×N) of the amino acids ranged from 0 to 9394. The sum of the scores of each selected 15-mer peptides ranged from 7,610 to 107,357. Of the 20, the top 14 peptides scoring above the lower end of 99% Confidence Interval (CI) of the mean were chosen for construction and further analysis (FIG. 12A).

IGFBP-2 peptides were synthesized by Genemed Synthesis Inc. (South San Francisco, Calif.), purified by high-performance liquid chromatography, and characterized by mass spectrometry for use in all experiments. The 14 peptide sequences were compared in NCBI databases using BLAST program to identify shared homology with other human proteins or with proteins from other species (see Table below).

Evaluation of T Cell Responses to IGFBP-2 Peptides and Protein.

PBMCs from 20 subjects were evaluated by ELISPOT for antigen-specific IFNγ production. Briefly, 96-well nitrocellulose plates (Millititer, Millipore, Bedford, Mass.) were coated overnight at 4° C. with 50 µl/well of 10 µg/ml anti-human IFN-γ monoclonal antibody (clone: 1-D1K, MabTech, Nacka, Sweden) in Dulbecco's Phosphate Buffered Saline (DPBS) (Gibco Invitrogen, Carlsbad, Calif.). The plates were washed 3 times for 5 minutes each with 200 µl DPBS/well and blocked with 100 µl/well of 2% bovine serum albumin in DPBS for 2 hours at room temperature. PBMCs were plated at 250,000 cells per well with 10 µg/ml of the various IGFBP-2 peptides, 2.5 µg/ml of CMV lysate or media alone in a total volume of 200 µl/well for 96 hours at 37° C. in 5% $CO_2$. The plates were washed with 200 µl of 0.05% Tween/DPBS. Wells were incubated for 2.5 hours at room temperature using 50 µl of 1 µg/ml anti-IFN-γ (clone: 7-B6-1, MabTech) antibody diluted in 0.05% Tween™/DPBS. After washing three times with PBS, streptavidin-alkaline phosphatase (Bio-Rad) was diluted 1/1000 and added at 50 µl/well for 2 hours at room temperature. After another washing step with PBS, 100 µl/well of BCIP/NBT substrate (Bio-Rad) was added for up to 20 minutes. Color development was stopped by washing under running tap water. After drying overnight at room temperature, colored spots were counted using a AID ELISPOT High-Resolution reader system and AID ELISPOT Software version 3.5 (Autoimmun Diagnostika GmbH, Strasberg, Germany). The mean number of spots and SEM from six replicates at each dilution was reported for each antigen. Response to peptide antigens was considered to be positive when the mean number of spots in the experimental wells were statistically different ($p<0.05$) from the mean number from no antigen control wells.

For the ELISPOT assay of the cultured T cell lines, $1\times10^5$ of PBMCs, inactivated by irradiation at 3,000 rads, were added to the same number of cultured T cells per well and incubated for 24 hours at 37° C. in 5% $CO_2$. Peptide-specific T cells were assayed for IFNγ production in the presence of IGFBP-2 peptides (25 µg/ml), IGFBP-2 protein (2.5 µg/ml), and 1 µg/ml of PHA as positive control. HER-2/neu peptide p328-342 (25 µg/ml), myoglobin (2.5 µg/ml) and media alone served as negative controls. All assays were performed in 6 well replicates.

To assess the antigen-specific T cell responses in the vaccinated, tumor-bearing mice, $2\times10^5$ splenocytes per each well were used for the IFNγ ELISPOT assay. Briefly, spleens were pressed through the 70 µm cell strainer (BD Labware, Franklin Lakes, N.J.). The cells were washed with RPMI-1640 (Invitrogen, Grand Island, N.Y.) and pelleted at 300 g for 10 minutes. To lyse red blood cells, the pellet was resuspended in 5 ml of ACK lysis buffer (0.15 M $NH_4Cl$, 10 mM $KHCO_3$, 0.1 mM $Na_2EDTA$, pH 7.4) per spleen and incubated for 5 minutes at room temperature. Standard mouse T cell medium (described below) was added to stop the lysis buffer, and the cells were pelleted. Resultant splenocytes were stimulated by different antigens: IGFBP-2 peptides mixture (10 µg/ml of each peptides p8-31, p251-265, p291-305), murine IGFBP-2 protein (2.5 µg/ml), and 1 µg/ml of PHA as positive control. The same protocol for human IFNγ ELISPOT was used except for the following substitutions: anti-mouse IFN-γ monoclonal antibody (clone: AN18, MabTech, Nacka, Sweden) for coating and biotinylated anti-mouse IFN-γ (clone: R4-6A2-biotin, MabTech) antibody for detection.

Reagents Used for the Generation of T Cell Lines.

T cell media used for human T cell expansions consisted of X-Vivo-15 (Biowhittaker, Walkersville, Md.) supplemented with 10% human AB serum (Valley Biomedical, Winchester, Va.), 10 mM acetylcysteine (Faulding, Paramus, N.J.), 20 mM HEPES, 2 mM L-glutamine, 100 µg/ml penicillin and 100 µg/ml streptomycin (Invitrogen, Grand Island, N.Y.). Lyophilized human recombinant interleukin-2 (IL-2) (Hoffmann-La Roche, Nutley, N.J.) was reconstituted with sterile water, stored at 4° C., and used to expand T cells in vitro. A portion of the stock IL-2 was diluted with T cell media before use. Lyophilized human recombinant interleukin-12 (IL-12) (R&D Systems, Minneapolis, Minn.) was reconstituted into PBS/1% human serum albumin (Bayer, ZLB Bioplasma AG, Berne, Switzerland), aliquoted, and stored at −20° C. before use. Anti-CD3/CD28 beads were kindly provided by Xcyte Therapies Corporation (Seattle, Wash.). For murine T cell culture, media consisted of RPMI-1640 (Invitrogen, Grand Island, N.Y.) supplemented with 10% heat-inactivated fetal bovine serum (Gemini Bio-Products, West Sacramento, Calif.), 10 mM acetylcysteine (Faulding, Paramus, N.J.), 20 mM HEPES, 2 mM L-glutamine, 100 µg/ml penicillin, and 100 µg/ml streptomycin (Invitrogen, Grand Island, N.Y.). Mouse recombinant IL-7 was purchased from R&D Systems and human recombinant IL-15 from PeproTech Inc (Rocky Hill, N.J.). Lyophilized recombinant IL-7 and IL-15 were reconstituted into PBS/1% BSA, aliquoted, and stored at −20° C. before use.

Generation of IGFBP-2-Specific T Cell Lines.

For the generation of human T cell lines, cryopreserved PBMC were thawed, washed, and resuspended at a concentration of $3\times10^8$ cells/ml in T cell media. The cells were stimulated with 10 µg/ml of various IGFBP-2 peptides and incubated at 37° C. in 5% $CO_2$. On days 4 and 8, 3 U/ml of recombinant human IL-2 and 10 ng/ml of recombinant human IL-12 were added to the stimulated cells (19). On day 12, the stimulated cells were harvested from the culture flasks and resuspended at a concentration of $1\times10^6$/ml in fresh media containing $1\times10^6$/ml of Xcyte CD3/CD28 beads. The cells and the beads were mixed gently and co-incubated at 37° C. in 5% $CO_2$. From days 14 to 23, the number of the cells was evaluated every two to three days and the cells were diluted to a concentration of $0.5-1\times10^6$/ml with fresh media. IL-2 was added at a final concentration of 5 U/ml into the cell culture.

For the generation of IGFBP-2-specific mouse T cell lines, pooled splenocytes from IGFBP-2 peptide vaccinated mice were used. The same protocol as for human T cell expansion was used, except that 10 ng/ml of recombinant mouse IL-7 and 5 ng/ml of recombinant human IL-15 were added on days 5 and 12. On day 26, cultured T cells were harvested and transferred to tumor bearing mice at the dose of $10\times10^6$ T cells/mouse. The same number of splenocytes derived from naïve mice were used for controls.

Phenotypic Analysis of the T Cells.

To phenotype the IGFBP-2 peptide-specific cultured human T cells, four-color flow cytometric analysis was performed using the following antibodies (Ab): fluorescein isothiocyanate (FITC)-conjugated anti-CD8, phycoerythrin (PE)-conjugated anti-CD4, PE-Cy5-conjugated CD3, and PE-Cy7-conjugated CD56 (all from Beckman Coulter, Fullerton, Calif.). For extracellular staining, cells were incubated for 30 minutes at room temperature with optimal dilution of each Ab. For the analysis of FoxP3 expression in PBMCs and antigen-specific T cells, intracellular staining of FoxP3 using a monoclonal Ab (clone 259D, mouse IgG1, purified anti-human FoxP3, Biolegend, San Diego, Calif.) together with surface staining with FITC anti-CD3, PE-Cy7 anti-CD4, and PE-Cy5 anti-CD25 was performed following the manufacturer's protocol. FACS analysis was performed using Cytomics FC 500 MPL Flow Cytometry System with CXP software (Beckman Coulter, Fullerton, Calif.). Typically, 50,000-100,000 events were collected per sample.

Mice and Tumor Cell Lines.

Neu-transgenic mice (strain name, FVB/N-TgN (MMTV-neu)-202Mul) were obtained from Charles River Laboratory (Bar Harbor, Me.) and bred under SPF conditions at the University of Washington. Animal care and use were in accordance with institutional guidelines. Mice were either immunized subcutaneously with 50 µg of each IGFBP-2 peptide as a mixture in CFA/IFA (Sigma), adjuvant alone, or PBS alone. As a peptide control, 15-mer of a pan-HLA-DR binding peptide from tetanus toxoid was used in combination with adjuvant. Three immunizations were given two weeks apart. Two weeks after the $3^{rd}$ vaccination, mice were inoculated with $1 \times 10^6$ mouse mammary carcinoma (MMC) cells, derived from fresh spontaneous tumor from the neu-transgenic mouse, s.c. on the mid-dorsum with a 23-gauge needle (20). To evaluate humoral immune responses specific to murine IGFBP-2, sera from the experimental mice were taken by retro-orbital bleeding at 2 different time points: pre- and 5 weeks after tumor inoculation. For the adoptive T cell experiments, tumor was established in each mouse by injecting with $1 \times 10^6$ MMC cells 10 days before the T cell transfer. Tumors were measured every two to three days with Vernier calipers, and tumor volume was calculated as the product of length× width×height×0.5236. in vivo data are presented as mean±SE of 5-10 mice/group.

Reverse Transcriptase PCR Analysis of IGFBP-2 mRNA Expression.

Total RNA from the MMC cell line was isolated using RNA4Aqueous kit (Ambion, Austin, Tex.). cDNA was generated from 5 µg of RNA from Superscript III reverse transcriptase (Invitrogen, San Diego, Calif.) with oligo-dT as primers according to manufacturer's protocol. Five µl of 1:40 diluted cDNA was then used as a template for PCR analysis. The primer pair to amplify an 80 by was designed based on Genebank sequences of mouse IGFBP-2, 5'-GCGCGGG-TACCTGTGAAA-3' (sense; SEQ ID NO: 33) and 5'-TC-CCTCAGAGTGGTCGTCATC-3' (antisense; SEQ ID NO: 34). The cycling conditions were as follows: 95° C. for 10 min, 40 cycles of denaturation at 95° C. for 15 s, 62° C. for 60 s, followed by a final extension at 72° C. for 4 min.

Statistical Analysis.

The unpaired, two-tailed Student's t-test was used to evaluate differences in T cell responses in ELISPOT assay, antibody responses between patients and volunteer donors, and differences in tumor growth between animal treatment groups. The relationship between the degree of homology and the immunogenicity of the peptides was analyzed by the Spearman correlation analysis. The Chi-square trend and the Student's t-test were used to compare the magnitude and pattern of T cell responses in cancer patients and volunteer donors. In all cases, a p value less than 0.05 was considered significant. All statistical analyses were performed using GraphPad Prism version 3.02 (GraphPad Software, San Diego, Calif.).

Results

Breast Cancer Patients can have Antibody Immunity to IGFBP-2.

Figure 11A:
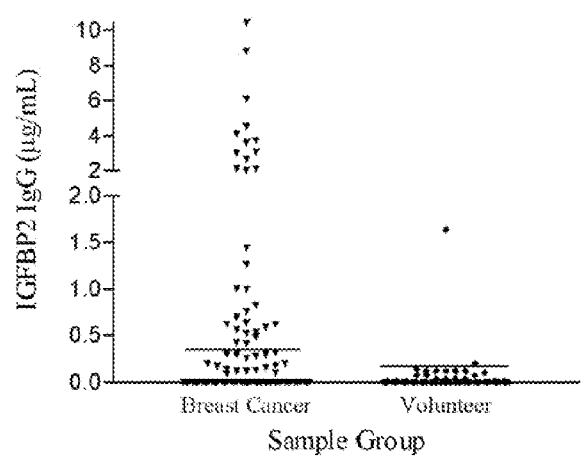

Sera from patients with breast cancer were more likely to have antibody immunity specific for IGFBP-2 than samples from volunteer donors (p=0.0008) (FIG. 11A). Moreover, the level of antibody response to IGFBP-2 was significantly higher in breast cancer patients (p=0.0008) when compared to volunteer donors. The mean level of IGFBP-2-specific IgG immunity for breast cancer patients was 0.3 µg/ml (range, 0-10.4), and for volunteer donors was 0.032 µg/ml (range, 0-1.6 µg/ml). All antibody responses were confirmed by Western blot. A representative example of two patient samples positive for IGFBP-2 antibodies (P1, P3) in ELISA and one negative patient sample (P2) are shown in duplicates (FIG. 11B).

The Majority of IGFBP-2 Peptides Identified by a Scoring System Combining Multiple MHC Class II Peptide Binding Algorithms can be Recognized by Human T Cells.

Figure 12B:
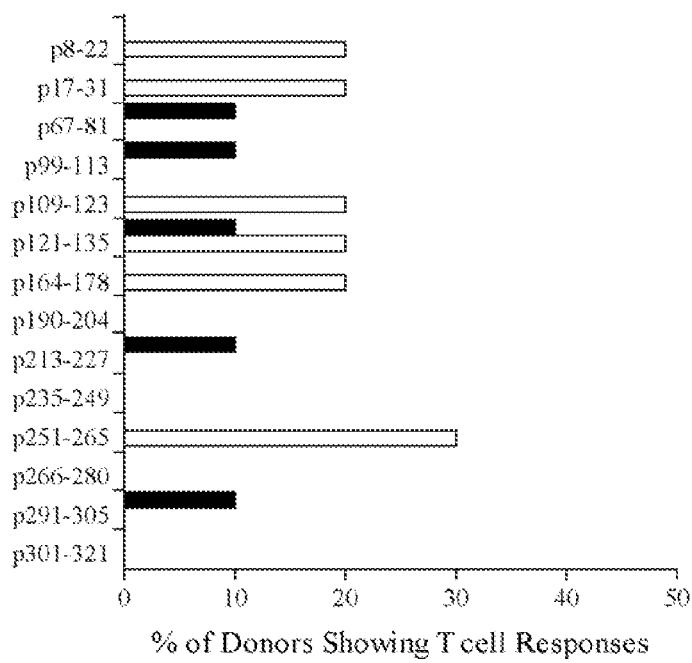

FIG. 12A depicts the entire IGFBP-2 protein sequence and the identified immunogenic "hot spots". Ten (71%) of the 14 evaluated peptides stimulated significant IFN-γ ELISPOT responses in volunteer donors and cancer patients (FIG. 12B). Of the 14 peptides, 36% elicited responses in cancer patients and 50% were immunogenic in volunteer donors. Fourteen percent of the peptides elicited responses in both cancer patients and volunteer donors. Due to the high incidence of T cell responses to IGFBP-2 peptides in volunteer donors, we evaluated the peptides for sequence homology with other known proteins. The majority (13/14) of peptides displayed significant sequence homology with bacterial pathogens. Eight of the 14 immunogenic IGFBP-2 peptides demonstrated ≥60% shared homology with common pathogens, such as *Pseudomonas* and *Aspergillus* (see Table). However, there was no relationship between the degree of homology and the immunogenicity of the peptides (Spearman r=0.088, p=0.76).

Figure 13A:
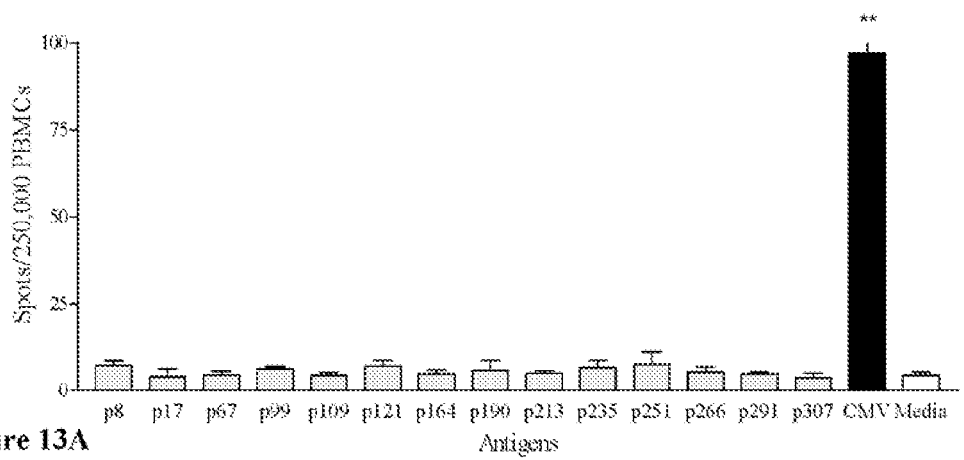
FIG. 13A-C. Human T-cell responses specific for IGFBP-2 peptides can be restricted to a single peptide or demonstrate multiple specificities. Three patterns of T cell response to IGFBP-2 epitopes were identified in tested subjects.
Figure 13B:
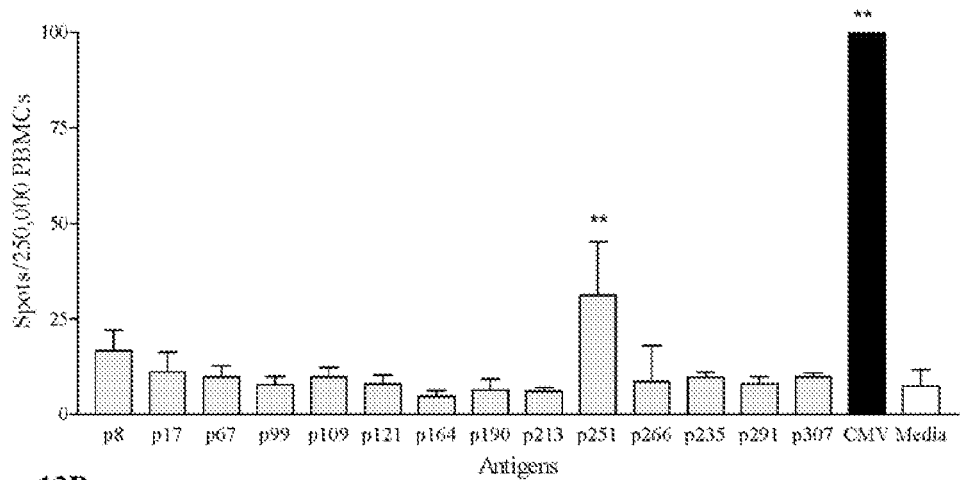
Figure 13C:
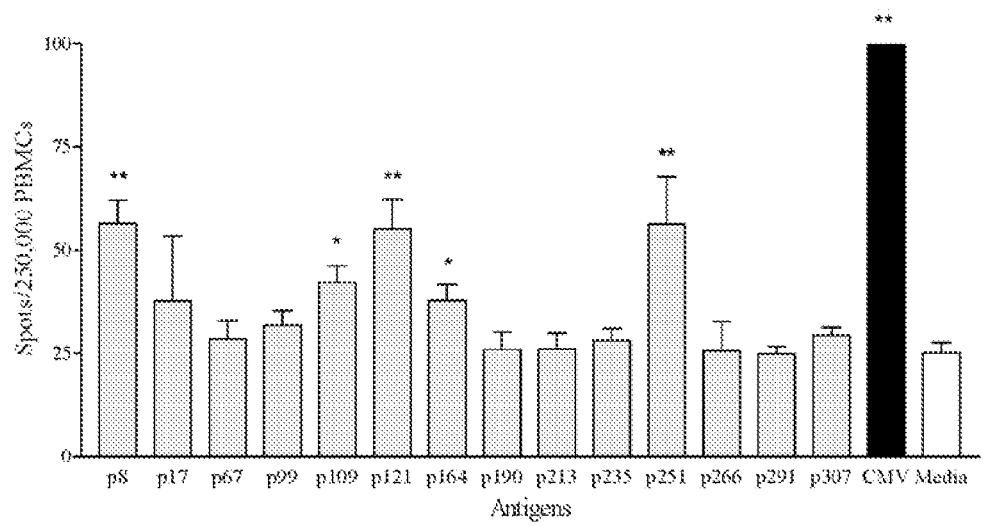

Human T-cell responses specific for IGFBP-2 peptides can be restricted to a single peptide or demonstrate multiple specificities. Eight of 20 subjects (40%) showed IGFBP-2 peptide specific IFN-γ producing T-cell responses to one or more peptides. Representative examples are shown in FIG. 13. Twelve out of 20 (60%) had no detectable immunity to any IGFBP-2 peptide (e.g. FIG. 13A). Half of the responding donors (n=4) demonstrated immune responses restrictive to single epitope (e.g. FIG. 13B) and the other half had polyclonal responses to multiple epitopes (e.g. FIG. 13C). There were no significant differences between cancer patients and volunteer donors in terms of pattern of response ($\chi^2$=3.125, p=0.077) or magnitude (p=0.48) of the IGFBP-2 peptide specific T cell response.

IGFBP-2 Peptide Specific T Cells Respond to IGFBP-2 Protein.

Figure 14A:
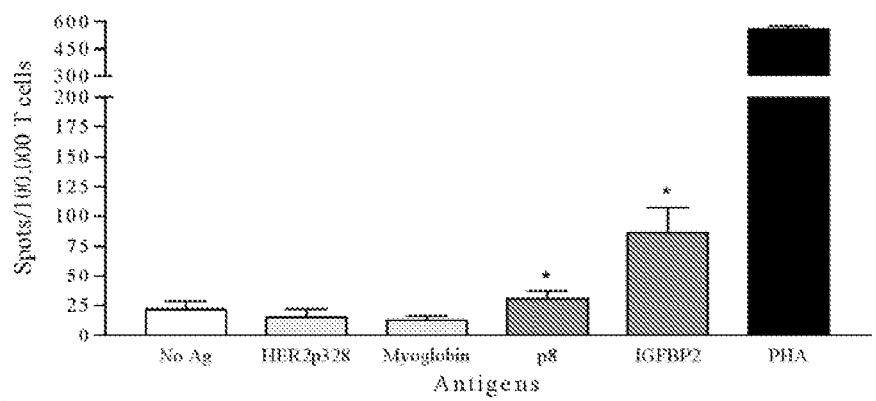
FIG. 14A-C. IGFBP-2 peptide-specific T cells respond to IGFBP-2 protein. Antigen-specific responses of IGFBP-2 peptide-specific T cell lines (p8-22, FIG. 14A; p251-265, FIG. 14B; and p291-305, FIG. 14C) were analyzed by IFNγ ELISPOT. Antigens tested include IGFBP-2 peptides and protein (dark gray bars), PHA positive control (black bar), HER-2 p384-398 peptide and myoglobin as negative controls (light gray bars), and media alone (white bar). Data are expressed as the mean and standard deviation of IFN-γ-secreting spots for six replicates; *, ** denote p<0.05 and p<0.005 versus spots obtained from media alone wells.
Figure 14B:
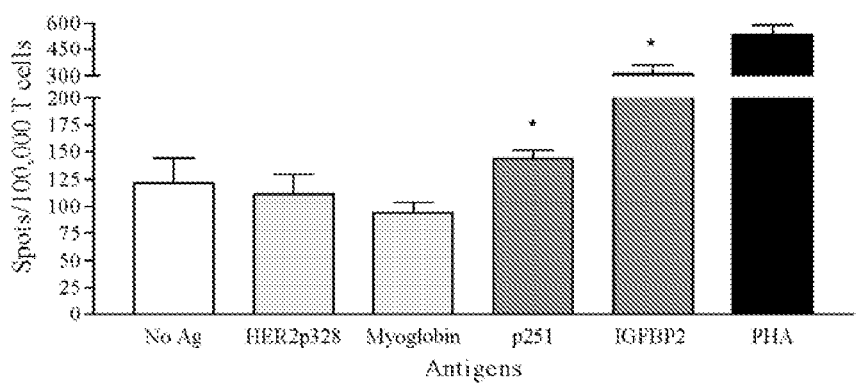
Figure 14C:
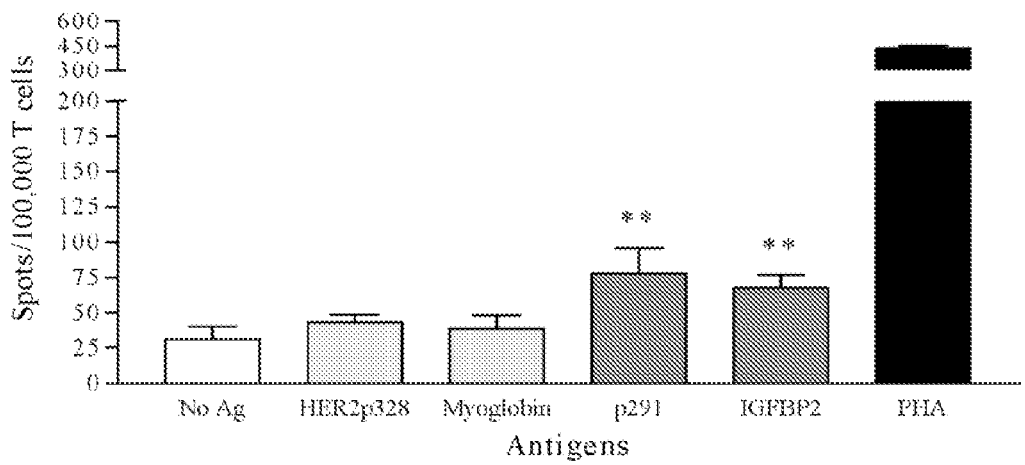

To demonstrate that IGFBP-2 peptide specific T cells could respond to IGFBP-2 protein and thus represent native epitopes, PBMCs from one breast cancer patient and two volunteer donors who demonstrated peptide-specific T cell responses were selected for T cell expansion. Each subject had a response to a different peptide: p8-22, p251-265, or p291-305. The IGFBP-2 p8-22 T cell line responded significantly to IGFBP-2 protein as compared to human myoglobin, a control protein (p=0.0022) (FIG. 14A). Similarly, IGFBP-2 p251-265 (FIG. 14B) and p291-305 (FIG. 14C) T cell lines responded to the recombinant proteins as compared to control (p=0.002 and p=0.0022 respectively). All of the peptide-specific T cell lines showed specific reactivity by IFNγ secretion in response to their stimulating IGFBP-2 peptide and not to HER2 p328-342, a control 15-mer peptide (p<0.05). Thus, the T cell lines were both IGFBP-2 peptide and protein specific.

The IGFBP-2-specific T cell lines were predominantly composed of CD4+ T cells (mean 53.6%, range 46.4-66.3%). CD8+ T cells (mean 36.0%, range 25.1-43.7%) and cells double negative for CD4+ and CD8+ (mean 6.7%, range 4.0-

9.5%) accounted for the rest of the cell population. None of the cultured T cell lines demonstrated outgrowth of regulatory T cells.

The mean percentage of T regulatory cells was 0.7% (range 0.2-1.1%) after in vitro expansion.

IGFBP-2 is a Tumor Rejection Antigen in Neu-Transgenic Mice.

Figure 15A:
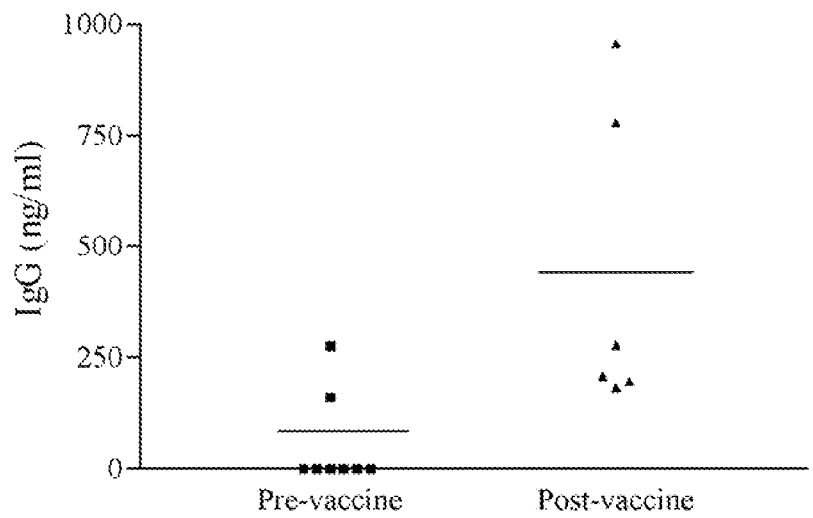
FIG. 15A-D. IGFBP-2 is a tumor rejection antigen in neutransgenic mice.
Figure 15B:
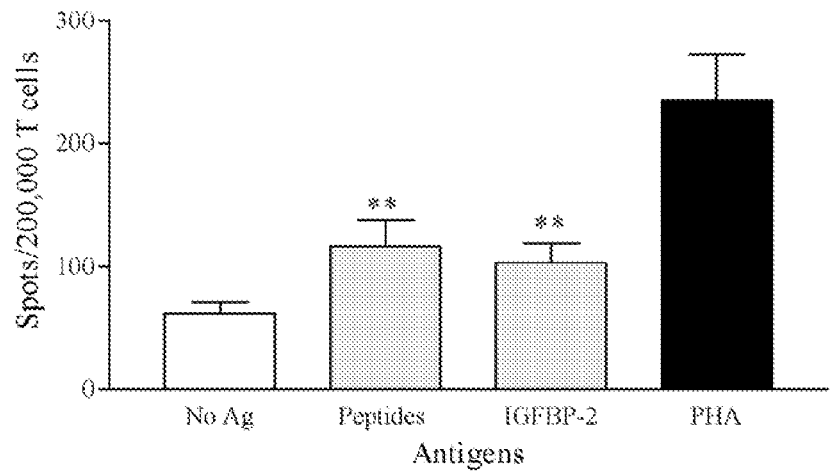

Human IGFBP-2 has a high degree of homology with murine IGFBP-2 (82%) and for this reason we questioned whether immunity to IGFBP-2 would impact tumor growth, i.e. whether IGFBP-2 was a tumor rejection antigen. IGFBP-2 peptides p8-22, p251-265, and p291-305 were chosen for in vivo study because they were shown to be native epitopes of human IGFBP-2, and all have significant homology with murine IGFBP-2 protein (see Table). After verifying IGFBP-2 mRNA expression in both an MMC cell line and fresh spontaneous tumor from neu-transgenic mice using RT-PCR, animals were immunized with a vaccine composed of all three peptides. The peptides were immunogenic in the mice. Immunized mice developed murine IGFBP-2-specific IgG antibody immunity, the level of IGFBP-2 specific IgG was significantly higher post- than pre-vaccine in vaccinated mice (p<0.05) (FIG. 15A). The vaccine generated both peptide and murine IGFBP-2 protein-specific IFN-γ secreting T cells (FIG. 15B). IFN-γ ELISPOT responses were significantly higher to the peptide mix (p=0.0022) and murine recombinant protein (p=0.002) as compared to no antigen wells.

TABLE

Homology of peptides derived from IGFBP-2 protein

| IGFBP-2 peptides | % Homology With Mouse IGFBP-2 | Homologous Protein Protein Source of Species | % Homology |
|---|---|---|---|
| p8-22 | 67 | Aspergillus oryzae | 67 |
| p17-31 | 0 | Candida albicans | 67 |
| p67-81 | 0 | Propionibacterium acnes | 60 |
| p99-113 | 80 | Human, murine, canine IGFBP3, 4, 5 | 67-80 |
| p109-123 | 80 | Pseudomonas fluorescens | 53 |
| p121-135 | 80 | Pseudomonas aeruginosa | 60 |
| p164-178 | 86 | Trypanosoma cruzi | 53 |
| p190-204 | 93 | Trypanosoma cruzi | 73 |
| p213-227 | 93 | Aspergillus oryzae | 67 |
| p235-249 | 93 | Candida albicans | 53 |
| p251-265 | 100 | Pseudomonas aeruginosa | 47 |
| p266-280 | 100 | Lactobacillus reuteri | 47 |
| p291-305 | 93 | Schistosoma japonicum | 60 |
| p307-321 | 80 | Staphylococcus aureus | 47 |

Figure 15C:
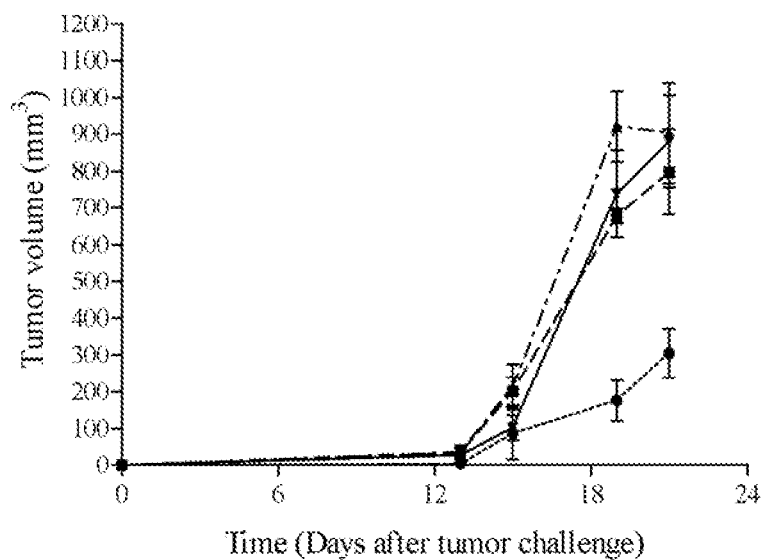
Figure 15D:
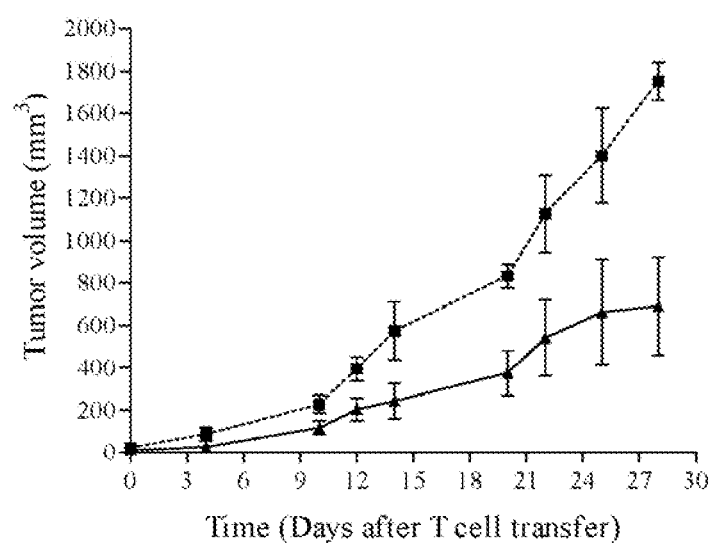
Figure 16:
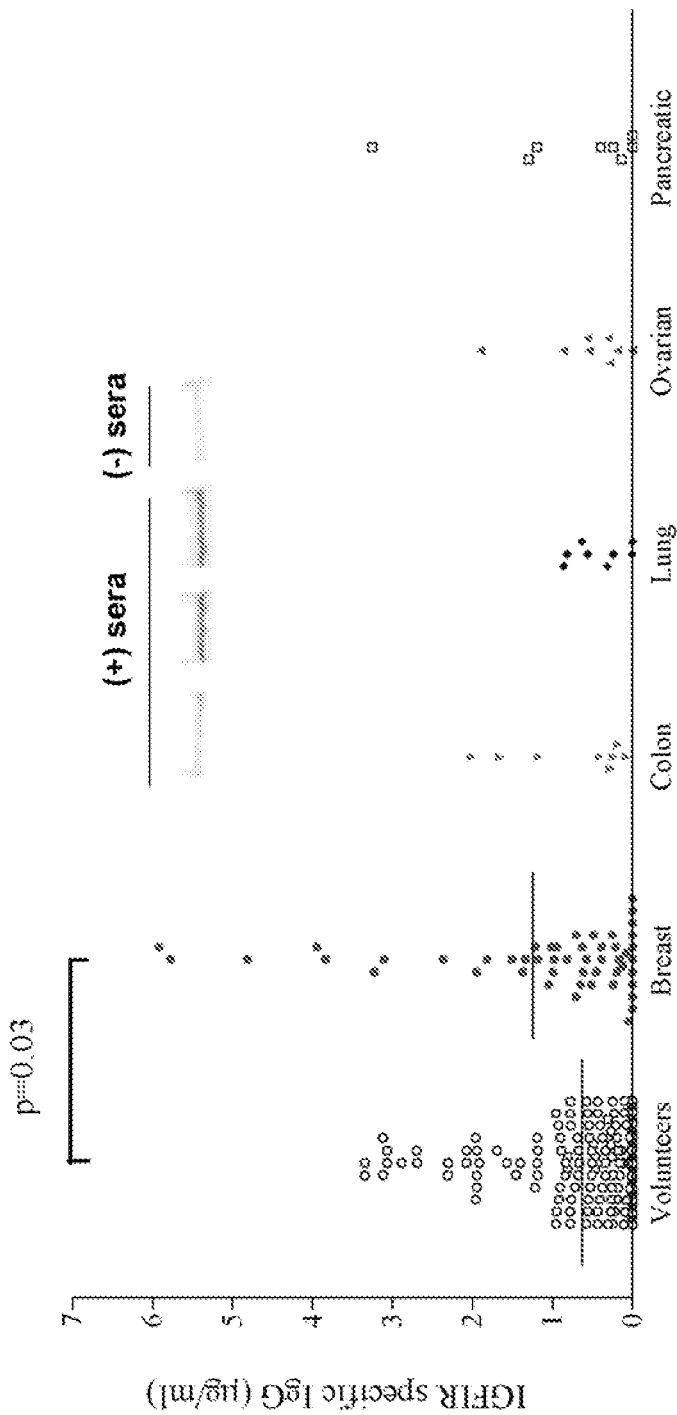
FIG. 16. IGF1R is immunogenic, as shown in this plot of IGF1R specific IgG (in μg/ml) for volunteers as compared to patients having cancer of the breast, colon, lung, ovary or pancreas. A representative western blot comparing positive to negative sera is shown.
Figure 17:
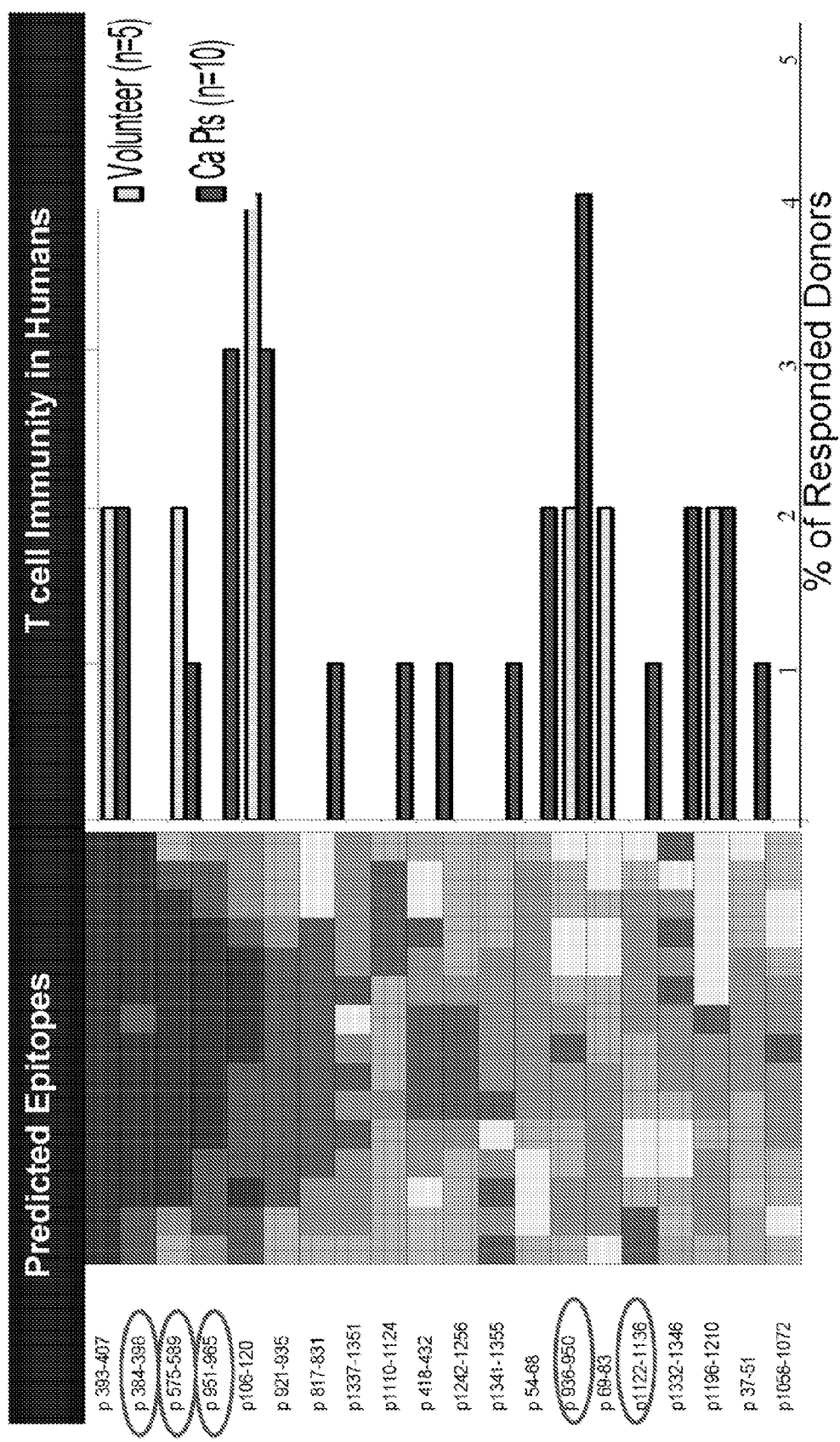
FIG. 17. Immunogenic epitopes derives from IGF1R are shown, with hot spots highlighted with darker shading. The right panel is a bar graph depicting the percent of donors showing a T cell response among volunteers (n=10) and cancer patients (n=5). 14 of the 20 predicted epitopes were immunogenic; 70% in breast cancer patients and 30% in volunteer age matched donors.
Figure 18:
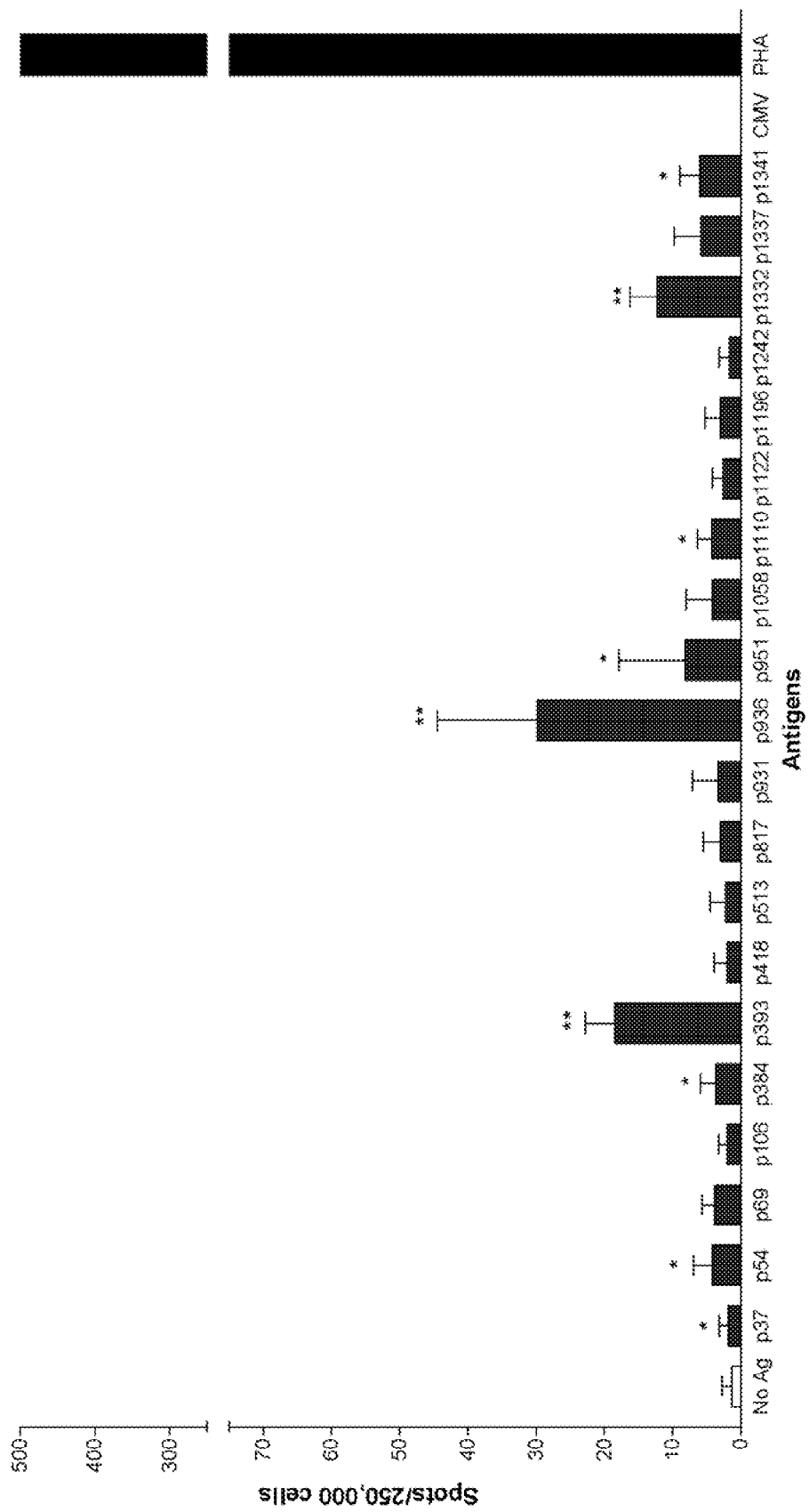
FIG. 18. Representative T cell responses to IGF1R peptides in the majority tested. This bar graph plots number of positive spots per 250,000 cells for various peptides tested. 5 of 15 (33%) showed no response. 7 of 15 (47%) showed a restricted response to up to 3 epitopes. 3 of 15 (20%) showed a polyclonal response to multiple epitopes.
Figures 19A, 19B:
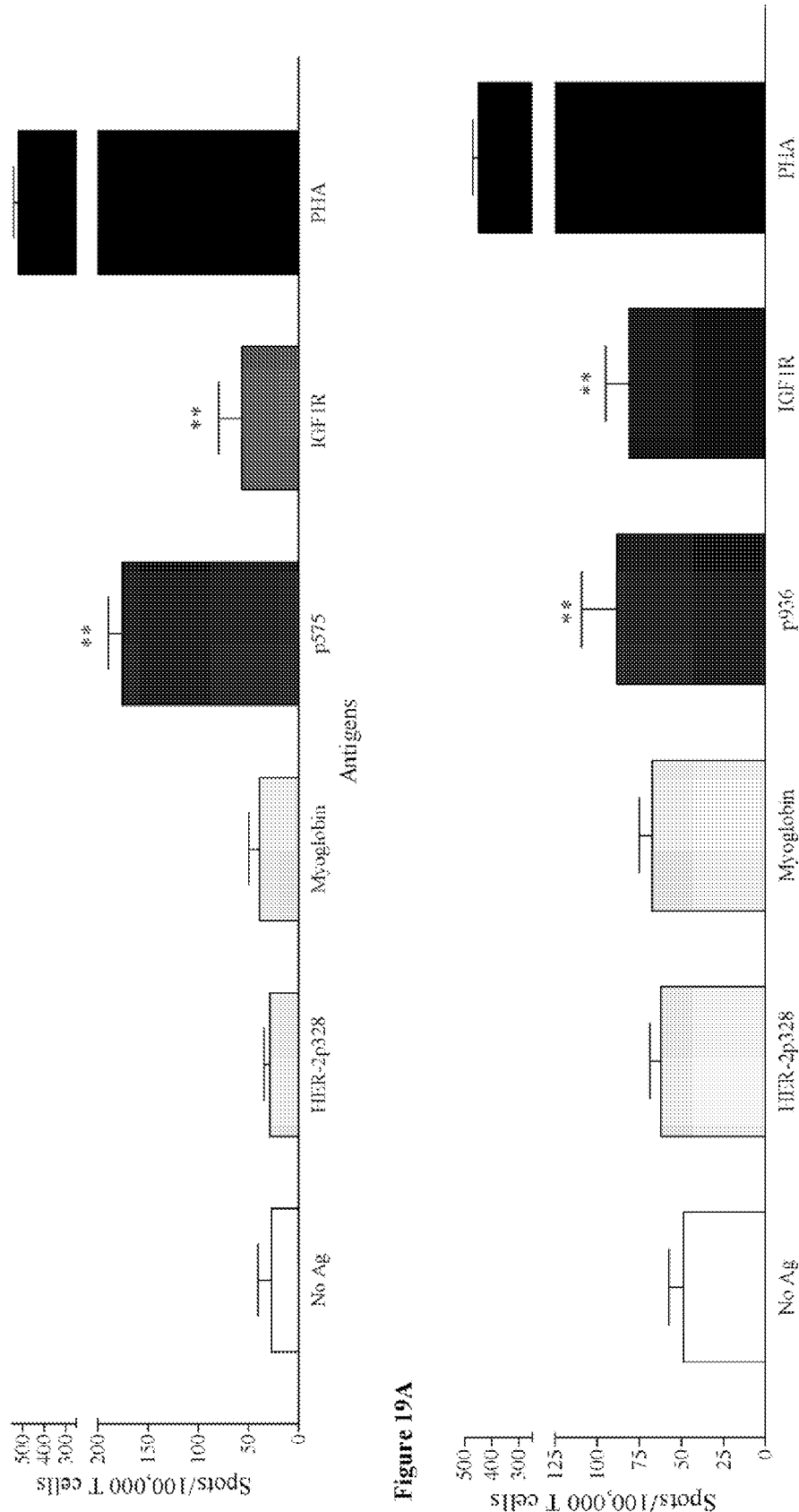
FIG. 19A-B. IGF1R peptide-specific human T cell line. These bar graphs plot the number of positive spots per 100,000 cells in response to no antigen ("No Ag"), HER-2p328, myoglobin, p575 of IGF1R (FIG. 19A) or p936 of IGF1R (FIG. 19B), IGF1R and PHA. ** indicates p<0.05.
Figure 20A:
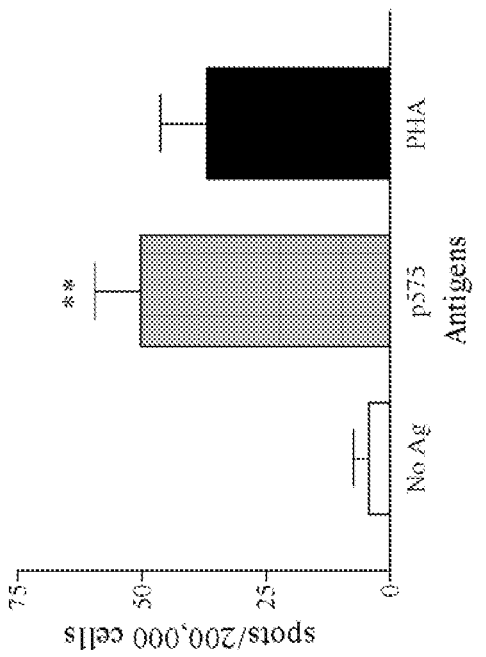
FIG. 20A-E. IGF1R-specific immune responses in vaccinated mice. These bar graphs (FIGS. 20A-D) show the number of spots per 200,000 cells for the tested antigens: no antigen ("No Ag") and PHA are compared to IGF1R peptides: p384 (FIG. 20A), p575 (FIG. 20B), p951 (FIG. 20C), and p1122 (FIG. 20D). IgG in ng/ml for vaccinated mice (FIG. 20E) is compared for prevaccine and post-tumor mice, showing a difference significant at p<0.05.
Figure 20B:
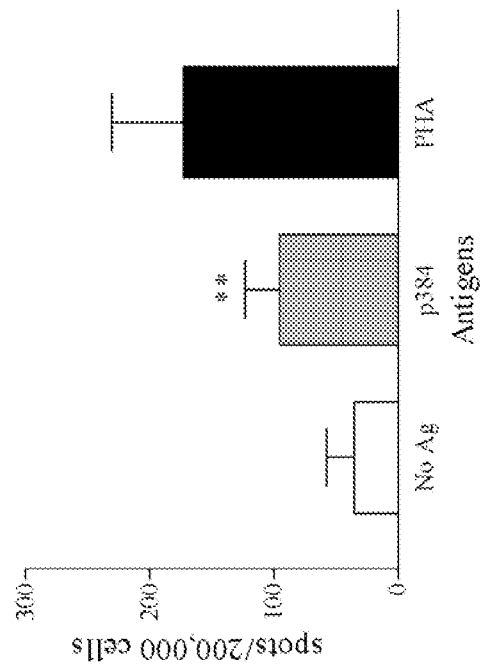
Figure 20C:
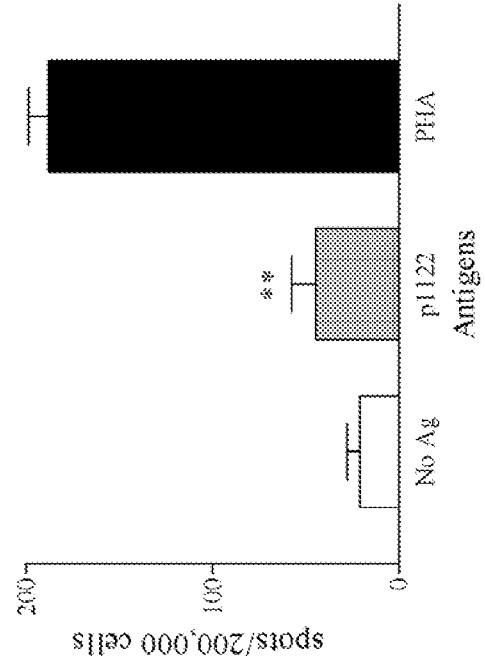
Figure 20D:
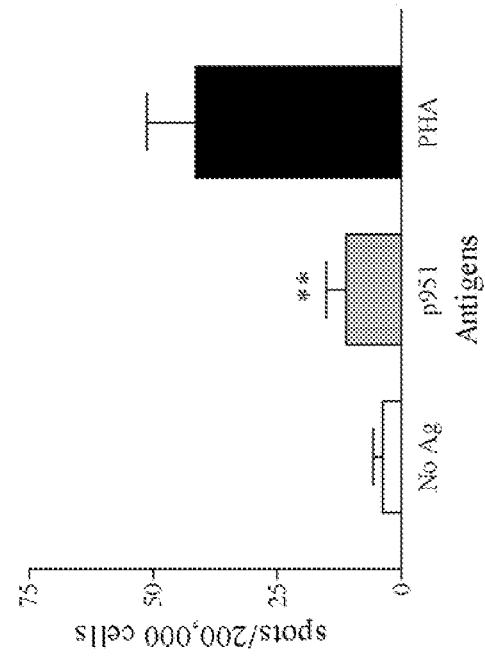
Figure 20E:
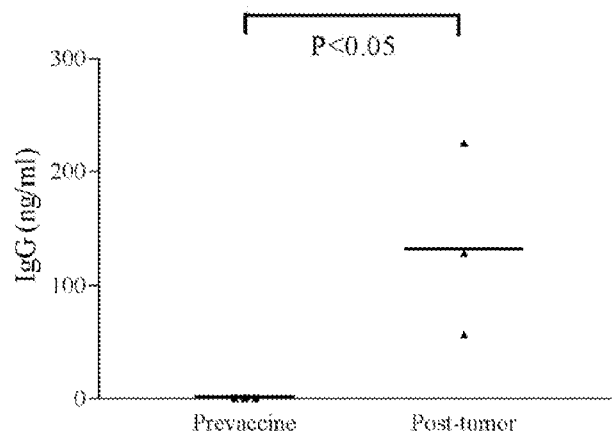

IGFBP-2 peptide vaccination inhibited tumor growth by approximately 50% compared with control groups (FIG. 15C). The differences of mean tumor size between the IGFBP-2 peptide vaccinated group (mean±SD; 671.9±71.1 mm$^3$), tetanus toxoid peptide vaccinated group (mean±SD; 1580.0±97.7 mm$^3$), adjuvant alone (mean±SD; 1511.3±226.0 mm$^3$) and PBS control group (mean±SD; 1562.4±362.6 mm$^3$) were statistically significant (PBS vs. IGFBP-2 vaccine, p=0.035; adjuvant alone vs. IGFBP-2 vaccine, p=0.035; tt peptide vs. IGFBP-2 vaccine, p=0.035). To assess the therapeutic efficacy of IGFBP-2-specific T cells, 1×10$^7$ of in vitro cultured IGFBP-2 peptide specific T cells were adoptively transferred to 10-day tumor bearing mice. A single infusion of IGFBP-2 specific T cells inhibited tumor growth by 60% (FIG. 15D). Twenty eight days after T cell transfer, the mean tumor size of the IGFBP-2 specific T cell treated group (mean±SD; 690.5±231 mm$^3$) was significantly different from that of animals receiving an equal dose infusion of naïve splenocytes (mean±SD; 1751.4±90.0 mm$^3$, p=0.015).

Discussion

Insulin like growth factor binding proteins, such as IGFBP-2, transport IGFs from the circulation into tissues and are part of an important regulatory network controlling cell proliferation, migration, and apoptosis (21). IGFBP-2 is one of six IGFBPs and is found at elevated levels in the sera of cancer patients (22-24). Studies have demonstrated that IGFBP-2 has an IGF independent growth stimulatory effect on tumor cells, directly promoting cell growth while inhibiting apoptosis (25). More recently IGFBP-2 has been shown to act as a regulatory protein for PTEN in breast cancer cells (13). Elevated levels of IGFBP-2 prevent PTEN interaction with IGFR-II, thus resulting in enhanced cell proliferation via activation of the PI3K/Akt signaling pathway. In breast cancer, IGFBP-2 expression has not been found in normal glandular tissue but has been found in increasing levels in pre-malignant and malignant disease with the highest levels associated with invasive ductal carcinomas (10). We questioned whether IGFBP-2 might be a target for immunomodulation in breast cancer and whether the ability to recognize IGFBP-2 was within the realm of the human T cell repertoire. Data presented here demonstrate that not only is IGFBP-2 a human tumor antigen but also that an IGFBP-2-specific T cell response may impact tumor growth in vivo, i.e. the protein may function as a tumor rejection antigen in breast cancer.

Initially we evaluated whether patients with breast cancer developed IGFBP-2 IgG antibody immunity which we theorized would be a marker for a potential cellular immune response (26, 27) as immunoglobulin class switching from IgM to IgG requires cognate CD4$^+$ T-cell help.

Moreover, it has been shown that tumor antigen-specific antibody immunity is positively associated with a concomitant antigen-specific T-cell response, indicating that IgG immunity may act as a marker for the presence of CD4$^+$ and CD8$^+$ T-cell immunity (28, 29). Previous work by our group demonstrated that those peptides most likely to be native epitopes of the tumor antigen HER-2/neu bound at high affinity across multiple class II alleles (16). For this reason, we analyzed the IGFBP-2 protein sequence using 5 class II prediction algorithms across multiple class II alleles and developed a scoring system that would maximize the identification of peptides with predicted promiscuous high affinity class II binding. The majority of peptides identified in this fashion elicited a T cell response, indicating this approach may be a useful tool in class II epitope prediction.

The identified IGFBP-2 class II peptides demonstrated a high degree of homology with common bacterial pathogens. As a comparison, HER-2/neu peptides shown to elicit T cell responses in vitro and in vivo did not demonstrate such structural similarity to bacterial antigens, nor have these HER-2/neu peptides been shown to be immunogenic in non-tumor bearing individuals (30). Structural similarities between sequences derived from microorganisms and self epitopes has been termed "molecular mimicry," which is a suggested explanation for some autoimmune diseases (31). Indeed, T cell specificities that are cross reactive with both self and bacterial antigens have been implicated in the pathogenesis of diabetes and multiple sclerosis (32, 33). Molecular mimicry of peptide sequences derived from foreign organisms with self tumor antigens has been identified as one potential reason for the immunogenicity of melanoma antigens such as MART-1 (34). A dominant HLA-A2 class I epitope derived from MART-1 and capable of eliciting cytotoxic T cells with the ability to lyse tumor was highly homologous and cross reactive with an HSV-1 peptide. It is unknown what role molecular mimicry plays in the immunogenicity of IGFBP-2. The high incidence of detectable immunity in non-tumor bearing individuals, however, would suggest that the T cell responses observed may not be due entirely to autoimmunization via exposure to an IGFBP-2 expressing malignancy.

The neu-transgenic mouse model was used to address whether the immunogenicity of IGFBP-2 in patients with breast cancer also means that this immune response has an impact on tumor growth. Neu-transgenic mice are engineered to express non-transforming rat neu on an MMTV promoter (35). The breast cancer that occurs in these mice is histologically similar to breast cancer in humans. Hyperplastic lesions progress to infiltrating ductal carcinomas, which commonly metastasize to local lymph nodes and soft tissue sites. Moreover, the tumors that develop are estrogen receptor low and demonstrate tamoxifen resistance (36). IGFBP-2 is expressed in these tumors. Both active immunization with IGFBP-2 peptides as well as adoptive transfer of IGFBP-2 competent T cells mediated an anti-tumor response in treated mice as compared to controls. Therefore, IGFBP-2 is a tumor rejection antigen in neu-transgenic mice. Although results in mice cannot be directly comparable to humans, the model has many immunologic similarities with human breast cancer. T regulatory cells are operative in dampening immunity to the neu antigen (37); therefore, immunization against IGFBP-2 circumvented tolerance. T regulatory cells have been shown to play an important role in the progression of human breast cancer (38). Inflammatory infiltrates develop as the tumor progresses in neu transgenic mice (39) just as such infiltrates develop in human breast cancers (40). Finally, the antigenic repertoire in the neu-transgenic mouse appears to be quite similar to that found in patients with malignancy (39). Thus, these studies support the development of a vaccine targeting IGFBP-2 in patients with breast cancer.

Despite an increasing identification of human tumor antigens there is still little insight as to which targets may potentially elicit an anti-tumor response. Indeed, evidence in murine models suggests that some tumor-associated proteins may actually serve to inhibit immunity by inducing the elaboration of T regulatory cells in an attempt to prevent an autoimmune response (41). There is a need for the identification of biologically relevant immunogenic proteins that may ultimately serve as tumor rejection antigens. IGFBP-2 has a direct growth stimulating effect on breast cancer cells, is expressed in a majority of breast cancers, is immunogenic in breast cancer patients, and immunity against the protein can mediate tumor regression. Therefore, IGFBP-2 appears to be an essential target for breast cancer immunomodualtion.

REFERENCES

1. Finn, O. J. 2003. *Nat Rev Immunol* 3:630-641.
2. Day, R. S., et al. 2005. *Br J Cancer* 92:47-54.
3. Disis, M. L., et al. 2000. *Breast Cancer Res Treat* 62:245-252.
4. Peoples, G. E., et al. 2005. *J Clin Oncol* 23:7536-7545.
5. Czerniecki, B. J., et al. 2007. *Cancer Res* 67:1842-1852.
6. Salazar, L. G., et al. 2004. *AACR Meeting Proc.* 45. (Abstr.)
7. Montgomery, R. B., et al. 2005. *Cancer Res* 65:650-656.
8. Kamb, A., et al. 2007. *Nat Rev Drug Discov* 6:115-120.
9. Pollak, M. N., et a. 2004. *Nat Rev Cancer* 4:505-518.
10. Busund, L. T., et al. 2005. *J Clin Pathol* 58:361-366.
11. Mehrian-Shai, R., et al. 2007. *Proc Natl Aced Sci USA* 104:5563-5568.
12. Martin, J. L., and Baxter, R. C. 2007. *Endocrinology* 148:2532-2541.
13. Perks, C. M., et al. 2007. *Oncogenel* 26(40):5966-572.
14. Disis, M. L., et al. 2006. *J Immunol Methods* 308:13-18.
15. Disis, M. L., et al. 2004. *J Clin Oncol* 22:1916-1925.
16. Salazar, L. G., et al. 2003. *Clin Cancer Res* 9:5559-5565.
17. Lu, J., and Celis, E. 2000. *Cancer Res* 60:5223-5227.
18. Bui, H. H., et al. 2005. *Immunogenetics* 57:304-314.
19. Knutson, K. L., and Disis, M. L. 2004. *Clin Exp Immunol* 135:322-329.
20. Knutson, K. L., et al. 2006. *J Immunol* 177:1526-1533.
21. Samani, A. A., et al. 2007. *Endocr Rev* 28:20-47.
22. Baron-Hay, S., et al. 2004. *Clin Cancer Res* 10:1796-1806.
23. Yu, H., et al. 2001. *Urology* 57:471-475.
24. Renehan, A. G., et al. 2000. *Br J Cancer* 83:1344-1350.
25. Schutt, B. S., et al. 2004. *J Mol Endocrinol* 32:859-868.
26. Nakatsura, T., et al. 2002. *Eur J Immunol* 32:826-836.
27. Di Modugno, F., et al. 2004. *Int J Cancer* 109:909-918.
28. Gnjatic, S., et al. 2003. *Proc Natl Acad Sci USA* 100:8862-8867.
29. Jager, D., et al. 2004. *Cancer Immunol Immunother* 53:144-147.
30. Disis, M. L., et al. 2002. *J Clin Oncol* 20:2624-2632.
31. Blank, M., et al. 2007. *Clin Rev Allergy Immunol* 32:111-118.
32. Uemura, Y., et al. 2003. *J Immunol* 170:947-960.
33. Croxford, J. L., et al. 2005. *J Virol* 79:8581-8590.
34. Loftus, D. J., et al. 1996. *J Exp Med* 184:647-657.
35. Guy, C. T., et al. 1992. *Proc Natl Acad Sci USA* 89:10578-10582.
36. Menard, S., et al. 2000. *Cancer Res* 60:273-275.
37. Knutson, K. L., et al. 2006. *J Immunol* 177:84-91.
38. Bates, G. J., et al. 2006. *J Clin Oncol* 24:5373-5380.
39. Lu, H., et al. 2006. *Cancer Res* 66:9754-9761.
40. Hussein, M. R., and Hassan, H. I. 2006. *J Clin Pathol* 59:972-977.
41. Nishikawa, H., et al. 2003. *Proc Natl Acad Sci USA* 100:10902-10906.

Example 6

Immunogenic Peptides Derived From IGF1Receptor

A scoring system based on internet available epitope prediction algorithms was developed to predict the peptides derived from IGF1R that have optimal binding affinity and promiscuity against multiple MHC class II molecules. Using T lymphocytes in peripheral blood mononuclear cells derived from 10 cancer patients (breast and ovarian cancer) and 5 age matched volunteer donors, we identified 7 peptides derived from the IGF1R protein sequence that stimulated immunity in cancer patients, thus, demonstrating that the ability to recognize IGF1R is within the realm of the human T cell repertoire. After stimulating human T cells with the peptides, IFN-gamma secretion was determined via ELISPOT analysis. Five of the most immunogenic peptides were selected for in vivo evaluation in neu-transgenic mice to assess the potential of clinical efficacy.

```
Amino acid sequence of human IGF1R (SEQ ID NO: 35):
  1 mksgsgggsp tslwgllfls aalslwptsg eicgpgidir ndyqqlkrle nctviegylh 61 illiskaedy rsyrfpkltv iteylllfrv agleslgdlf pnltvirgwk ifynyalvif 121 emtnlkdigl ynlrnitrga irieknadlc ylstvdwsli ldavsnnyiv gnkppkecgd 181 lcpgtmeekp mcekttinne ynyrcwttnr cqkmcpstcq kractennec chpeclgscs
```

-continued

```
 241 apdndtacva crhyyyagvc vpacppntyr fegwrcvdrd fcanilsaes sdsegfvihd
 301 gecmqecpsg firngsqsmy cipcegpcpk vceeekktkt idsvtsaqml qgctifkgnl
 361 linirrgnni aselenfmgl ievvtgyvki rhshalvsls flknlrlilg eeqlegnysf
 421 yvldnqnlqq lwdwdhrnlt ikagkmyfaf npklcvseiy rmeevtgtkg rqskgdintr
 481 nngerasces dvlhftsttt sknriiitwh ryrppdyrdl isftvyykea pfknvteydg
 541 qdacgsnswn mvdvdlppnk dvepgillhg lkpwtqyavy vkavtltmve ndhirgakse
 601 ilyirtnasv psipldvlsa snsssqlivk wnppslpngn lsyyivrwqr qpqdgylyrh
 661 nycskdkipi rkyadgtidi eevtenpkte vcggekgpcc acpkteaekq aekeeaeyrk
 721 vfenflhnsi fvprperkrr dvmqvanttm ssrsrnttaa dtynitdpee leteypffes
 781 rvdnkertvi snlrpftlyr idihscnhea eklgcsasnf vfartmpaeg addipgpvtw
 841 eprpensifl kwpepenpng lilmyeikyg sqvedqrecv srqeyrkygg aklnrlnpgn
 901 ytariqatsl sgngswtdpv ffyvqaktgy enfihijial pvavllivgg lvimlyvfhr
 961 krnnsrlgng vlyasvnpey fsaadvyvpd ewevarekit msrelgqgsf gmvyegvakg
1021 vvkdepetrv aiktvneaas mrerieflne asvmkefnch hvvrllgvvs qgqptlvime
1081 lmtrgdlksy irsirpemen npvlappsls kmiqmageia dgmaylnank fvhrdlaarn
1141 cmvaedftvk igdfgmtrdi yetdyyrkgg kgllpvrwms peslkdgvft tysdvwsfgv
1201 vlweiatlae qpyqglsneq vlrfvmeggl ldkpdncpdm lfelmrmcwq ynpkmrpsfl
1263 eiissikeem epgfrevsfy yseenklpep eeldlepenm esvpldpsas ssslplpdrh
1321 sghkaengpg pgvlvlrasf derqpyahmn ggrkneralp lpqsstc
```

Example 7

IGF1R Specific Humoral Immunity in Cancer Patients

Figure 10:
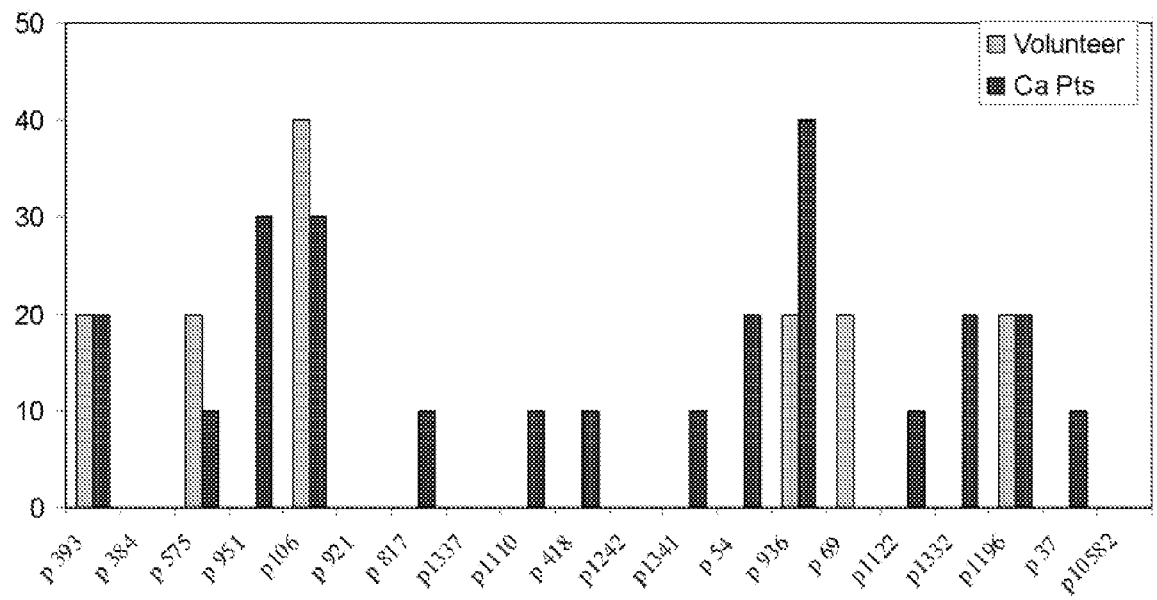
FIG. 10. Bar graph depicting T cell immunity to IGF1R peptides in volunteers and cancer patients (% with response).

This example demonstrates a method to screen for IGF1R specific humoral immunity. As the whole IGF1R protein is too large to be expressed in a bacterial system, we fragmented the cDNA and subcloned to pQE-Trisystem expression vector. Results of these experiments provide evidence of pre-existent immunity to IGF1R in cancer patients. FIG. 10 is a bar graph showing T cell immunity to various IGF1R peptides in normal volunteers and cancer patients. The following Table lists the top 20 epitopes from IFG1R and their corresponding immunogenicity scores.

| Peptide position | Peptide sequences (SEQ ID NO: 36-55) | Immunogenicity Cancer | Volunteer | Homology with murine IGF1R | Final rank scores |
|---|---|---|---|---|---|
| p 393-407 | SHALVSLSFLKNLRL | 2/10 | 2/5 | 100% | 28100 |
| p 384-398 | VVTGYVKIRHSHALV | | | 100% | 27961 |
| p 575-589 | TQYAVYVKAVTLTMV | 1/10 | 1/5 | 100% | 25421 |
| p 951-965 | LVIMLYVFHRKRNNS | 3/10 | | 100% | 23477 |
| p 106-120 | IRGWKLFYNYALVIF | 3/10 | 2/5 | 100% | 20507 |
| p 921-935 | FFYVQAKTGYENFIH | | | 80% | 15161 |
| p 817-831 | ASNFVFARTMPAEGA | 1/10 | | 100% | 13881 |
| p 1337-1351 | RASFDERQPYAHMNG | | | 100% | 12314 |
| p 1110-1124 | SKMIQMAGEIADGMA | 1/10 | | 100% | 11792 |
| p 418-432 | YSFYVLDNQNLQQLW | 1/10 | | 100% | 11216 |
| p 1242-1256 | FELMRMCWQYNPKMR | | | 100% | 11119 |
| p 1341-1355 | DERQPYAHMNGGRKN | 1/10 | | 100% | 10928 |

-continued

| Peptide position | Peptide sequences (SEQ ID NO: 36-55) | Immunogenicity Cancer | Immunogenicity Volunteer | Homology with murine IGF1R | Final rank scores |
|---|---|---|---|---|---|
| p 54-68 | VIEGYLHILLISKAE | 2/10 | | 93% | 10548 |
| p 936-950 | LIIALPVAVLLIVGG | 4/10 | 1/5 | 93% | 10456 |
| p 69-83 | DYRSYRFPKLTVITE | | 1/5 | 100% | 10198 |
| p 1122-1136 | GMAYLNANKFVHRDL | 1/10 | | 100% | 10051 |
| p 1332-1346 | GVLVLRASFDERQPY | 2/10 | | 100% | 9675 |
| p 1196-1210 | WSFGVVLWEIATLAE | 2/10 | 1/5 | 100% | 9508 |
| p 37-5 | IDIRNDYQQLKRLEN | 1/10 | | 100% | 9032 |
| p 1058-1072 | NCHHVVRLLGVVSQG | | | 100% | 8521 |

Example 8

IGF1R Vaccine

Figure 22:
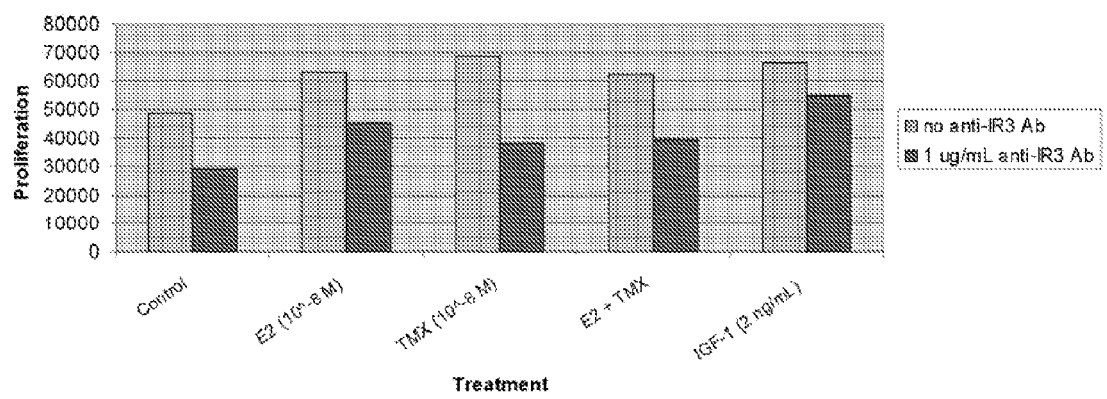
FIG. 22. This bar graph shows that blocking IGF1R inhibits mucosal mast cell (MMC) growth. Proliferation is plotted for MMC treated with no anti-IR3 antibody or 1 μg/ml anti-IR3 antibody under control conditions, treatment with E2, treatment with tamoxifen ("TMX"), treatment with both E2 and tamoxifen, and treatment with IGF-1. The MMC used are tamoxifen-resistant. The results show that the growth stimulatory effect of E2 and tamoxifen can be inhibited by anti-IR3.
Figure 21:
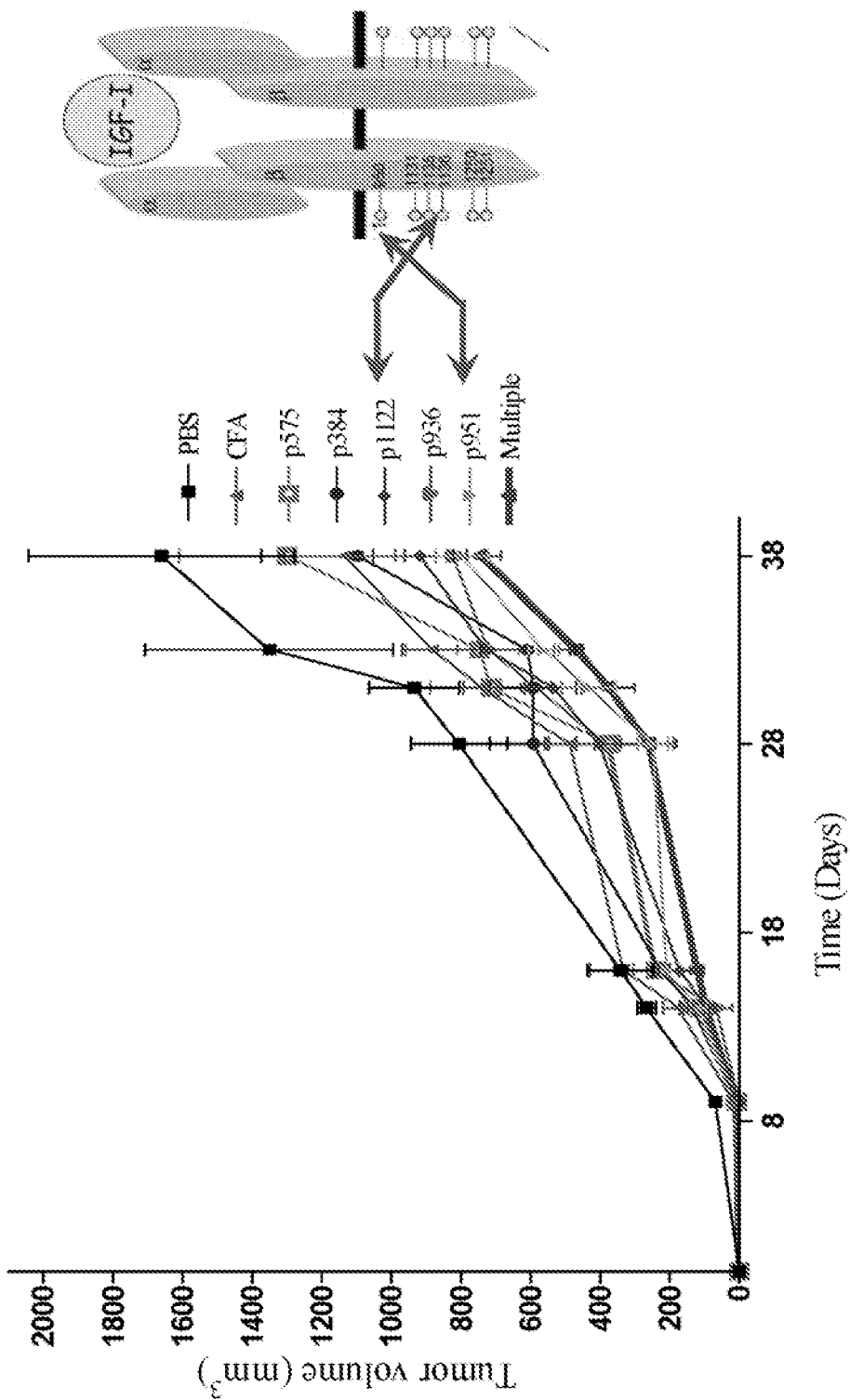
FIG. 21. Plot of tumor volume in mm³ over time in days for PBS, CFA, p575, p384, p1122, p936, p951 and the multiple peptide vaccine shows that vaccination with multiple peptides is better.
Figure 23:
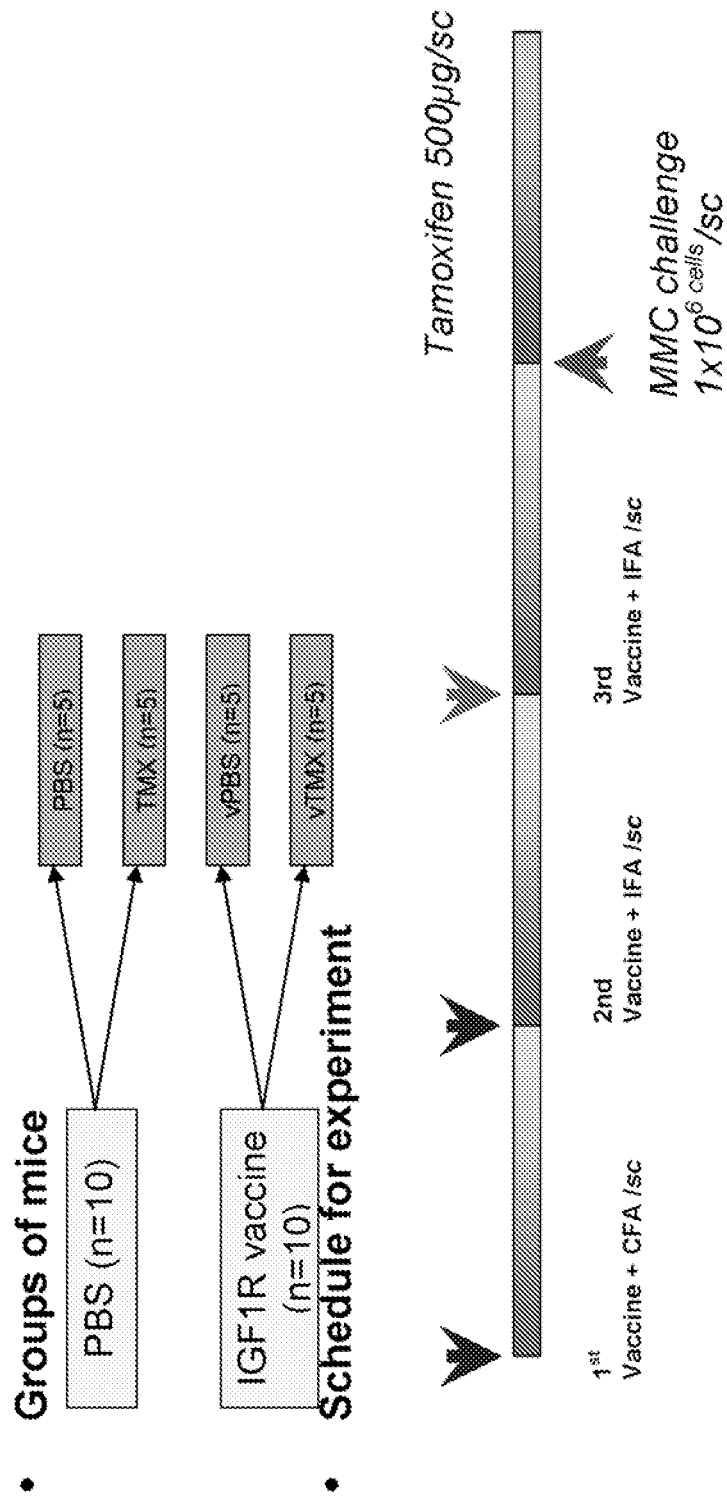
FIG. 23. Schematic illustration of IGF1R vaccine/tamoxifen study.
Figure 24:
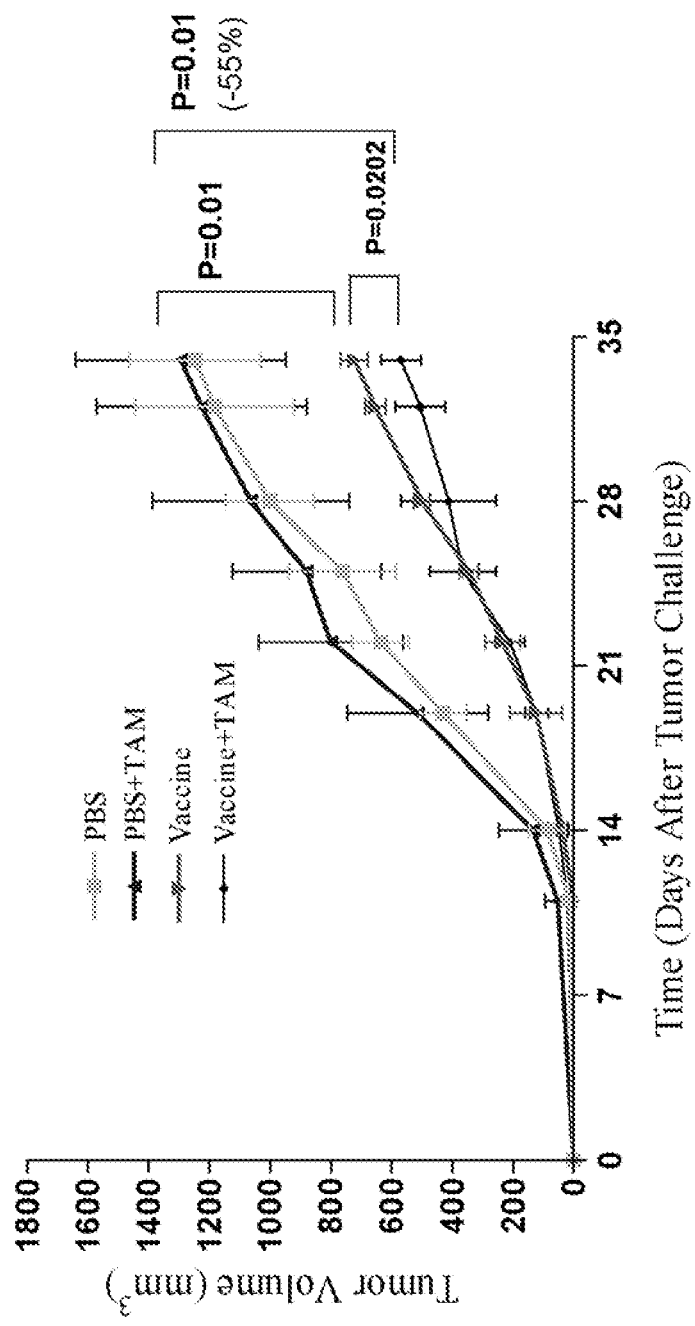
FIG. 24. Graph of tumor volume in mm$^3$ over time in days after tumor challenge. The results show the impact of immunization with IGF1R vaccine on tamoxifen sensitivity.
Figure 25:
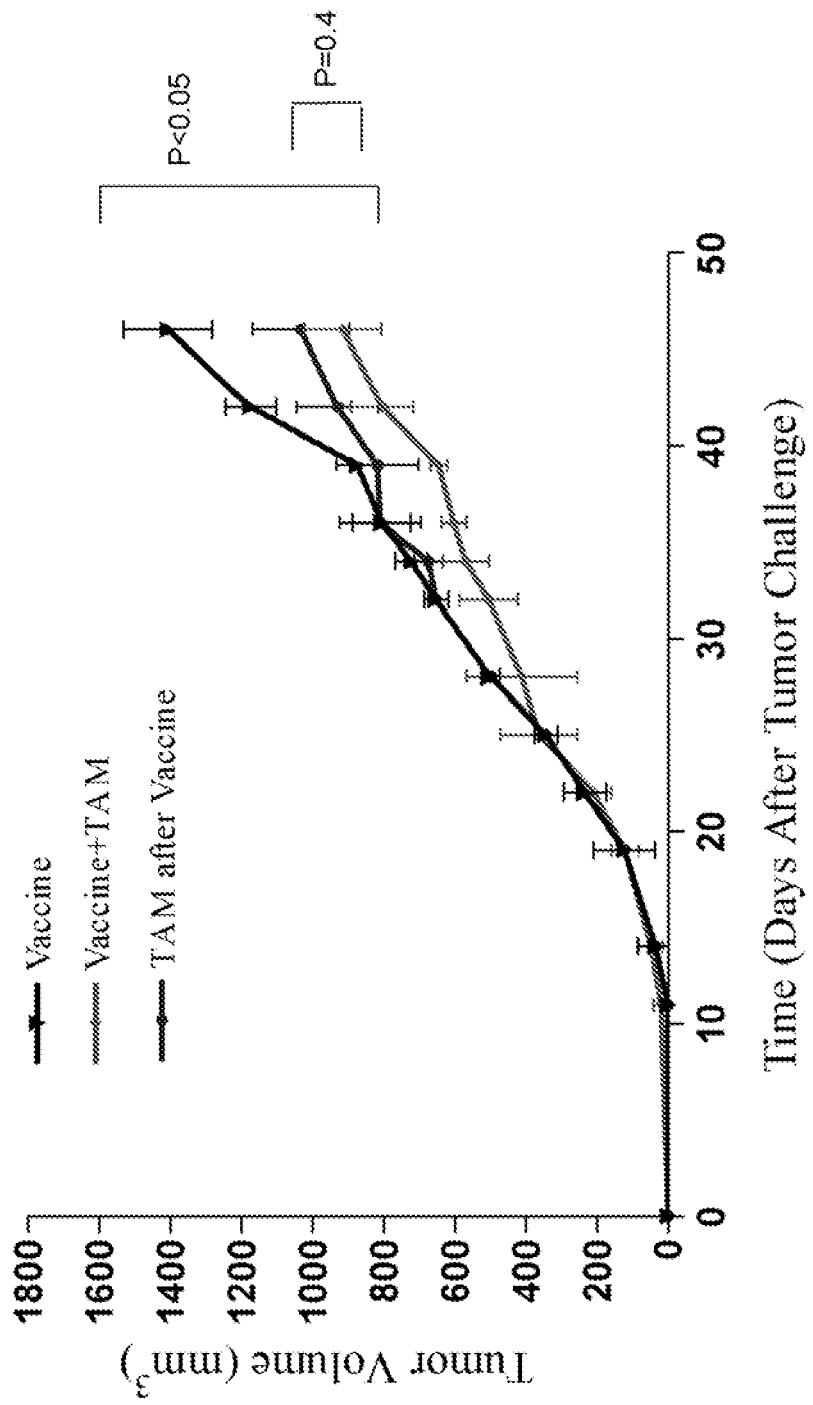
FIG. 25. Graph of tumor volume in mm$^3$ over time in days after tumor challenge. In this study, all groups received IFG1R vaccine on the same schedule. The "vaccine" group received a control treatment that overlapped with the latter part of the vaccine treatment and continued for a period extending beyond the vaccine treatment. In the "vaccine+ TAM" group, tamoxifen treatment (500 μg/day s.c.) overlapped with and extended beyond the vaccine treatment period (tamoxifen treatment on the same schedule as the control treatment of the first group). The "TAM after vaccine" group was given control treatment during the overlap period and for the initial period extending beyond the vaccine treatment, but then, for the latter part of the treatment, tamoxifen was administered.
Figure 26A:
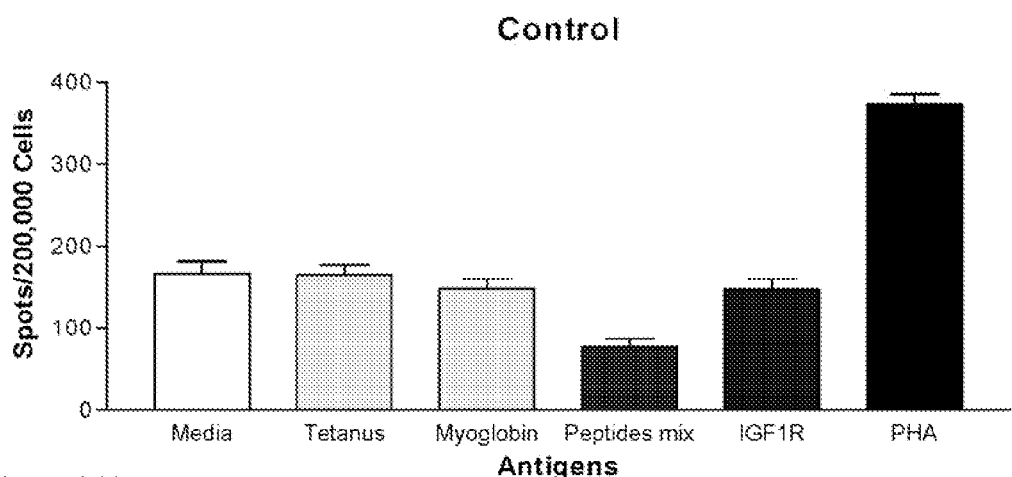
Figure 26B:
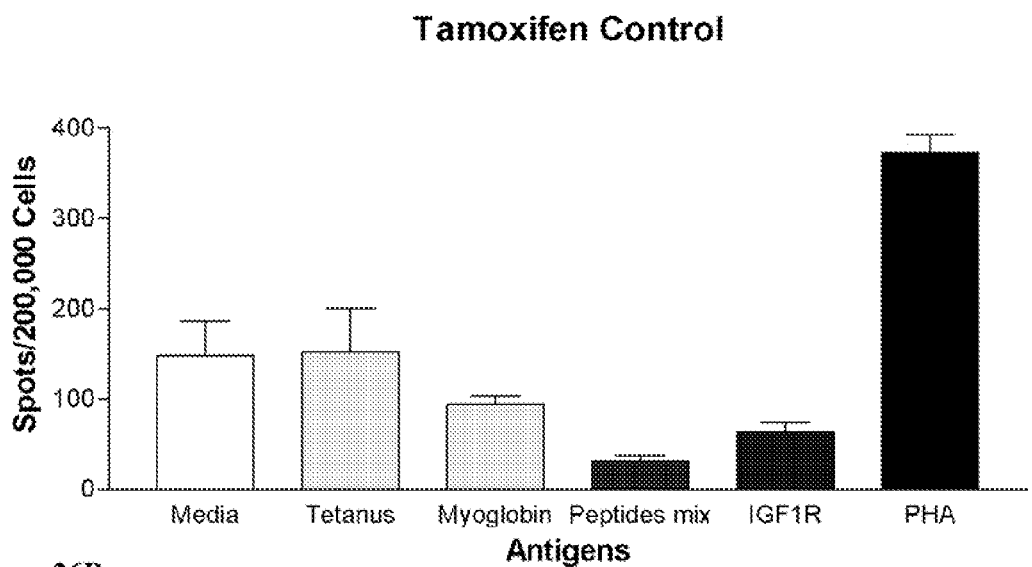
Figure 26C:
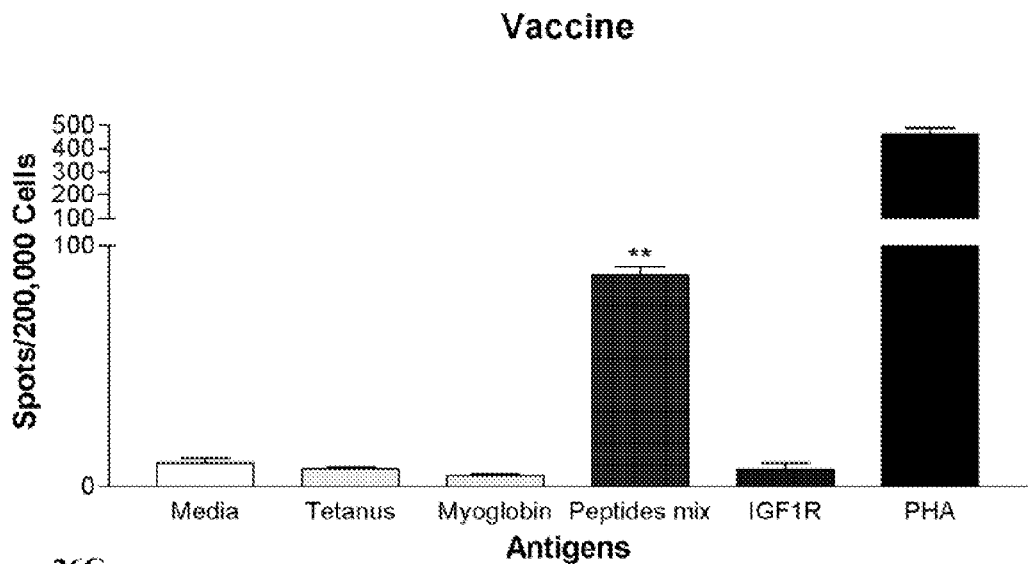
Figure 27E:
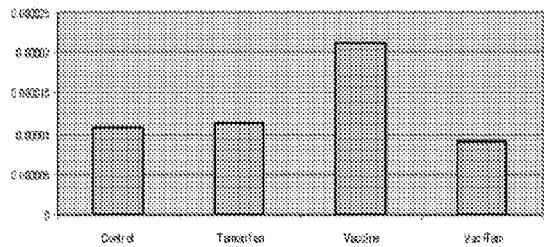
Figure 27F:
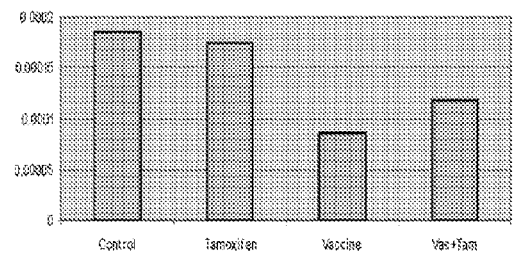
Figure 28:
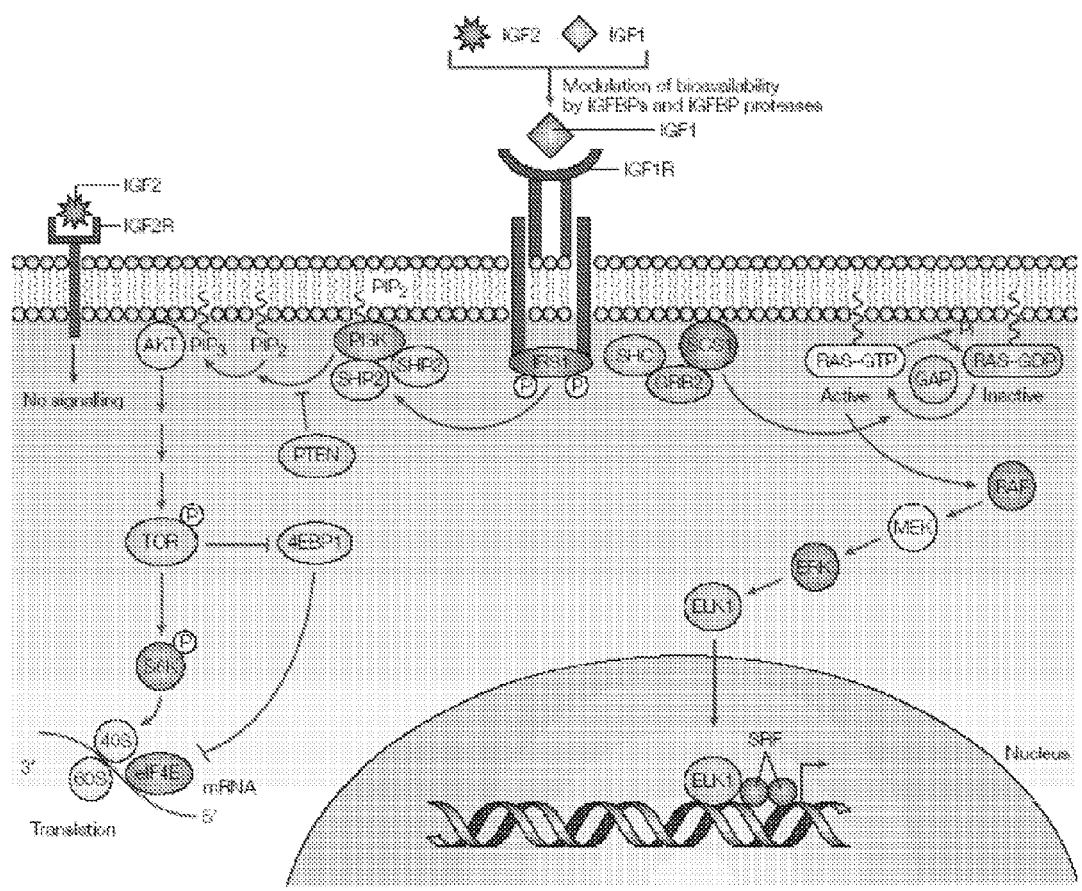
FIG. 28. Schematic illustration of IGF1R regulation and signaling. As discussed in Perks et al., Oncogene 2007, IGF1R activity modulates IGFBP-2/PTEN.
Figure 29A:
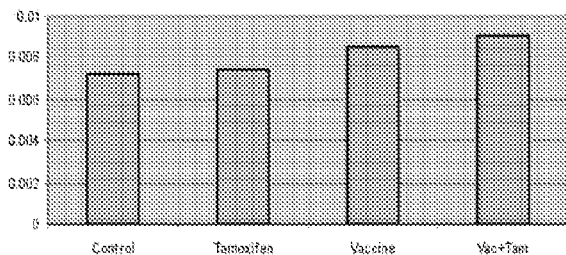
FIG. 29A-E. Bar graphs indicating growth pathway signals for control, tamoxifen control, vaccine and tamoxifen+vaccine conditions. IGF1R, FIG. 29A; ErbB2, FIG. 29B; ER-α, FIG. 29C; IGFBP2, FIG. 29D; PTEN, FIG. 29E. Shown in lower portion of FIGS. 29D-E are representative blots comparing IGFBP2 (FIG. 29D) or PTEN (FIG. 29E) and β-actin.
Figure 29B:
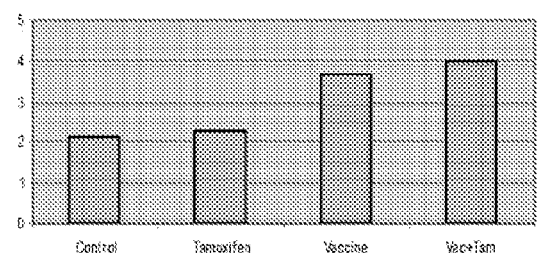
Figure 29C:
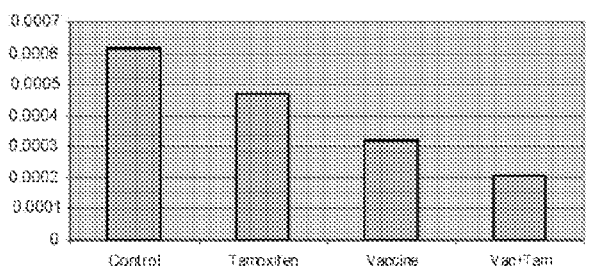
Figure 29D:
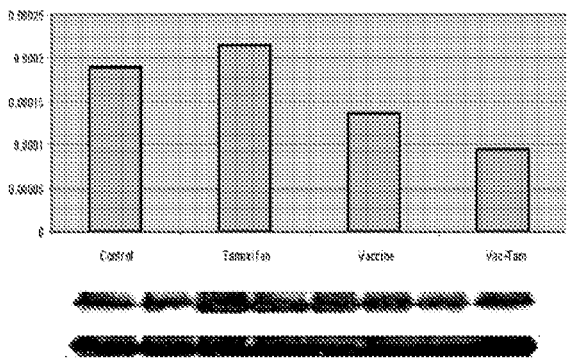
Figure 29E:
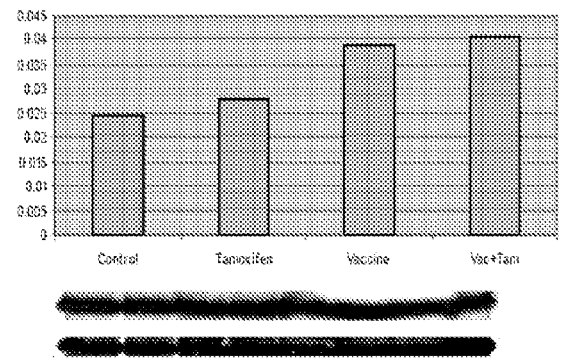

This example demonstrates that IGF1R and immunogenic epitopes derived from IGF1R elicit specific responses in human T cells and in vaccinated mice. The data are presented in FIGS. 16 through 29 (see Brief Description of Figures above). Not only do IGF1R peptides effectively reduce tumor volume (FIG. 21), but blocking IGF1R inhibits growth of tamoxifen-resistant MMC (FIG. 22). Immunization with IGF1R increases tamoxifen sensitivity (FIGS. 23-26) and influences immunologic signaling (FIG. 27) and growth pathway signals (FIG. 29).

Throughout this application various publications are referenced. The disclosures of these publications in their entireties are hereby incorporated by reference into this application in order to describe more fully the state of the art to which this invention pertains.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An immunogenic peptide comprising an immunogenic fragment of an IGFBP2 polypeptide comprising the amino acid sequence of SEQ ID NO: 1 and a pharmaceutically acceptable carrier, wherein the immunogenic fragment consists of the amino acid sequence of SEQ ID NO: 14.

2. A pharmaceutical composition comprising the peptide of claim 1 and a pharmaceutically acceptable carrier.

3. The pharmaceutical composition of claim 2 further comprising an adjuvant.

4. The immunogenic peptide of claim 1 further comprising the amino acid sequence of a heterologous peptide.

5. The immunogenic peptide of claim 4, wherein the amino acid sequence of the heterologous peptide comprises the amino acid sequence of T helper epitope.

6. The immunogenic peptide of claim 4, wherein the amino acid sequence of the heterologous peptide comprises the amino acid sequence of an immunogenic fragment of an IGF1R polypeptide comprising the amino acid sequence of SEQ ID NO: 35.

7. The immunogenic peptide of claim 6, wherein the amino acid sequence of the immunogenic fragment of the IGF1R polypeptide is selected from SEQ ID NOs: 36-55.

8. The immunogenic peptide of claim 1 further comprising one or more additional immunogenic fragments of the IGFBP2 polypeptide comprising a MHC class II binding epitope, wherein said additional immunogenic fragments consist of an amino acid sequence selected from SEQ ID NOs: 2-13 and 15.

9. The immunogenic peptide of claim 1 further comprising one or more additional immunogenic fragments of the IGFBP2 polypeptide comprising an HLA-A2 binding epitope, wherein said additional immunogenic fragments consist of an amino acid sequence selected from SEQ ID NOs: 16-22.

10. A nucleic acid molecule encoding an immunogenic peptide comprising an immunogenic fragment of an IGFBP2 polypeptide comprising the amino acid sequence of SEQ ID NO: 1 and a pharmaceutically acceptable carrier, wherein the immunogenic fragment consists of the amino acid sequence of SEQ ID NO: 14.

11. A pharmaceutical composition comprising the nucleic acid of claim 10 and a pharmaceutically acceptable carrier.

12. The pharmaceutical composition of claim 11 further comprising an adjuvant.

13. The pharmaceutical composition of claim 12, wherein the adjuvant is a cytokine.

14. The pharmaceutical composition of claim 11, wherein the nucleic acid is disposed within a plasmid expression vector.

15. The pharmaceutical composition of claim 2 further comprising one or more additional immunogenic peptides comprising an immunogenic fragment of the IGFBP2 polypeptide comprising a MHC class II binding epitope, wherein said immunogenic fragment consists of an amino acid sequence selected from SEQ ID NOs: 2-13 and 15.

16. The pharmaceutical composition of claim 2 further comprising one or more additional immunogenic peptides comprising an immunogenic fragment of the IGFBP2 polypeptide comprising a HLA-A2 class II binding epitope, wherein said immunogenic fragment consists of an amino acid sequence selected from SEQ ID NOs: 16-22.

17. The pharmaceutical composition of claim 2 further comprising one or more additional immunogenic peptides comprising the amino acid sequence of an immunogenic fragment of an IGF1R polypeptide comprising the amino acid sequence of SEQ ID NO: 35.

18. The pharmaceutical composition of claim 17, wherein the amino acid sequence of the immunogenic fragment of the IGF1R polypeptide is selected from SEQ ID NOs: 36-55.

19. An immunogenic peptide comprising an immunogenic fragment of an IGFBP2 polypeptide comprising the amino acid sequence of SEQ ID NO: 1 and a pharmaceutically acceptable carrier, wherein the immunogenic fragment consists of the amino acid sequence of SEQ ID NO: 16.

20. A pharmaceutical composition comprising the peptide of claim 19 and a pharmaceutically acceptable carrier.

21. The pharmaceutical composition of claim 20 further comprising an adjuvant.

22. The immunogenic peptide of claim 19 further comprising the amino acid sequence of a heterologous peptide.

23. The immunogenic peptide of claim 22, wherein the amino acid sequence of the heterologous peptide comprises the amino acid sequence of T helper epitope.

24. The immunogenic peptide of claim 22, wherein the amino acid sequence of the heterologous peptide comprises the amino acid sequence of an immunogenic fragment of an IGF1R polypeptide comprising the amino acid sequence of SEQ ID NO: 35.

25. The immunogenic peptide of claim 24, wherein the amino acid sequence of the immunogenic fragment of the IGF1R polypeptide is selected from SEQ ID NOs: 36-55.

26. The immunogenic peptide of claim 19 further comprising one or more additional immunogenic fragments of the IGFBP2 polypeptide comprising a MHC class II binding epitope, wherein said additional immunogenic fragments consist of an amino acid sequence selected from SEQ ID NOs: 2-15.

27. The immunogenic peptide of claim 19 further comprising one or more additional immunogenic fragments of the IGFBP2 polypeptide comprising an HLA-A2 binding epitope, wherein said additional immunogenic fragments consist of an amino acid sequence selected from SEQ ID NOs: 17-22.

28. A nucleic acid molecule encoding an immunogenic peptide comprising an immunogenic fragment of an IGFBP2 polypeptide comprising the amino acid sequence of SEQ ID NO: 1 and a pharmaceutically acceptable carrier, wherein the immunogenic fragment consists of the amino acid sequence of SEQ ID NO: 16.

29. A pharmaceutical composition comprising the nucleic acid of claim 28 and a pharmaceutically acceptable carrier.

30. The pharmaceutical composition of claim 29 further comprising an adjuvant.

31. The pharmaceutical composition of claim 30, wherein the adjuvant is a cytokine.

32. The pharmaceutical composition of claim 29, wherein the nucleic acid is disposed within a plasmid expression vector.

33. The pharmaceutical composition of claim 29 further comprising one or more additional immunogenic peptides comprising an immunogenic fragment of the IGFBP2 polypeptide comprising a MHC class II binding epitope, wherein said immunogenic fragment consists of an amino acid sequence selected from SEQ ID NOs: 2-15.

34. The pharmaceutical composition of claim 29 further comprising one or more additional immunogenic peptides comprising an immunogenic fragment of the IGFBP2 polypeptide comprising a HLA-A2 class II binding epitope, wherein said immunogenic fragment consists of an amino acid sequence selected from SEQ ID NOs: 17-22.

35. The pharmaceutical composition of claim 29 further comprising one or more additional immunogenic peptides comprising the amino acid sequence of an immunogenic fragment of an IGF1R polypeptide comprising the amino acid sequence of SEQ ID NO: 35.

36. The pharmaceutical composition of claim 35, wherein the amino acid sequence of the immunogenic fragment of the IGF1R polypeptide is selected from SEQ ID NOs: 36-55.

* * * * *

SEQUENCE LISTING

```
<160> NUMBER OF SEQ ID NOS: 55

<210> SEQ ID NO 1
<211> LENGTH: 328
<212> TYPE: PRT
<213> ORGANISM: Homo sapiens

<400> SEQUENCE: 1

Met Leu Pro Arg Val Gly Cys Pro Ala Leu Pro Leu Pro Pro Pro
1               5                   10                  15

Leu Leu Pro Leu Leu Pro Leu Leu Leu Leu Leu Gly Ala Ser Gly
                20                  25                  30

Gly Gly Gly Gly Ala Arg Ala Glu Val Leu Phe Arg Cys Pro Pro Cys
                35                  40                  45

Thr Pro Glu Arg Leu Ala Ala Cys Gly Pro Pro Pro Val Ala Pro Pro
        50                  55                  60

Ala Ala Val Ala Ala Val Ala Gly Gly Ala Arg Met Pro Cys Ala Glu
65                  70                  75                  80

Leu Val Arg Glu Pro Gly Cys Gly Cys Cys Ser Val Cys Ala Arg Leu
                85                  90                  95

Glu Gly Glu Ala Cys Gly Val Tyr Thr Pro Arg Cys Gly Gln Gly Leu
                100                 105                 110

Arg Cys Tyr Pro His Pro Gly Ser Glu Leu Pro Leu Gln Ala Leu Val
            115                 120                 125

Met Gly Glu Gly Thr Cys Glu Lys Arg Arg Asp Ala Glu Tyr Gly Ala
        130                 135                 140
```

Ser Pro Glu Gln Val Ala Asp Asn Gly Asp His Ser Glu Gly Gly
145                 150                 155                 160

Leu Val Glu Asn His Val Asp Ser Thr Met Asn Met Leu Gly Gly Gly
        165                 170                 175

Gly Ser Ala Gly Arg Lys Pro Leu Lys Ser Gly Met Lys Glu Leu Ala
        180                 185                 190

Val Phe Arg Glu Lys Val Thr Glu Gln His Arg Gln Met Gly Lys Gly
        195                 200                 205

Gly Lys His His Leu Gly Leu Glu Glu Pro Lys Lys Leu Arg Pro Pro
    210                 215                 220

Pro Ala Arg Thr Pro Cys Gln Gln Glu Leu Asp Gln Val Leu Glu Arg
225                 230                 235                 240

Ile Ser Thr Met Arg Leu Pro Asp Glu Arg Gly Pro Leu Glu His Leu
                245                 250                 255

Tyr Ser Leu His Ile Pro Asn Cys Asp Lys His Gly Leu Tyr Asn Leu
                260                 265                 270

Lys Gln Cys Lys Met Ser Leu Asn Gly Gln Arg Gly Glu Cys Trp Cys
            275                 280                 285

Val Asn Pro Asn Thr Gly Lys Leu Ile Gln Gly Ala Pro Thr Ile Arg
    290                 295                 300

Gly Asp Pro Glu Cys His Leu Phe Tyr Asn Glu Gln Gln Glu Ala Arg
305                 310                 315                 320

Gly Val His Thr Gln Arg Met Gln
                325

<210> SEQ ID NO 2
<211> LENGTH: 15
<212> TYPE: PRT
<213> ORGANISM: Homo sapiens

<400> SEQUENCE: 2

Leu Leu Pro Leu Leu Pro Leu Leu Leu Leu Leu Gly Ala Ser
1               5                   10                  15

<210> SEQ ID NO 3
<211> LENGTH: 15
<212> TYPE: PRT
<213> ORGANISM: Homo sapiens

<400> SEQUENCE: 3

Gly Pro Leu Glu His Leu Tyr Ser Leu His Ile Pro Asn Cys Asp
1               5                   10                  15

<210> SEQ ID NO 4
<211> LENGTH: 15
<212> TYPE: PRT
<213> ORGANISM: Homo sapiens

<400> SEQUENCE: 4

Glu Leu Ala Val Phe Arg Glu Lys Val Thr Glu Gln His Arg Gln
1               5                   10                  15

<210> SEQ ID NO 5
<211> LENGTH: 15
<212> TYPE: PRT
<213> ORGANISM: Homo sapiens

<400> SEQUENCE: 5

Lys His Gly Leu Tyr Asn Leu Lys Gln Cys Lys Met Ser Leu Asn

```
1               5                   10                  15
```

<210> SEQ ID NO 6
<211> LENGTH: 15
<212> TYPE: PRT
<213> ORGANISM: Homo sapiens

<400> SEQUENCE: 6

```
Pro Asn Thr Gly Lys Leu Ile Gln Gly Ala Pro Thr Ile Arg Gly
1               5                   10                  15
```

<210> SEQ ID NO 7
<211> LENGTH: 15
<212> TYPE: PRT
<213> ORGANISM: Homo sapiens

<400> SEQUENCE: 7

```
Pro Ala Leu Pro Leu Pro Pro Pro Leu Leu Pro Leu Leu Pro
1               5                   10                  15
```

<210> SEQ ID NO 8
<211> LENGTH: 15
<212> TYPE: PRT
<213> ORGANISM: Homo sapiens

<400> SEQUENCE: 8

```
Asp Gln Val Leu Glu Arg Ile Ser Thr Met Arg Leu Pro Asp Glu
1               5                   10                  15
```

<210> SEQ ID NO 9
<211> LENGTH: 15
<212> TYPE: PRT
<213> ORGANISM: Homo sapiens

<400> SEQUENCE: 9

```
Asn His Val Asp Ser Thr Met Asn Met Leu Gly Gly Gly Gly Ser
1               5                   10                  15
```

<210> SEQ ID NO 10
<211> LENGTH: 15
<212> TYPE: PRT
<213> ORGANISM: Homo sapiens

<400> SEQUENCE: 10

```
Pro Glu Cys His Leu Phe Tyr Asn Glu Gln Gln Glu Ala Arg Gly
1               5                   10                  15
```

<210> SEQ ID NO 11
<211> LENGTH: 15
<212> TYPE: PRT
<213> ORGANISM: Homo sapiens

<400> SEQUENCE: 11

```
Gly Gln Gly Leu Arg Cys Tyr Pro His Pro Gly Ser Glu Leu Pro
1               5                   10                  15
```

<210> SEQ ID NO 12
<211> LENGTH: 15
<212> TYPE: PRT
<213> ORGANISM: Homo sapiens

<400> SEQUENCE: 12

```
Leu Gly Leu Glu Glu Pro Lys Lys Leu Arg Pro Pro Pro Ala Arg
1               5                   10                  15
```

```
<210> SEQ ID NO 13
<211> LENGTH: 15
<212> TYPE: PRT
<213> ORGANISM: Homo sapiens

<400> SEQUENCE: 13

Glu Ala Cys Gly Val Tyr Thr Pro Arg Cys Gly Gln Gly Leu Arg
1               5                   10                  15

<210> SEQ ID NO 14
<211> LENGTH: 15
<212> TYPE: PRT
<213> ORGANISM: Homo sapiens

<400> SEQUENCE: 14

Val Ala Ala Val Ala Gly Gly Ala Arg Met Pro Cys Ala Glu Leu
1               5                   10                  15

<210> SEQ ID NO 15
<211> LENGTH: 15
<212> TYPE: PRT
<213> ORGANISM: Homo sapiens

<400> SEQUENCE: 15

Glu Leu Pro Leu Gln Ala Leu Val Met Gly Glu Gly Thr Cys Glu
1               5                   10                  15

<210> SEQ ID NO 16
<211> LENGTH: 9
<212> TYPE: PRT
<213> ORGANISM: Homo sapiens

<400> SEQUENCE: 16

Leu Leu Pro Leu Leu Leu Leu Leu Leu
1               5

<210> SEQ ID NO 17
<211> LENGTH: 9
<212> TYPE: PRT
<213> ORGANISM: Homo sapiens

<400> SEQUENCE: 17

Val Leu Phe Arg Cys Pro Pro Cys Thr
1               5

<210> SEQ ID NO 18
<211> LENGTH: 9
<212> TYPE: PRT
<213> ORGANISM: Homo sapiens

<400> SEQUENCE: 18

Leu Leu Pro Leu Leu Pro Leu Leu Leu
1               5

<210> SEQ ID NO 19
<211> LENGTH: 9
<212> TYPE: PRT
<213> ORGANISM: Homo sapiens

<400> SEQUENCE: 19

Lys Leu Ile Gln Gly Ala Pro Thr Ile
1               5

<210> SEQ ID NO 20
```

<210> SEQ ID NO 20
<211> LENGTH: 9
<212> TYPE: PRT
<213> ORGANISM: Homo sapiens

<400> SEQUENCE: 20

Gln Val Leu Glu Arg Ile Ser Thr Met
1               5

<210> SEQ ID NO 21
<211> LENGTH: 9
<212> TYPE: PRT
<213> ORGANISM: Homo sapiens

<400> SEQUENCE: 21

Ala Leu Pro Leu Pro Pro Pro Pro Leu
1               5

<210> SEQ ID NO 22
<211> LENGTH: 9
<212> TYPE: PRT
<213> ORGANISM: Homo sapiens

<400> SEQUENCE: 22

Glu Leu Ala Val Phe Arg Glu Lys Val
1               5

<210> SEQ ID NO 23
<211> LENGTH: 15
<212> TYPE: PRT
<213> ORGANISM: Homo sapiens

<400> SEQUENCE: 23

Asp Ser Thr Met Asn Met Leu Gly Gly Gly Ser Ala Gly Arg
1               5                   10                  15

<210> SEQ ID NO 24
<211> LENGTH: 15
<212> TYPE: PRT
<213> ORGANISM: Homo sapiens

<400> SEQUENCE: 24

Ala Pro Thr Ile Arg Gly Asp Pro Glu Cys His Leu Phe Tyr Asn
1               5                   10                  15

<210> SEQ ID NO 25
<211> LENGTH: 15
<212> TYPE: PRT
<213> ORGANISM: Homo sapiens

<400> SEQUENCE: 25

Pro Pro Pro Leu Leu Pro Leu Leu Pro Leu Leu Leu Leu Leu Leu
1               5                   10                  15

<210> SEQ ID NO 26
<211> LENGTH: 15
<212> TYPE: PRT
<213> ORGANISM: Homo sapiens

<400> SEQUENCE: 26

Arg Gly Pro Leu Glu His Leu Tyr Ser Leu His Ile Pro Asn Cys
1               5                   10                  15

<210> SEQ ID NO 27
<211> LENGTH: 15
<212> TYPE: PRT

```
<213> ORGANISM: Homo sapiens

<400> SEQUENCE: 27

Cys Gly Val Tyr Thr Pro Arg Cys Gly Gln Gly Leu Arg Cys Tyr
1               5                   10                  15

<210> SEQ ID NO 28
<211> LENGTH: 15
<212> TYPE: PRT
<213> ORGANISM: Homo sapiens

<400> SEQUENCE: 28

Pro Leu Leu Leu Leu Leu Leu Gly Ala Ser Gly Gly Gly Gly Gly
1               5                   10                  15

<210> SEQ ID NO 29
<211> LENGTH: 15
<212> TYPE: PRT
<213> ORGANISM: Homo sapiens

<400> SEQUENCE: 29

Asp Gln Val Leu Glu Arg Ile Ser Thr Met Arg Leu Pro Asp Glu
1               5                   10                  15

<210> SEQ ID NO 30
<211> LENGTH: 15
<212> TYPE: PRT
<213> ORGANISM: Homo sapiens

<400> SEQUENCE: 30

Pro Lys Lys Leu Arg Pro Pro Ala Arg Thr Pro Cys Gln Gln
1               5                   10                  15

<210> SEQ ID NO 31
<211> LENGTH: 15
<212> TYPE: PRT
<213> ORGANISM: Homo sapiens

<400> SEQUENCE: 31

Cys Trp Cys Val Asn Pro Asn Thr Gly Lys Leu Ile Gln Gly Ala
1               5                   10                  15

<210> SEQ ID NO 32
<211> LENGTH: 15
<212> TYPE: PRT
<213> ORGANISM: Homo sapiens

<400> SEQUENCE: 32

Gln Ala Leu Val Met Gly Glu Gly Thr Cys Glu Lys Arg Arg Asp
1               5                   10                  15

<210> SEQ ID NO 33
<211> LENGTH: 18
<212> TYPE: DNA
<213> ORGANISM: Artificial Sequence
<220> FEATURE:
<223> OTHER INFORMATION: primer

<400> SEQUENCE: 33
gcgcgggtac ctgtgaaa                                                    18

<210> SEQ ID NO 34
<211> LENGTH: 21
<212> TYPE: DNA
<213> ORGANISM: Artificial Sequence
```

<220> FEATURE:
<223> OTHER INFORMATION: primer

<400> SEQUENCE: 34
tccctcagag tggtcgtcat c          21

<210> SEQ ID NO 35
<211> LENGTH: 1367
<212> TYPE: PRT
<213> ORGANISM: Homo sapiens

<400> SEQUENCE: 35

```
Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Tyr Leu His Ile Leu Leu Ile
    50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Thr Cys Gly Lys Arg Ala Cys
    210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
        275                 280                 285

Glu Ser Ser Asp Ser Glu Gly Phe Val Ile His Asp Gly Glu Cys Met
    290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Lys
                325                 330                 335

Lys Thr Lys Thr Ile Asp Ser Val Thr Ser Ala Gln Met Leu Gln Gly
```

```
                    340              345              350
Cys Thr Ile Phe Lys Gly Asn Leu Leu Ile Asn Ile Arg Arg Gly Asn
                355              360              365

Asn Ile Ala Ser Glu Leu Glu Asn Phe Met Gly Leu Ile Glu Val Val
            370              375              380

Thr Gly Tyr Val Lys Ile Arg His Ser His Ala Leu Val Ser Leu Ser
385              390              395              400

Phe Leu Lys Asn Leu Arg Leu Ile Leu Gly Glu Glu Gln Leu Glu Gly
                405              410              415

Asn Tyr Ser Phe Tyr Val Leu Asp Asn Gln Asn Leu Gln Gln Leu Trp
            420              425              430

Asp Trp Asp His Arg Asn Leu Thr Ile Lys Ala Gly Lys Met Tyr Phe
                435              440              445

Ala Phe Asn Pro Lys Leu Cys Val Ser Glu Ile Tyr Arg Met Glu Glu
            450              455              460

Val Thr Gly Thr Lys Gly Arg Gln Ser Lys Gly Asp Ile Asn Thr Arg
465              470              475              480

Asn Asn Gly Glu Arg Ala Ser Cys Glu Ser Asp Val Leu His Phe Thr
                485              490              495

Ser Thr Thr Thr Ser Lys Asn Arg Ile Ile Thr Trp His Arg Tyr
            500              505              510

Arg Pro Pro Asp Tyr Arg Asp Leu Ile Ser Phe Thr Val Tyr Tyr Lys
            515              520              525

Glu Ala Pro Phe Lys Asn Val Thr Glu Tyr Asp Gly Gln Asp Ala Cys
            530              535              540

Gly Ser Asn Ser Trp Asn Met Val Asp Val Asp Leu Pro Pro Asn Lys
545              550              555              560

Asp Val Glu Pro Gly Ile Leu Leu His Gly Leu Lys Pro Trp Thr Gln
                565              570              575

Tyr Ala Val Tyr Val Lys Ala Val Thr Leu Thr Met Val Glu Asn Asp
            580              585              590

His Ile Arg Gly Ala Lys Ser Glu Ile Leu Tyr Ile Arg Thr Asn Ala
                595              600              605

Ser Val Pro Ser Ile Pro Leu Asp Val Leu Ser Ala Ser Asn Ser Ser
            610              615              620

Ser Gln Leu Ile Val Lys Trp Asn Pro Pro Ser Leu Pro Asn Gly Asn
625              630              635              640

Leu Ser Tyr Tyr Ile Val Arg Trp Gln Arg Gln Pro Gln Asp Gly Tyr
                645              650              655

Leu Tyr Arg His Asn Tyr Cys Ser Lys Asp Lys Ile Pro Ile Arg Lys
                660              665              670

Tyr Ala Asp Gly Thr Ile Asp Ile Glu Glu Val Thr Glu Asn Pro Lys
                675              680              685

Thr Glu Val Cys Gly Gly Glu Lys Gly Pro Cys Cys Ala Cys Pro Lys
            690              695              700

Thr Glu Ala Glu Lys Gln Ala Glu Lys Glu Glu Ala Glu Tyr Arg Lys
705              710              715              720

Val Phe Glu Asn Phe Leu His Asn Ser Ile Phe Val Pro Arg Pro Glu
                725              730              735

Arg Lys Arg Arg Asp Val Met Gln Val Ala Asn Thr Thr Met Ser Ser
            740              745              750

Arg Ser Arg Asn Thr Thr Ala Ala Asp Thr Tyr Asn Ile Thr Asp Pro
            755              760              765
```

```
Glu Glu Leu Glu Thr Glu Tyr Pro Phe Phe Glu Ser Arg Val Asp Asn
            770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
                    805                 810                 815

Ala Ser Asn Phe Val Phe Ala Arg Thr Met Pro Ala Glu Gly Ala Asp
                820                 825                 830

Asp Ile Pro Gly Pro Val Thr Trp Glu Pro Arg Pro Glu Asn Ser Ile
            835                 840                 845

Phe Leu Lys Trp Pro Glu Pro Glu Asn Pro Asn Gly Leu Ile Leu Met
850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
                885                 890                 895

Asn Pro Gly Asn Tyr Thr Ala Arg Ile Gln Ala Thr Ser Leu Ser Gly
            900                 905                 910

Asn Gly Ser Trp Thr Asp Pro Val Phe Phe Tyr Val Gln Ala Lys Thr
        915                 920                 925

Gly Tyr Glu Asn Phe Ile His Leu Ile Ile Ala Leu Pro Val Ala Val
        930                 935                 940

Leu Leu Ile Val Gly Gly Leu Val Ile Met Leu Tyr Val Phe His Arg
945                 950                 955                 960

Lys Arg Asn Asn Ser Arg Leu Gly Asn Gly Val Leu Tyr Ala Ser Val
                965                 970                 975

Asn Pro Glu Tyr Phe Ser Ala Ala Asp Val Tyr Val Pro Asp Glu Trp
            980                 985                 990

Glu Val Ala Arg Glu Lys Ile Thr Met Ser Arg Glu Leu Gly Gln Gly
            995                1000                1005

Ser Phe Gly Met Val Tyr Glu Gly Val Ala Lys Gly Val Val Lys
    1010                1015                1020

Asp Glu Pro Glu Thr Arg Val Ala Ile Lys Thr Val Asn Glu Ala
    1025                1030                1035

Ala Ser Met Arg Glu Arg Ile Glu Phe Leu Asn Glu Ala Ser Val
    1040                1045                1050

Met Lys Glu Phe Asn Cys His His Val Val Arg Leu Leu Gly Val
    1055                1060                1065

Val Ser Gln Gly Gln Pro Thr Leu Val Ile Met Glu Leu Met Thr
    1070                1075                1080

Arg Gly Asp Leu Lys Ser Tyr Leu Arg Ser Leu Arg Pro Glu Met
    1085                1090                1095

Glu Asn Asn Pro Val Leu Ala Pro Pro Ser Leu Ser Lys Met Ile
    1100                1105                1110

Gln Met Ala Gly Glu Ile Ala Asp Gly Met Ala Tyr Leu Asn Ala
    1115                1120                1125

Asn Lys Phe Val His Arg Asp Leu Ala Ala Arg Asn Cys Met Val
    1130                1135                1140

Ala Glu Asp Phe Thr Val Lys Ile Gly Asp Phe Gly Met Thr Arg
    1145                1150                1155

Asp Ile Tyr Glu Thr Asp Tyr Tyr Arg Lys Gly Gly Lys Gly Leu
    1160                1165                1170
```

```
Leu Pro  Val Arg Trp Met Ser  Pro Glu Ser Leu Lys  Asp Gly Val
    1175             1180                 1185

Phe Thr  Thr Tyr Ser Asp Val  Trp Ser Phe Gly Val  Val Leu Trp
    1190             1195                 1200

Glu Ile  Ala Thr Leu Ala Glu  Gln Pro Tyr Gln Gly  Leu Ser Asn
    1205             1210                 1215

Glu Gln  Val Leu Arg Phe Val  Met Glu Gly Gly Leu  Leu Asp Lys
    1220             1225                 1230

Pro Asp  Asn Cys Pro Asp Met  Leu Phe Glu Leu Met  Arg Met Cys
    1235             1240                 1245

Trp Gln  Tyr Asn Pro Lys Met  Arg Pro Ser Phe Leu  Glu Ile Ile
    1250             1255                 1260

Ser Ser  Ile Lys Glu Glu Met  Glu Pro Gly Phe Arg  Glu Val Ser
    1265             1270                 1275

Phe Tyr  Tyr Ser Glu Glu Asn  Lys Leu Pro Glu Pro  Glu Glu Leu
    1280             1285                 1290

Asp Leu  Glu Pro Glu Asn Met  Glu Ser Val Pro Leu  Asp Pro Ser
    1295             1300                 1305

Ala Ser  Ser Ser Ser Leu Pro  Leu Pro Asp Arg His  Ser Gly His
    1310             1315                 1320

Lys Ala  Glu Asn Gly Pro Gly  Pro Gly Val Leu Val  Leu Arg Ala
    1325             1330                 1335

Ser Phe  Asp Glu Arg Gln Pro  Tyr Ala His Met Asn  Gly Gly Arg
    1340             1345                 1350

Lys Asn  Glu Arg Ala Leu Pro  Leu Pro Gln Ser Ser  Thr Cys
    1355             1360                 1365

<210> SEQ ID NO 36
<211> LENGTH: 15
<212> TYPE: PRT
<213> ORGANISM: Homo sapiens

<400> SEQUENCE: 36

Ser His Ala Leu Val Ser Leu Ser Phe Leu Lys Asn Leu Arg Leu
1               5                   10                  15

<210> SEQ ID NO 37
<211> LENGTH: 15
<212> TYPE: PRT
<213> ORGANISM: Homo sapiens

<400> SEQUENCE: 37

Val Val Thr Gly Tyr Val Lys Ile Arg His Ser His Ala Leu Val
1               5                   10                  15

<210> SEQ ID NO 38
<211> LENGTH: 15
<212> TYPE: PRT
<213> ORGANISM: Homo sapiens

<400> SEQUENCE: 38

Thr Gln Tyr Ala Val Tyr Val Lys Ala Val Thr Leu Thr Met Val
1               5                   10                  15

<210> SEQ ID NO 39
<211> LENGTH: 15
<212> TYPE: PRT
<213> ORGANISM: Homo sapiens

<400> SEQUENCE: 39
```

Leu Val Ile Met Leu Tyr Val Phe His Arg Lys Arg Asn Asn Ser
1               5                   10                  15

<210> SEQ ID NO 40
<211> LENGTH: 15
<212> TYPE: PRT
<213> ORGANISM: Homo sapiens

<400> SEQUENCE: 40

Ile Arg Gly Trp Lys Leu Phe Tyr Asn Tyr Ala Leu Val Ile Phe
1               5                   10                  15

<210> SEQ ID NO 41
<211> LENGTH: 15
<212> TYPE: PRT
<213> ORGANISM: Homo sapiens

<400> SEQUENCE: 41

Phe Phe Tyr Val Gln Ala Lys Thr Gly Tyr Glu Asn Phe Ile His
1               5                   10                  15

<210> SEQ ID NO 42
<211> LENGTH: 15
<212> TYPE: PRT
<213> ORGANISM: Homo sapiens

<400> SEQUENCE: 42

Ala Ser Asn Phe Val Phe Ala Arg Thr Met Pro Ala Glu Gly Ala
1               5                   10                  15

<210> SEQ ID NO 43
<211> LENGTH: 15
<212> TYPE: PRT
<213> ORGANISM: Homo sapiens

<400> SEQUENCE: 43

Arg Ala Ser Phe Asp Glu Arg Gln Pro Tyr Ala His Met Asn Gly
1               5                   10                  15

<210> SEQ ID NO 44
<211> LENGTH: 15
<212> TYPE: PRT
<213> ORGANISM: Homo sapiens

<400> SEQUENCE: 44

Ser Lys Met Ile Gln Met Ala Gly Glu Ile Ala Asp Gly Met Ala
1               5                   10                  15

<210> SEQ ID NO 45
<211> LENGTH: 15
<212> TYPE: PRT
<213> ORGANISM: Homo sapiens

<400> SEQUENCE: 45

Tyr Ser Phe Tyr Val Leu Asp Asn Gln Asn Leu Gln Gln Leu Trp
1               5                   10                  15

<210> SEQ ID NO 46
<211> LENGTH: 15
<212> TYPE: PRT
<213> ORGANISM: Homo sapiens

<400> SEQUENCE: 46

Phe Glu Leu Met Arg Met Cys Trp Gln Tyr Asn Pro Lys Met Arg

-continued

```
1               5                   10                  15
```

<210> SEQ ID NO 47
<211> LENGTH: 15
<212> TYPE: PRT
<213> ORGANISM: Homo sapiens

<400> SEQUENCE: 47

```
Asp Glu Arg Gln Pro Tyr Ala His Met Asn Gly Gly Arg Lys Asn
1               5                   10                  15
```

<210> SEQ ID NO 48
<211> LENGTH: 15
<212> TYPE: PRT
<213> ORGANISM: Homo sapiens

<400> SEQUENCE: 48

```
Val Ile Glu Gly Tyr Leu His Ile Leu Leu Ile Ser Lys Ala Glu
1               5                   10                  15
```

<210> SEQ ID NO 49
<211> LENGTH: 15
<212> TYPE: PRT
<213> ORGANISM: Homo sapiens

<400> SEQUENCE: 49

```
Leu Ile Ile Ala Leu Pro Val Ala Val Leu Leu Ile Val Gly Gly
1               5                   10                  15
```

<210> SEQ ID NO 50
<211> LENGTH: 15
<212> TYPE: PRT
<213> ORGANISM: Homo sapiens

<400> SEQUENCE: 50

```
Asp Tyr Arg Ser Tyr Arg Phe Pro Lys Leu Thr Val Ile Thr Glu
1               5                   10                  15
```

<210> SEQ ID NO 51
<211> LENGTH: 15
<212> TYPE: PRT
<213> ORGANISM: Homo sapiens

<400> SEQUENCE: 51

```
Gly Met Ala Tyr Leu Asn Ala Asn Lys Phe Val His Arg Asp Leu
1               5                   10                  15
```

<210> SEQ ID NO 52
<211> LENGTH: 15
<212> TYPE: PRT
<213> ORGANISM: Homo sapiens

<400> SEQUENCE: 52

```
Gly Val Leu Val Leu Arg Ala Ser Phe Asp Glu Arg Gln Pro Tyr
1               5                   10                  15
```

<210> SEQ ID NO 53
<211> LENGTH: 15
<212> TYPE: PRT
<213> ORGANISM: Homo sapiens

<400> SEQUENCE: 53

```
Trp Ser Phe Gly Val Val Leu Trp Glu Ile Ala Thr Leu Ala Glu
1               5                   10                  15
```

```
<210> SEQ ID NO 54
<211> LENGTH: 15
<212> TYPE: PRT
<213> ORGANISM: Homo sapiens

<400> SEQUENCE: 54

Ile Asp Ile Arg Asn Asp Tyr Gln Gln Leu Lys Arg Leu Glu Asn
1               5                   10                  15

<210> SEQ ID NO 55
<211> LENGTH: 15
<212> TYPE: PRT
<213> ORGANISM: Homo sapiens

<400> SEQUENCE: 55

Asn Cys His His Val Val Arg Leu Leu Gly Val Val Ser Gln Gly
1               5                   10                  15
```